United States Patent
Hu et al.

(10) Patent No.: US 11,819,519 B2
(45) Date of Patent: Nov. 21, 2023

(54) THERAPEUTIC AGENTS COMPRISING NUCLEIC ACIDS AND TCR MODIFIED IMMUNE CELLS AND USES THEREOF

(71) Applicants: HANGZHOU CONVERD CO., LTD., Zhejiang (CN); Yafei Hou, Mountain View, CA (US)

(72) Inventors: Fang Hu, Zhejiang (CN); Yafei Hou, Mountain View, CA (US); Jipo Sheng, Zhejiang (CN); Xiankui Tan, Zhejiang (CN)

(73) Assignees: HANGZHOU CONVERD CO., LTD., Zhejiang (CN); Yafei Hou, Mountain View, CA (US)

( * ) Notice: Subject to any disclaimer, the term of this patent is extended or adjusted under 35 U.S.C. 154(b) by 145 days.

(21) Appl. No.: 17/270,943

(22) PCT Filed: Aug. 26, 2019

(86) PCT No.: PCT/CN2019/102584
§ 371 (c)(1),
(2) Date: Feb. 24, 2021

(87) PCT Pub. No.: WO2020/038492
PCT Pub. Date: Feb. 27, 2020

(65) Prior Publication Data
US 2021/0393686 A1 Dec. 23, 2021

(30) Foreign Application Priority Data
Aug. 24, 2018 (CN) .......................... 201810972316.5

(51) Int. Cl.
| | |
|---|---|
| *A61K 35/17* | (2015.01) |
| *C12N 7/00* | (2006.01) |
| *C07K 14/74* | (2006.01) |
| *C07K 14/725* | (2006.01) |
| *A61P 35/00* | (2006.01) |
| *A61K 35/768* | (2015.01) |
| *A61K 38/17* | (2006.01) |
| *A61K 38/28* | (2006.01) |
| *A61K 39/00* | (2006.01) |

(52) U.S. Cl.
CPC ............ *A61K 35/17* (2013.01); *A61K 35/768* (2013.01); *A61K 38/1774* (2013.01); *A61K 38/28* (2013.01); *A61K 39/0011* (2013.01); *A61P 35/00* (2018.01); *C07K 14/7051* (2013.01); *C07K 14/70539* (2013.01); *C12N 7/00* (2013.01)

(58) Field of Classification Search
CPC .. A61K 35/17; A61K 35/768; A61K 38/1774; A61K 38/28; A61K 39/0011; A61P 35/00; C07K 14/7051; C07K 14/70539; C12N 7/00
See application file for complete search history.

(56) References Cited

U.S. PATENT DOCUMENTS

| | | | |
|---|---|---|---|
| 5,585,237 A | 12/1996 | Oppermann et al. | |
| 9,018,182 B2 * | 4/2015 | Koh ..................... | A61K 35/761 |
| | | | 435/320.1 |
| 9,540,657 B2 * | 1/2017 | Yu ........................ | C12N 15/85 |
| 10,064,927 B2 * | 9/2018 | Peretz ............ | A61K 39/001182 |
| 11,000,560 B2 | 5/2021 | Alemany et al. | |
| 2016/0250292 A1 | 9/2016 | Hu | |
| 2019/0030151 A1 | 1/2019 | Jones et al. | |
| 2019/0119350 A1 | 4/2019 | Lu et al. | |
| 2019/0134174 A1 | 5/2019 | Jones et al. | |
| 2022/0339220 A1 | 10/2022 | Hu | |

FOREIGN PATENT DOCUMENTS

| | | | |
|---|---|---|---|
| CN | 104415335 A | 3/2015 | |
| CN | 105802909 A | 7/2016 | |
| CN | 107849111 A | 3/2018 | |
| CN | 108137670 A | 6/2018 | |
| CN | 108261426 A | 4/2019 | |
| EP | 3067366 A1 | 9/2016 | |
| TW | 201740958 A | 12/2017 | |
| TW | 201805013 A | 2/2018 | |
| WO | 2013177247 A1 | 11/2013 | |
| WO | 2017075537 A1 | 5/2017 | |
| WO | WO-2017152042 A2 * | 9/2017 | ............. A61K 39/00 |
| WO | 2017177204 A1 | 10/2017 | |

OTHER PUBLICATIONS

Nguyen-Hoai et al. HER2/neu DNA vaccination by intradermal gene delivery in a mouse tumor model. OncoImmunology, 2012, 1(9) : 1537-1545. (Year: 2012).*
Berahovich et al. FLAG-tagged CD19-specific CAR-T cells eliminate CD19-bearing solid tumor cells in vitro and in vivo. Frontiers In Bioscience, Landmark, 2017, 22, 1644-1654. (Year: 2017).*

(Continued)

*Primary Examiner* — Arthur S Leonard
*Assistant Examiner* — Jianjian Zhu
(74) *Attorney, Agent, or Firm* — Renner, Otto, Boisselle & Sklar, LLP

(57) ABSTRACT

A therapeutic agent comprising a nucleic acid and a TCR modified immune cell and use thereof. The therapeutic agent comprises a first composition comprising a first active ingredient and a second composition comprising a second active ingredient. The first active ingredient includes or contains a nucleic acid having a labeling polypeptide coding sequence for being introduced into a tumor cell and/or a cancer cell. The labeling polypeptide has one or more epitope polypeptides which can be presented on a surface of the tumor cell and/or cancer cell by MHC class I molecules. The second composition comprises a second active ingredient in a second pharmaceutically acceptable carrier and the second active ingredient comprises a T cell receptor modified immune cell which can specifically recognize and bind to the epitope polypeptide presented by MHC class I molecules. The therapeutic agent achieves synergistic treatment effect and provides a new route for tumor treatment.

15 Claims, 23 Drawing Sheets
Specification includes a Sequence Listing.

(56) References Cited

OTHER PUBLICATIONS

Rao et al. E1A-induced apoptosis does not prevent replication of adenoviruses with deletion of E1b in majority of infected cancer cells. Cancer Gene Therapy. 2004; 11: 585-593. (Year: 2004).*
Doronin et al. Tumor-Specific, Replication-Competent Adenovirus Vectors Overexpressing the Adenovirus Death Protein. Journal of Virology, 2000, 74(13): 6147-6155. (Year: 2000).*
SCORE sequence alignment between 17270943-56 and Yu US9540657-486. (Year: 2022).*
Thanasupawat et al. INSL5 is a novel marker for human enteroendocrine cells of the large intestine and neuroendocrine tumours. Oncology Reportes.2013; 29: 149-154. (Year: 2013).*
Lanitis et al. A Human ErbB2-Specific T-Cell Receptor Confers Potent Antitumor Effector Functions in Genetically Engineered Primary Cytotoxic Lymphocytes. Human Gene Therapy, 2014, 25: 730-739. (Year: 2014).*
English Translation of International Search Report dated Dec. 3, 2019, for related International Patent Application No. PCT/CN2019/102584.
K.L. Knutson, et al., "Clonal Diversity of the T-Cell Population Responding to a Dominant HLA-A2 Epitope of HER-2/heu After Active Immunization in an Ovarian Cancer Patient", Human Immunology, vol. 63, Dec. 21, 2002.
Sujuan Ma, et al., "Construction of TCR Gene Modified Cytotoxic T Lymphocytes and its Application", Journal of International Oncology, Sep. 30, 2012.
Lanlin Zhang et al., "Progress in T Cell Receptor-Gene Engineered T Cell Immunotherapy for Solid Tumors", Abstract, Mar. 31, 2018.
Feifei Lou et al., "Tumor antigen-specific T cell immunotherapy", Abstract, vol. 29, No. 9, Sep. 30, 2017.
Extended European Search Report dated May 11, 2022, for corresponding European Patent Application No. 19851924.1.
Yangbing Zhao et al.; Primary Human Lymphocytes Transduced with NY-ESO-1 Antigen-Specific TCR Genes Recognize and Kill Diverse Human Tumor Cell Lines; The Journal of Immunology, Williams & Wilkins CO; Apr. 1, 2005; pp. 4415-4423; vol. 174, No. 7.
Remy Thomas et al.; NY-ESO-1 Based Immunotherapy of Cancer: Current Prospects; Frontiers in Immunology; May 1, 2018; pp. 1-14; vol. 9, Article 947.
Non-Final Office Action dated Nov. 25, 2022, for corresponding U.S. Appl. No. 16/798,465.
Mariano Stornaiuolo et al.; KDEL and KKXX Retrieval Signals Appended to the Same Reporter Protein Determine Different Trafficking between Endoplasmic Reticulum, Intermediate Compartment, and Golgi Complex; Molecular Biology of the Cell; Mar. 2003; vol. 14; pp. 889-902.
Office Action issued for corresponding Chinese National Stage Application No. 201810972316.5, dated Jul. 24, 2023.
Wang, Li, et al., "An endoplasmic reticulum retrieval signal sequence promotes MHC class I—presentation of exogenous CTL epitope peptides", Immunological Journal, vol. 22 No. 5, published Sep. 2006, DOI: 10. 13431 (translation of Abstract only).
First Office Action dated May 16, 2023 for corresponding Taiwanese Patent Application No. 108130349.

* cited by examiner

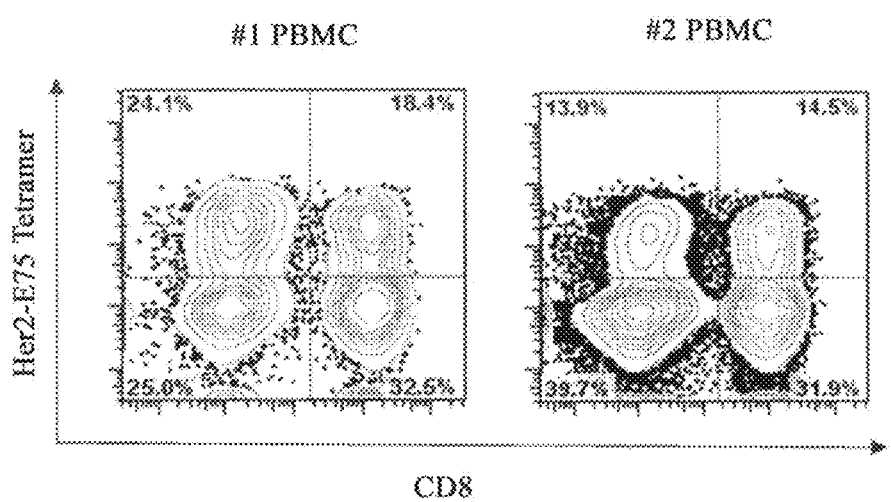
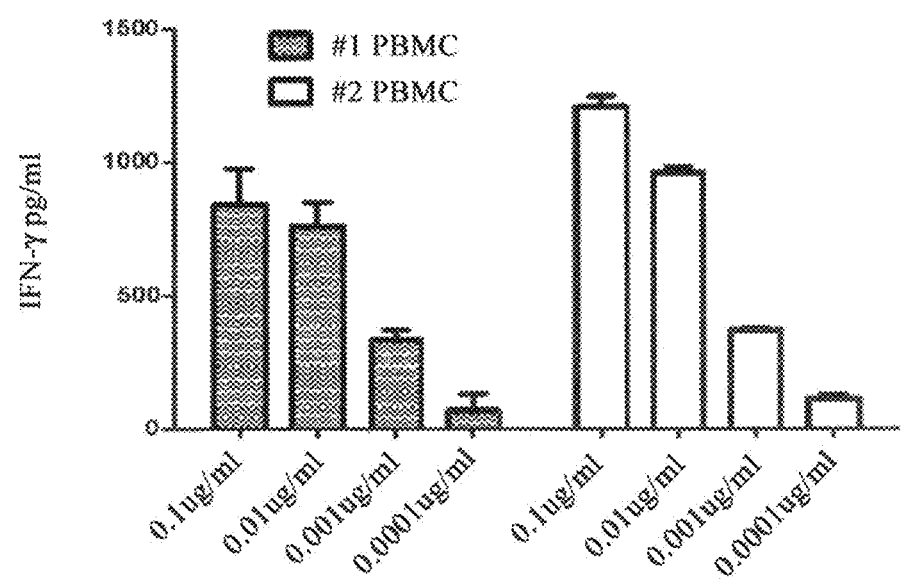

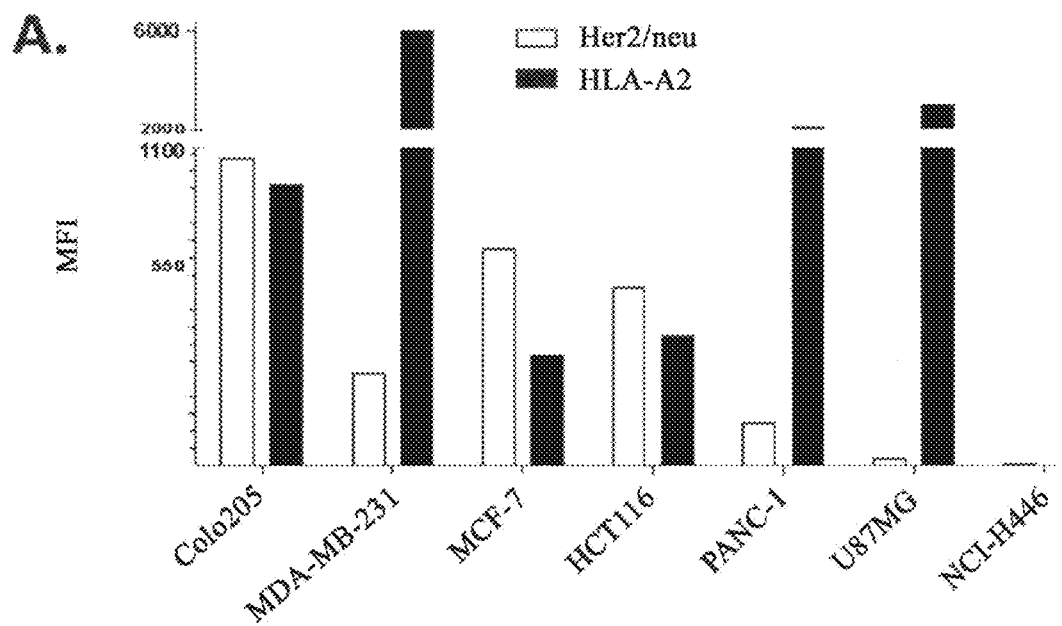
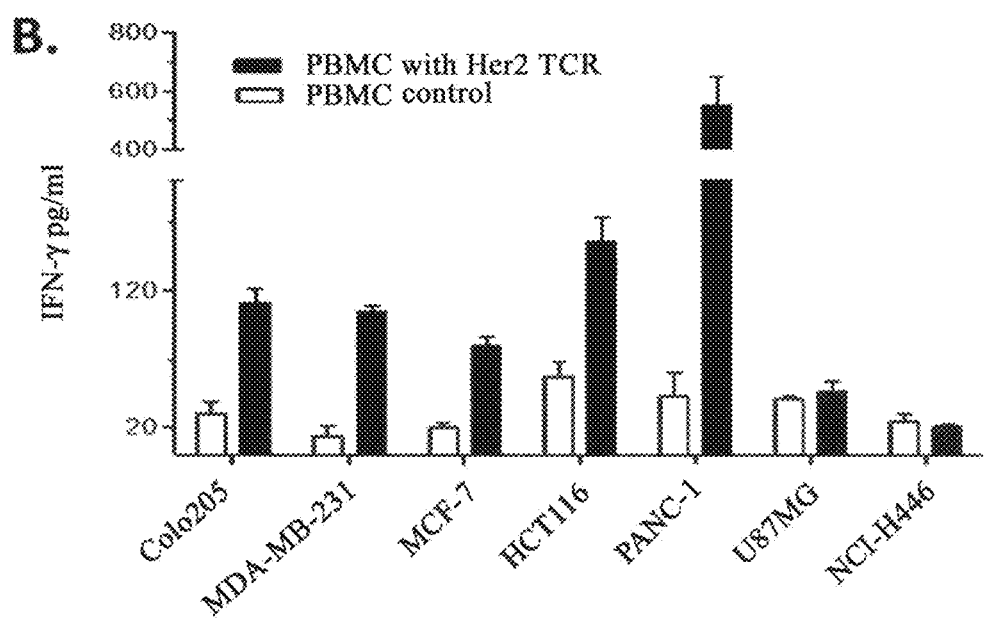

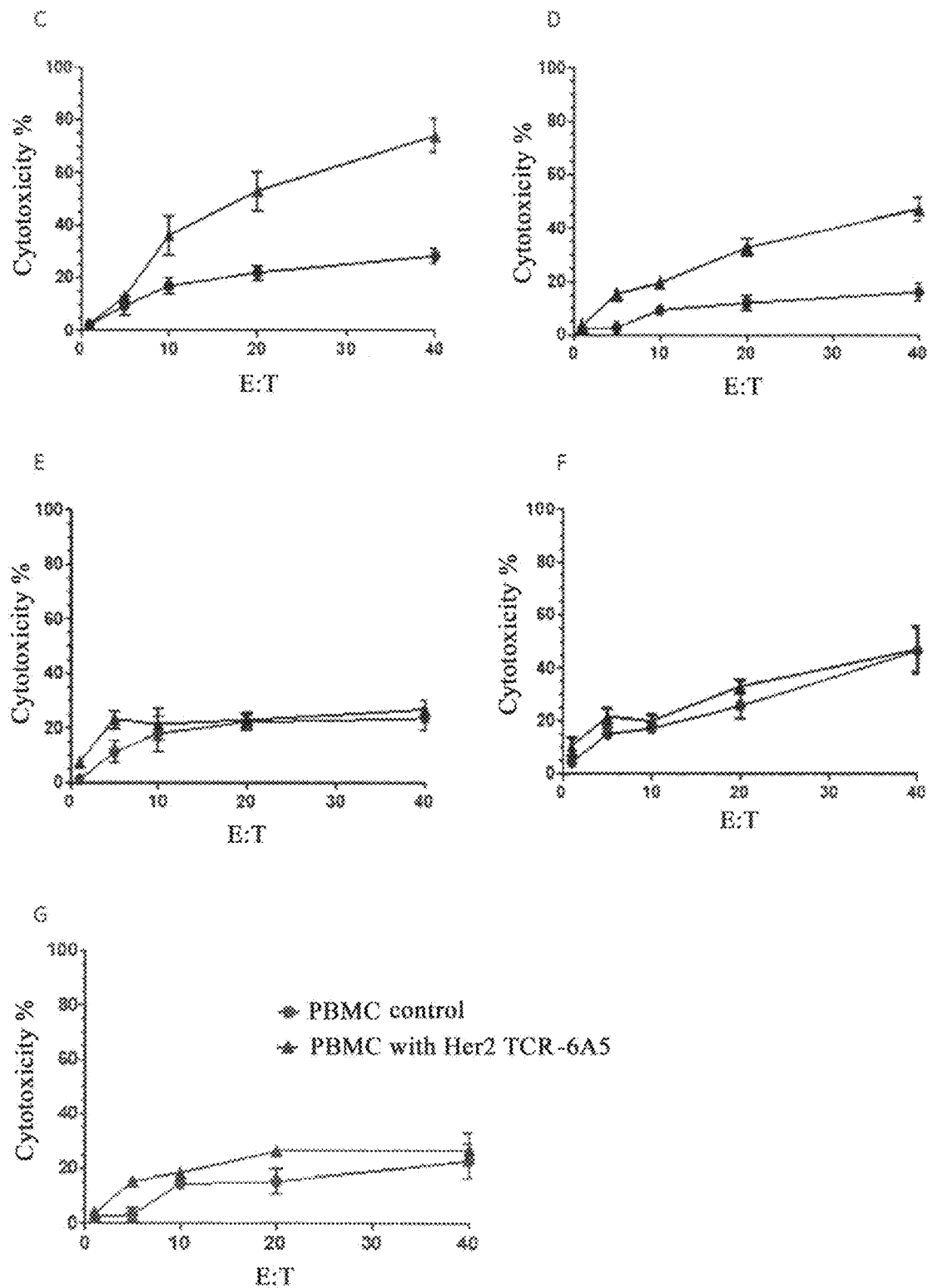

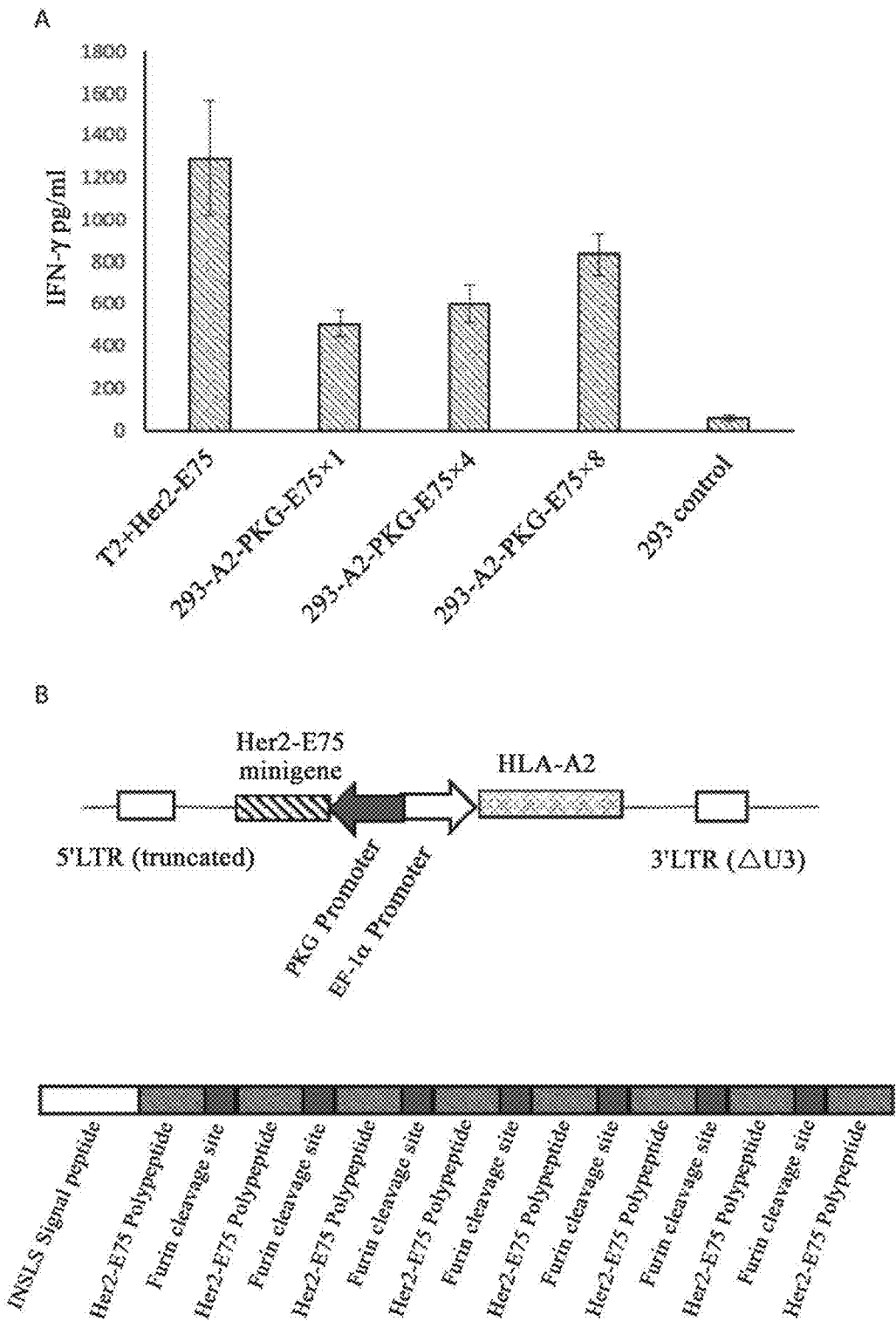

C

D

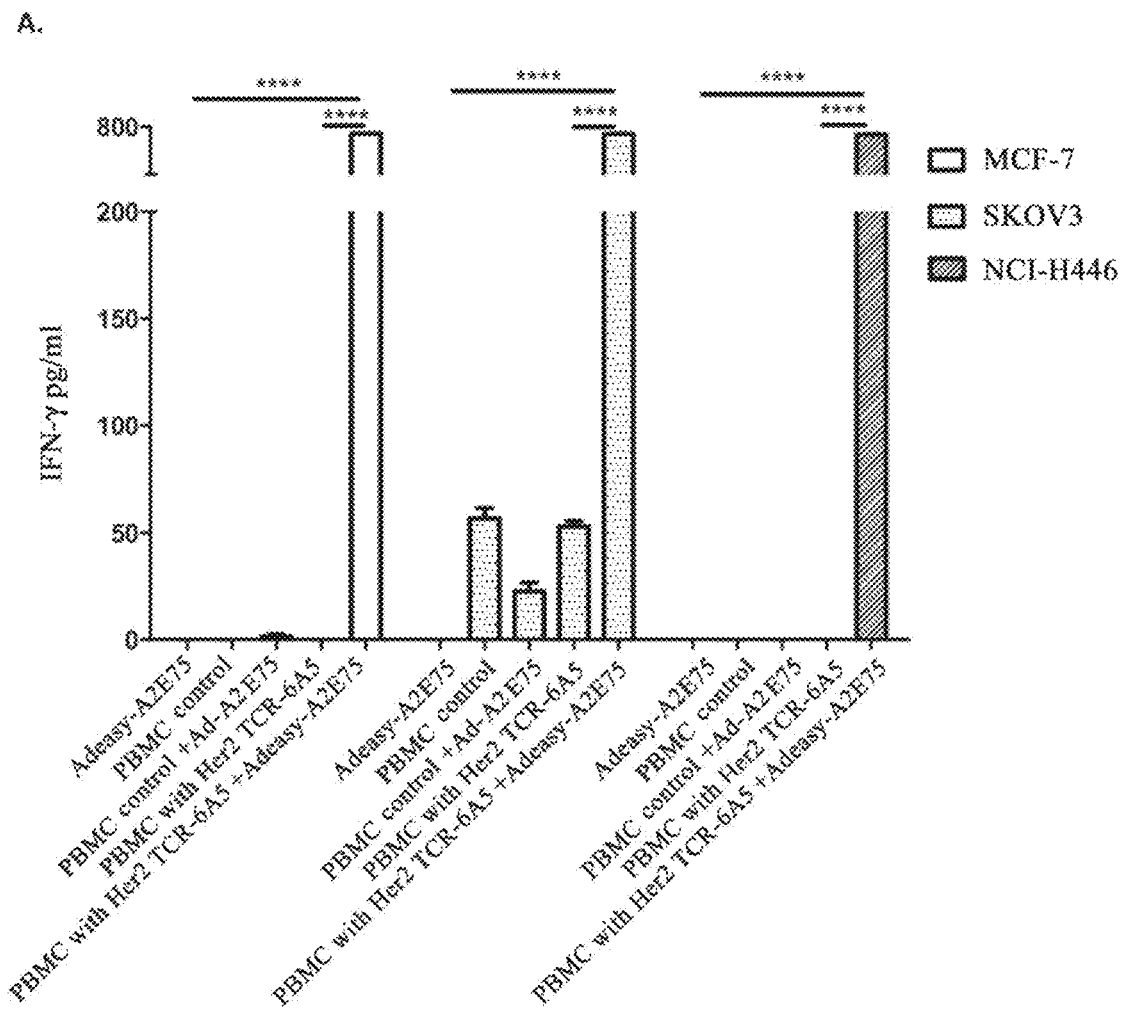

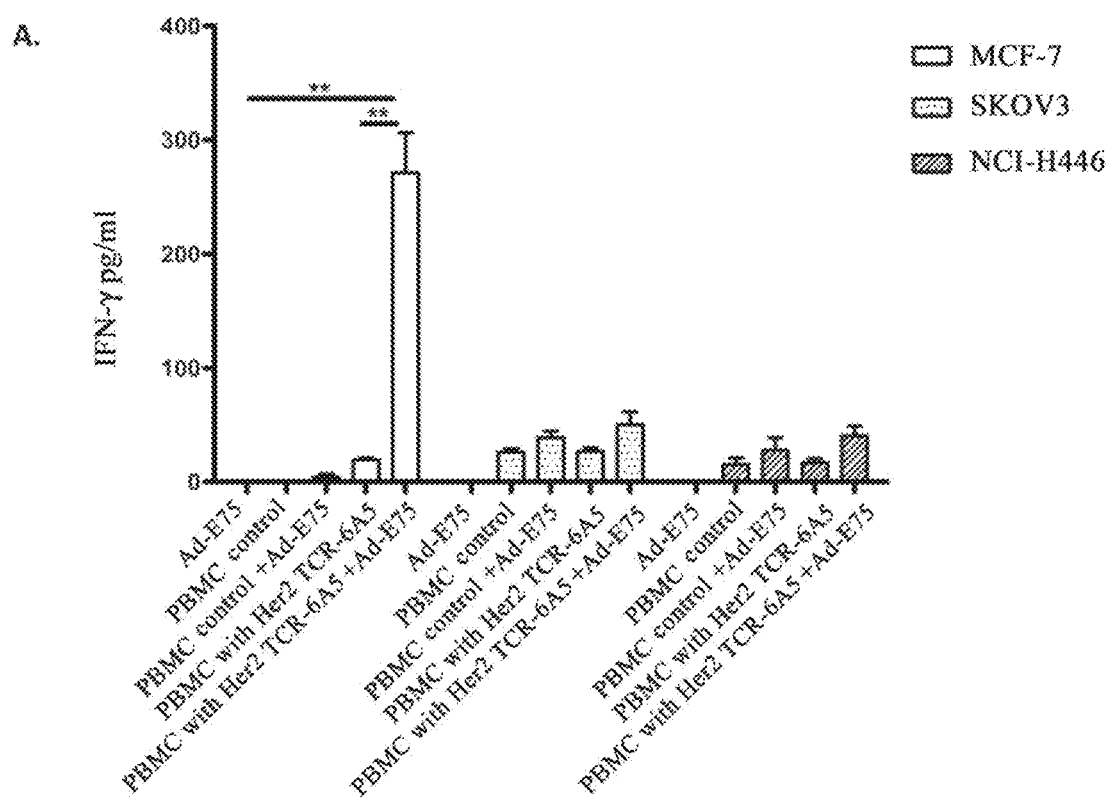

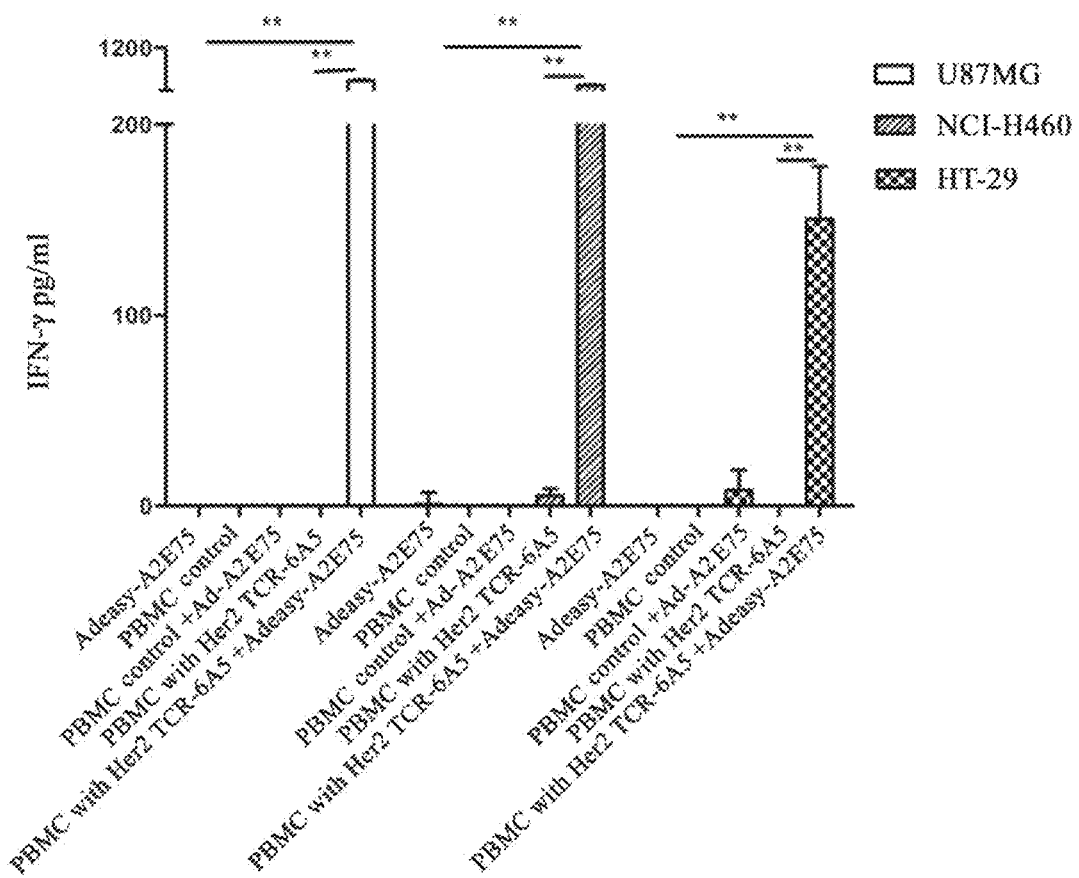

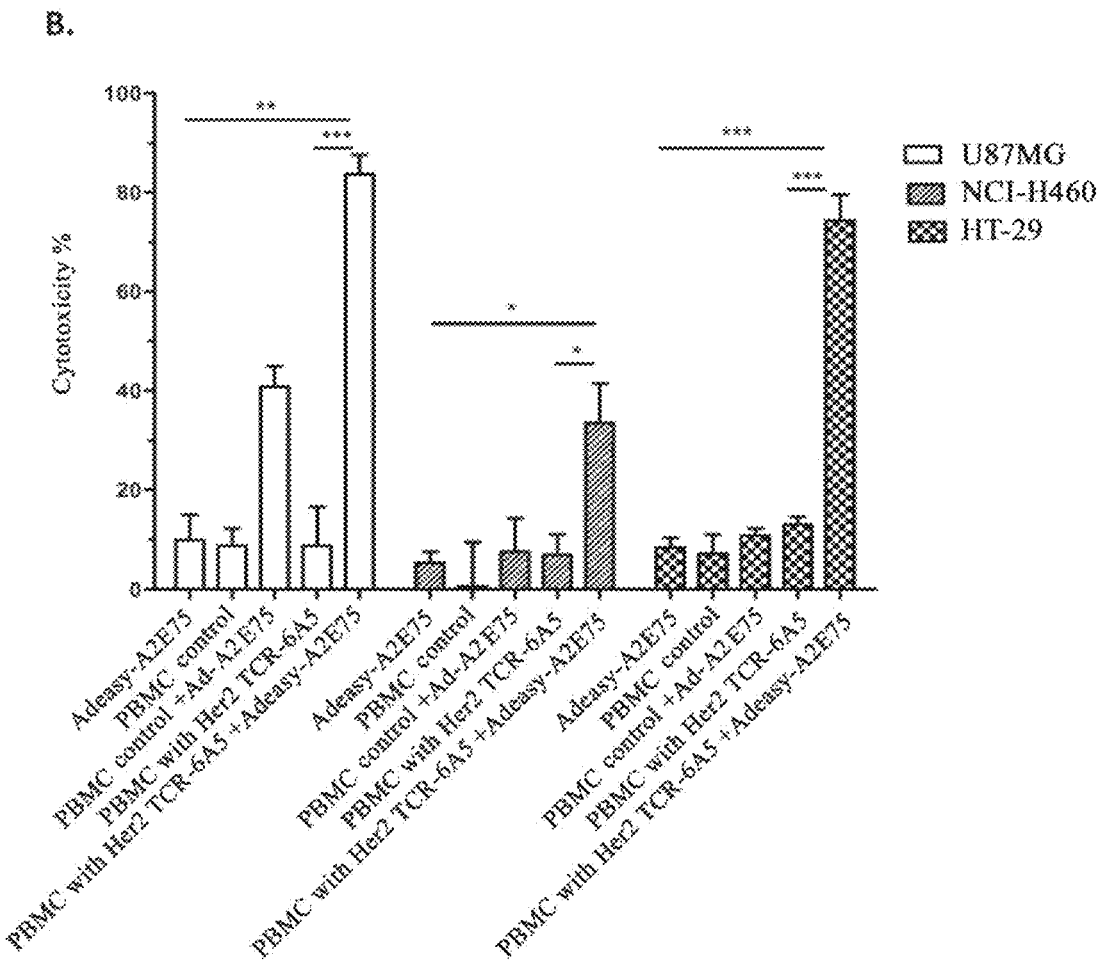

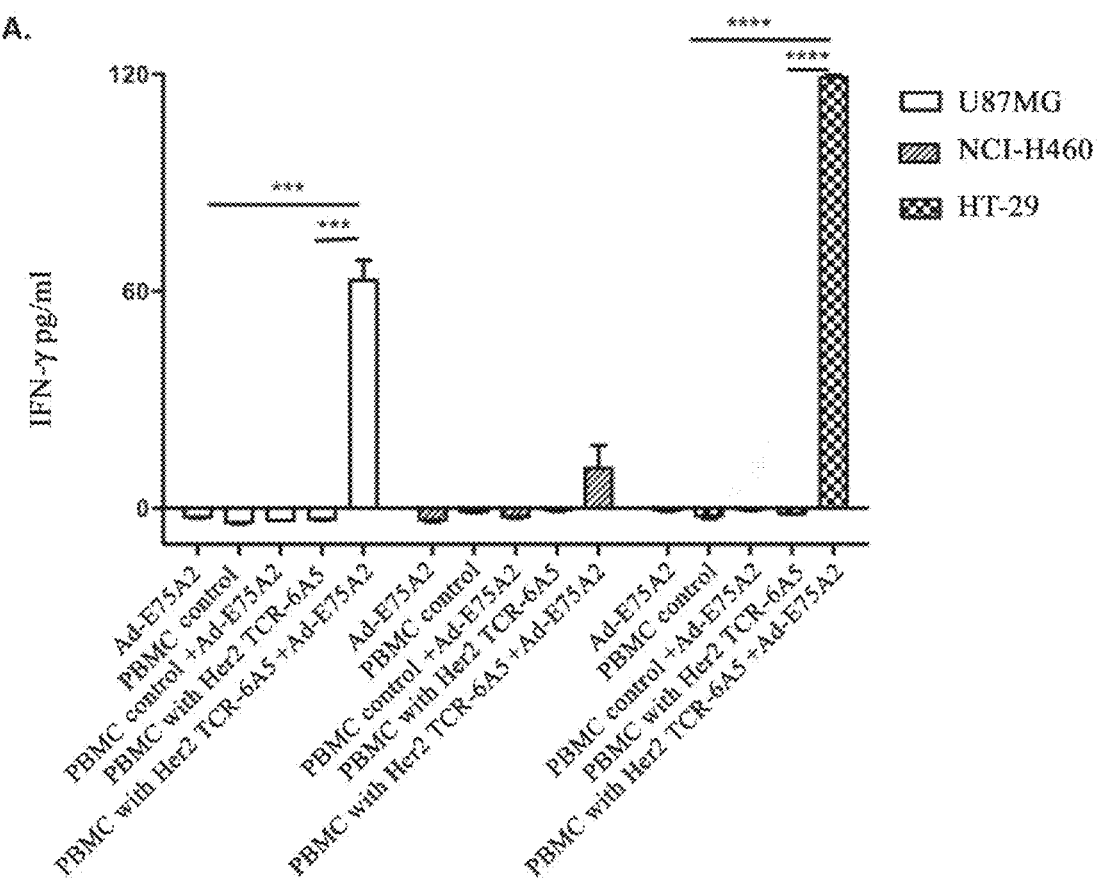

THERAPEUTIC AGENTS COMPRISING NUCLEIC ACIDS AND TCR MODIFIED IMMUNE CELLS AND USES THEREOF

REFERENCE TO A SEQUENCE LISTING

This application contains a Sequence Listing in computer readable form. A Sequence Listing in ASCII text format, submitted pursuant to 37 C.F.R. § 1.821, entitled 2021-08-26_SequenceListing_THOW4PUS01_ST25.txt, 79 kilobytes in size, created on Aug. 26, 2021 and filed via EFS-Web, is hereby incorporated by reference in its entirety.

FIELD OF THE INVENTION

The present invention belongs to the field of biotechnology, and particularly to a therapeutic agent comprising nucleic acids and TCR-modified immune cells, a labeling polypeptide, a coding nucleic acid, an expression vector, an oncolytic virus, a kit and uses thereof.

BACKGROUND OF THE INVENTION

As immune checkpoint inhibitors such as CTLA-4 and PD-1/PD-L1 have shown significant anti-tumor efficacy in clinical trials (see "Cancer Cell 27, 450-461 (2015)"), and adoptive T cell therapy, represented by CAR-T (Chimeric Antigen Receptor-T Cells), has shown long-term effective therapeutic effects on B-cell hematological tumors (see "N Engl J Med 2017; 377:2545-2554"), tumor immunotherapy has become one of the most promising areas. It is expected to transform malignant tumors into controllable chronic diseases, and even cure certain advanced cancers. Tumor immunotherapy is mainly achieved by stimulating endogenous anti-tumor T cell function, or adoptive transfer of tumor-specific T cells cultured in vitro to achieve the effect of killing and eliminating cancer cells in the body. Early tumor vaccines targeted tumor-associated antigens (TAA) derived from self-proteins, which try to induce specific anti-tumor immune responses in the body, but most of the related clinical trials were unsuccessful (see "Nat Rev Clin Oncol. 2014 November; 11(11):630-2."). One of the main issues is that the high-affinity T cells against these tumor-associated antigens are mostly eliminated by the central tolerance mechanism of the thymus during the development and differentiation process. Tumor vaccines, even with help of strong adjuvants, such as use of mature dendritic cells to present antigens, most of the specific T cells induced in the body are low-affinity T cells that cannot recognize tumor cells (see "J Immunol. 2008 Feb. 1; 180(3):1526-34"). In order to overcome this issue, development of personalized vaccines targeting neoantigens derived from gene mutations is an ongoing trend, and initial effects have been observed in clinical trials, but more clinical trials are needed to further verify efficacy of this type of tumor vaccine (see "Nat Rev Drug Discov. 2018 May 30; 17(6):393"; "Front Immunol. 2017; 8:1848"). Another problem to tumor immunotherapy is the immunosuppressive microenvironment produced during tumor occurrence and development. The tumor microenvironment (TME) has a strong inhibitory effect on the differentiation and proliferation of specific T cells and the anti-tumor function thereof (see "Curr Opin Immunol. 2016 April; 39:1-6").

To address these problems, an effective treatment strategy is adoptive transfer of T cells obtained in vitro that can effectively recognize tumor antigens. These T cells are derived from infiltrating T cells (TILs) of tumor tissues, or peripheral blood T cells (TCR-T) that can effectively recognize tumor antigens after genetic modification with an antigen-specific T cell receptor (TCR). In vitro culture avoids the inhibitory microenvironment of tumor tissues and provides optimized culture conditions, so that a sufficient number of anti-tumor T cells can be obtained for adoptive transfusion therapy (see "Adv Immunol. 2016; 130:279-94"). Adoptive T cell therapy includes CAR-T therapy based on chimeric antigen receptor and TCR-T therapy based on T cell receptor. CAR-T mainly targets tumor antigens expressed on the cell surface. Although number of recognized tumor antigens is limited, CAR-T targeting CD19 has shown significant clinical efficacy against hematological tumors including B-cell leukemia and lymphoma and some products have been approved by FDA and marketed (see "N Engl J Med. 2017 Oct. 5; 377(14):1313-1315"). For treatment of solid tumors, there is no clear clinical effect that has been observed in CAR-T. TCR-T mainly targets polypeptide antigens presented by human major histocompatibility antigen HLA molecules. Epitope polypeptides can be derived from intracellular proteins and cell membrane surface proteins. The type and number of target antigens are far more than the tumor antigens recognized by CAR-T (see the reference document "Int Immunol. 2016 07; 28(7):349-53"). TCR-T therapy is considered to be the most promising immune cell gene therapy for solid tumors (see "Adv Immunol. 2016; 130:279-94"). In the treatment of solid tumors, TCR-T therapy targeted NY-ESO-1 antigen has also been observed to have a clear effect in the second phase of clinical trials (see "Front Immunol. 2018; 9:947"). Her2/neu protein is overexpressed in a variety of cancer cells of epithelial origin, such as breast cancer, gastric cancer, colorectal cancer, ovarian cancer, pancreatic cancer, lung cancer, esophageal cancer, bladder cancer, kidney cancer, etc. (see "Trends in Molecular Med, 2013; 19:677"), making Her2/neu become an appropriate target for immunotherapy. T cells that specifically recognize the Her2/neu epitope peptide 369-377 have been successfully isolated from ascites of ovarian cancer with high expression of Her2/neu (see "J. Exp. Med. 1995; 181: 2109-2117"). A tumor vaccine targeting the Her2/neu 369-377 polypeptide antigen has entered a clinical trial, but the third phase of the clinical trial failed to achieve the predetermined goal of prolonging patient survival (world wide web.onclive.com/web-exclusives/phase-iii-nelipepimuts-study-in-breast-cancer-halted-after-futility-review). The adoptive transfusion of CAR-T cells cultured in vitro and targeted Her2/neu antigen entered a clinical trial as the first CAR-T therapy to treat solid tumors, which, however, was terminated due to the strong cytokine release syndrome (CRS) that caused the death of the patient (see "Nature Med, 2016; 22:26"). Severe cytokine release syndrome and neurotoxicity are common toxic reactions in CAR-T therapy (see "Blood, 2016; 127:3321"). At present, TCR-T therapy in clinical trials has not yet shown the severe cytokine release syndrome toxicity as shown in CAR-T therapy. TCR-T targeted Her2/neu antigen for treatment of solid tumors may avoid severe cytokine release syndrome. Her2/neu is a tumor-associated antigen derived from self-proteins. Most of the T cells that recognize this antigen are eliminated by the central tolerance selection mechanism. Therefore, it is very difficult to obtain natural T cells that specifically recognize tumor cells from peripheral blood. The induced polypeptide-specific T cells generally cannot effectively recognize tumor-associated antigens expressed at low levels on the surface of tumor cells (see "Cancer Res. 1998; 58(21):4902-8"). In order to obtain TCRs that can be used to prepare TCR-T and can effectively recognize tumor cells, the complementarity determining regions (CDRs) on the TCR are generally subjected to site-directed mutagenesis, or obtain high-affinity antigen-specific TCR by induction from a humanized mouse T cell bank that has not been screened by the central tolerance mechanism (see "Front Immunol. 2013; 4: 363"). However, the TCR-T prepared based on the high-affinity TCR obtained by this strategy has produced severe off-target toxicity against normal tissue cells in clinical trials (see "Sci Rep. 2016 Jan. 13; 6: 18851"). In addition, the target recognized by TCR-T is an antigen complex formed by the HLA molecule, $\beta_2$-microglobulin (beta2-Microglobulin) and an antigen polypeptide on the cell surface (in which the HLA protein and $\beta_2$-microglobulin paired to form MHC class I molecules). The antigen recognition ability of TCR-T is not only restricted by HLA molecules, but also closely related to the expression of HLA molecules and tumor antigens in tumor cells, and the integrity of the HLA antigen polypeptide presentation pathway. However, in the process of tumor development, the expression of HLA molecules in tumor cells is often reduced, or the function of related molecules in the HLA antigen presentation pathway in the cytoplasm is lost, which results in antigen polypeptides that cannot be effectively presented to the surface of tumor cells by HLA molecules so as to be recognized by T cells (see "Cancer Gene Ther. 2002 December; 9(12):1043-55"). The absence of presentation pathway of such HLA class I antigen (i.e., the MHC class I antigen presentation pathway) is a mechanism for tumor immune evasion, which is related to gene mutation or abnormal expression of antigen presenting molecules such as HLA, $\beta_2$-microglobulin, TAP, tapasin, LMP and ERAP in tumor cells, and may also be related to the excessive functional activation of tumor transforming molecules such as RAS, MYC, MOS, and Her2/Neu (see "Trends in Molecular Medicine, 2013, 19(11): 677-681"). In addition, diversity of tumor tissues is also manifested by the heterogeneity of tumor antigen expression. Tumor cells with low or no tumor antigen expression may escape recognition and killing of TCR-T, thereby affecting efficacy of TCR-T (see "Trends Immunol. 2016 06; 37(6):349-351").

Therefore, a challenge to TCR-T therapy is how to promote tumor-associated antigen targeting TCR-Ts to effectively recognize and kill tumor cells.

SUMMARY OF THE INVENTION

In order to solve the above-mentioned problems in the prior art, the present invention provides a therapeutic agent, a labeling polypeptide, a coding nucleic acid, an expression vector, an oncolytic virus, a kit and uses thereof.

Specifically, the present invention provides:

(1) A therapeutic agent for treatment of tumors and/or cancers, comprising:
 (a) a first composition, wherein the first composition comprises a first active ingredient in a first pharmaceutically acceptable carrier, and the first active ingredient includes or contains a nucleic acid having a labeling polypeptide coding sequence for being introduced into a tumor cell and/or a cancer cell; the labeling polypeptide has one or more amino acid sequences of epitope polypeptide, the epitope polypeptide can be presented on the surface of the tumor cell and/or cancer cell by MHC class I molecules; and
 (b) a second composition, wherein the second composition comprises a second active ingredient in a second pharmaceutically acceptable carrier, and the second active ingredient comprises a T cell receptor modified immune cell; the TCR-modified immune cell can specifically recognize and bind to the epitope polypeptide presented by the MHC class I molecules.

(2) The therapeutic agent of (1), wherein the amino acid sequence of the epitope polypeptide is derived from an amino acid sequence of a protein that exists in the nature, or the amino acid sequence of the epitope polypeptide is an artificially synthesized amino acid sequence that does not exists in the nature; preferably, the protein that exists in the nature includes a human-derived protein and a protein of species other than human.

(3) The therapeutic agent of (1), wherein the amino acid sequence of the epitope polypeptide is derived from an amino acid sequence of a tumor-associated antigen or a tumor-specific antigen.

(4) The therapeutic agent of (1), wherein the labeling polypeptide comprises the following amino acid sequences that are operatively linked in an orderly tandem fashion: an amino acid sequence of a N-terminal signal peptide, one or more amino acid sequence(s) of the epitope polypeptide, an amino acid sequence of an optional C-terminal endoplasmic reticulum retention signal peptide; wherein, when the labeling polypeptide comprises multiple amino acid sequences of the epitope polypeptides, the amino acid sequences of every two adjacent epitope polypeptides are linked by an amino acid sequence of cleavable linker polypeptide.

(5) The therapeutic agent of (4), wherein the amino acid sequence of epitope polypeptide includes Her2/neu 369-377 as shown in SEQ ID NO: 3, NY-ESO-1 157-165, NY-ESO-1 1-11, NY-ESO-1 53-62, NY-ESO-1 18-27, N-ras 55-64, K-ras 224-232, K-ras 10-18, K-ras 10-19, H3.3K27M 26-35, SSX-2 41-49, MAGE-C2 336-344, MAGE-C2 191-200, MAGE-C2 307-315, MAGE-C2 42-50, MAGE-A1 120-129, MAGE-A1 230-238, MAGE-A1 161-169, KK-LC-1 76-84, p53 99-107, HPV16-E6 29-38, HPV16-E7 11-19, HPV16-E7 11-19, EBV-LMP1 51-59 and EBV-LMP1 125-133.

(6) The therapeutic agent of (1), wherein the nucleic acid further has an HLA protein coding sequence, wherein the HLA protein coding sequence and the labeling polypeptide coding sequence are under control of their respective promoter, or the HLA protein coding sequence and the labeling polypeptide coding sequence are under control of the same promoter, and the HLA protein coding sequence is operatively linked to the labeling polypeptide coding sequence through a cleavable linker polypeptide coding sequence.

(7) The therapeutic agent of (6), wherein the HLA protein is HLA-A2 protein, and the amino acid sequence of HLA-A2 is as shown in SEQ ID NO: 29.

(8) The therapeutic agent of (1), wherein the first composition and the second composition are present separately in the therapeutic agent without being mixed with each other.

(9) The therapeutic agent of (1), wherein the nucleic acid includes DNA or RNA; and the RNA includes mRNA transcribed from the DNA.

(10) The therapeutic agent of (1), wherein the first active ingredient is a recombinant virus, and a genome of the recombinant virus has the labeling polypeptide coding sequence and an optional HLA protein coding sequence; wherein the recombinant virus includes a replication-selective recombinant oncolytic virus or a replication-defective recombinant virus.

(11) The therapeutic agent of (10), wherein the replication-defective recombinant virus is derived from adenovirus, adenovirus-associated virus (AAV), herpes simplex virus, vaccinia virus, influenza virus, Alphavirus, or Sendai virus.

(12) The therapeutic agent of (10), wherein the replication-defective recombinant virus is a recombinant adenovirus obtained by genetically modifying an adenovirus type 5, and E1 gene is deleted from the genome of the recombinant adenovirus, and the labeling polypeptide coding sequence and the optional HLA protein coding sequence are included at the site of the deleted E1 gene.

(13) The therapeutic agent of (10), wherein the replication-selective recombinant oncolytic virus is derived from a genetically mutated virus with oncolytic effect or a wild-type virus with oncolytic effect; preferably, the replication-selective recombinant oncolytic virus is derived from adenovirus, vaccinia virus, herpes simplex virus, measles virus, Semliki forest virus, vesicular stomatitis virus, polio virus, retrovirus, reovirus, Seneca valley virus, Echo-type enterovirus, Coxsackie virus, Newcastle disease virus and Malaba virus with oncolytic effect.

(14) The therapeutic agent of (10), wherein the replication-selective recombinant oncolytic virus is a recombinant oncolytic adenovirus obtained by genetically modifying an adenovirus type 5, and E1B-55K gene and/or E1B-19K gene are deleted from the genome of the recombinant oncolytic adenovirus, and E1A gene coding sequence is comprised in the genome of the recombinant oncolytic adenovirus; preferably, the E1A gene coding sequence is under control of an exogenous promoter.

(15) The therapeutic agent of (10) or (14), wherein the recombinant oncolytic virus is a recombinant oncolytic adenovirus obtained by genetically modifying an adenovirus type 5, and E1A gene of the recombinant oncolytic adenovirus is modified so that the expressed E1A protein cannot bind to pRb protein; preferably, the E1A gene coding sequence is under control of an exogenous promoter.

(16) The therapeutic agent of (14) or (15), wherein E3 gene of the recombinant oncolytic adenovirus is completely or partially deleted.

(17) The therapeutic agent of (1), wherein the immune cells include primitive T cells or their precursor cells, NKT cells, or T cell strains.

(18) The therapeutic agent of (9), wherein the first composition comprises a therapeutically effective amount of the DNA or a therapeutically effective amount of the mRNA.

(19) The therapeutic agent of (10), wherein the first composition comprises a therapeutically effective amount of the recombinant virus.

(20) The therapeutic agent of (1), wherein the second composition comprises a therapeutically effective amount of the T cell receptor-modified immune cells.

(21) The therapeutic agent of (9), wherein the DNA is formulated to be administered by intratumoral injection; and the mRNA is formulated to be administered by intratumoral injection.

(22) The therapeutic agent of (10), wherein the recombinant virus is formulated to be administered by intratumoral injection, intraperitonealy, intra-subarachnoidly or intravenously.

(23) The therapeutic agent of (1), wherein the immune cells are formulated to be administered intraarterially, intravenously, hypodermically, intracutaneous, intratumorally, intralymphatically, intralympnode, intra-subarachnoidly, intramedullarily, intramuscularly or intraperitoneally.

(24) The therapeutic agent of (1), wherein the therapeutic agent is composed of the first composition and the second composition.

(25) Use of the therapeutic agent of any one of (1) to (24) in preparation of a medication for treatment of tumors and/or cancers.

(26) The use of (25), wherein the tumors and/or cancers include: breast cancer, head and neck tumor, synovial cancer, kidney cancer, connective tissue cancer, melanoma, lung cancer, esophageal cancer, colon cancer, rectal cancer, brain cancer, liver cancer, bone cancer, choriocarcinoma, gastrinoma, pheochromocytoma, prolactinoma, von Hippel-Lindau disease, Zollinger-Ellison syndrome, anal cancer, cholangiocarcinoma, bladder cancer, ureteral carcinoma, glioma, neuroblastoma, meningioma, spinal cord tumor, osteochondroma, chondrosarcoma, Ewing's sarcoma, cancer of unknown primary site, carcinoid, fibrosarcoma, Paget's disease, cervix carcinoma, gallbladder cancer, eye cancer, Kaposi's sarcoma, prostate cancer, testicular cancer, cutaneous squamous cell carcinoma, mesothelioma, multiple myeloma, ovarian cancer, pancreatic endocrine tumor, glucagon tumor, pancreatic cancer, penile cancer, pituitary cancer, soft tissue sarcoma, retinoblastoma, small bowel cancer, gastric cancer, thymic cancer, trophoblastic carcinoma, hydatidiform mole, endometrial cancer, vaginal cancer, vulvar cancer, mycosis fungoides, insulinoma, heart cancer, meningeal cancer, blood cancer, peritoneal cancer and pleural cancer.

(27) A labeling polypeptide comprising the following amino acid sequences that are operatively linked in an orderly tandem fashion: an amino acid sequence of a N-terminal signal peptide, one or more amino acid sequence(s) of epitope polypeptide, an amino acid sequence of an optional C-terminal endoplasmic reticulum retention signal peptide; wherein, when the labeling polypeptide comprises multiple amino acid sequences of the epitope polypeptides, the amino acid sequences of every two adjacent epitope polypeptides are linked by an amino acid sequence of cleavable linker polypeptide; preferably, the cleavable linker polypeptide is a furin recognition polypeptide.

(28) The labeling polypeptide of (27), wherein the amino acid sequence of the epitope polypeptide includes Her2/neu 369-377 as shown in SEQ ID NO: 3, NY-ESO-1 157-165, NY-ESO-1 1-11, NY-ESO-1 53-62, NY-ESO-1 18-27, N-ras 55-64, K-ras 224-232, K-ras 10-18, K-ras 10-19, H3.3K27M 26-35, SSX-2 41-49, MAGE-C2 336-344, MAGE-C2 191-200, MAGE-C2 307-315, MAGE-C2 42-50, MAGE-A1 120-129, MAGE-A1 230-238, MAGE-A1 161-169, KK-LC-1 76-84, p53 99-107, HPV16-E6 29-38, HPV16-E7 11-19, HPV16-E7 11-19, EBV-LMP1 51-59 and EBV-LMP1 125-133.

(29) The labeling polypeptide of (27), wherein the amino acid sequence of the labeling polypeptide has at least 98% identity with the amino acid sequence as shown in SEQ ID NO: 24, SEQ ID NO: 36, SEQ ID NO: 56, or SEQ ID NO: 60; preferably, the amino acid sequence of the labeling polypeptide is as shown in SEQ ID NO: 24, SEQ ID NO: 36, SEQ ID NO: 56, or SEQ ID NO: 60.

(30) An isolated nucleic acid having a coding sequence of the labeling polypeptide of any one of (27) to (29).

(31) The nucleic acid of (30), wherein the nucleic acid further has an HLA protein coding sequence, wherein the HLA protein coding sequence and the labeling polypeptide coding sequence are under control of their respective promoter, or the HLA protein coding sequence and the labeling polypeptide coding sequence are under control of the same promoter, and the HLA protein coding sequence is operatively linked to the labeling polypeptide coding sequence through a cleavable linker polypeptide coding sequence.

(32) The nucleic acid of (30), wherein the nucleic acid includes DNA and mRNA.

(33) The nucleic acid of (32), wherein the nucleic acid is DNA with a nucleotide sequence as shown in SEQ ID NO:

25, SEQ ID NO: 26, SEQ ID NO: 27, SEQ ID NO: 57, SEQ ID NO: 58 or SEQ ID NO: 61.

(34) A recombinant expression vector containing the nucleic acid of any one of (30) to (33), and/or its complementary sequence.

(35) An isolated recombinant virus, wherein a genome of the recombinant virus has the nucleic acid of any one of (30) to (33); and, the recombinant virus includes a replication-selective recombinant oncolytic virus or a replication-defective recombinant virus.

(36) The recombinant virus of (35), wherein the replication-defective recombinant virus is derived from adenovirus, adeno-associated virus (AAV), herpes simplex virus, vaccinia virus, influenza virus, Alphavirus, or Sendai virus.

(37) The recombinant virus of (35), wherein the replication-defective recombinant virus is a recombinant adenovirus obtained by genetically modifying an adenovirus type 5, and E1 gene is deleted from the genome of the recombinant adenovirus, and the labeling polypeptide coding sequence and the optional HLA protein coding sequence are included at the site of the deleted E1 gene.

(38) The recombinant virus of (35), wherein the recombinant virus is a replication-selective recombinant oncolytic virus which is derived from a genetically mutated virus with oncolytic effect or a wild-type virus with oncolytic effect; preferably, the replication-selective recombinant oncolytic virus is derived from adenovirus, vaccinia virus, herpes simplex virus, measles virus, Semliki forest virus, vesicular stomatitis virus, polio virus, retrovirus, reovirus, Seneca valley virus, Echo-type enterovirus, Coxsackie virus, Newcastle disease virus and Malaba virus with oncolytic effect.

(39) The recombinant virus of (35), wherein the replication-selective recombinant oncolytic virus is a recombinant oncolytic adenovirus obtained by genetically modifying an adenovirus type 5, and E1B-55K gene and/or E1B-19K gene are deleted from the genome of the recombinant oncolytic adenovirus, and E1A gene coding sequence is comprised in the genome of the recombinant oncolytic adenovirus; preferably, the E1A gene coding sequence is under control of an exogenous promoter.

(40) The recombinant virus of (35) or (39), wherein the replication-selective recombinant oncolytic virus is a recombinant oncolytic adenovirus obtained by genetically modifying an adenovirus type 5, and E1A gene of the recombinant oncolytic adenovirus is modified so that the expressed E1A protein cannot bind to pRb protein; preferably, the E1A gene coding sequence is under control of an exogenous promoter.

(41) The recombinant virus of (39) or (40), wherein E3 gene of the replication-selective recombinant oncolytic virus is completely or partially deleted.

(42) A kit of combinational drugs with synergistic effects for treatment of tumors and/or cancers, comprising:

a first container comprising the first composition of the therapeutic agent of any one of (1) to (24);

a second container comprising the second composition of the therapeutic agent of any one of (1) to (24), wherein the first container is separate from the second container; and instructions specifying the timing and routes of administration.

(43) Use of the nucleic acid of any one of (30) to (33) in preparation of a medication for treatment or prevention of tumors and/or cancers.

(44) Use of the recombinant expression vector of (34) in preparation of a medication for treatment or prevention of tumors and/or cancers.

(45) Use of the recombinant virus of any one of (35) to (41) in preparation of a medication for treatment or prevention of tumors and/or cancers.

(46) Use of the kit of (42) in preparation of a medication for treatment or prevention of tumors and/or cancers.

(47) Use of any one of (43) to (46), wherein the tumors and/or cancers include: breast cancer, head and neck tumor, synovial cancer, kidney cancer, connective tissue cancer, melanoma, lung cancer, esophageal cancer, colon cancer, rectal cancer, brain cancer, liver cancer, bone cancer, choriocarcinoma, gastrinoma, pheochromocytoma, prolactinoma, von Hippel-Lindau disease, Zollinger-Ellison syndrome, anal cancer, cholangiocarcinoma, bladder cancer, ureteral carcinoma, glioma, neuroblastoma, meningioma, spinal cord tumor, osteochondroma, chondrosarcoma, Ewing's sarcoma, cancer of unknown primary site, carcinoid, fibrosarcoma, Paget's disease, cervix carcinoma, gallbladder cancer, eye cancer, Kaposi's sarcoma, prostate cancer, testicular cancer, cutaneous squamous cell carcinoma, mesothelioma, multiple myeloma, ovarian cancer, pancreatic endocrine tumor, glucagon tumor, pancreatic cancer, penile cancer, pituitary cancer, soft tissue sarcoma, retinoblastoma, small bowel cancer, gastric cancer, thymic cancer, trophoblastic carcinoma, hydatidiform mole, endometrial cancer, vaginal cancer, vulvar cancer, mycosis fungoides, insulinoma, heart cancer, meningeal cancer, blood cancer, peritoneal cancer and pleural cancer.

(48) A method for treating a tumor and/or cancer, comprising:

administering the first composition of the therapeutic agent of any one of (1) to (24) to a patient suffering from tumor and/or cancer; and administering the second composition of the therapeutic agent of any one of (1) to (24) to the patient suffering from tumor and/or cancer.

(49) The method of (48), comprising the following steps in a sequential manner:

1) administering the first composition to the patient suffering from tumor and/or cancer; and 2) administering the second composition of the therapeutic agent to the patient suffering from tumor and/or cancer after the administration of the first composition.

(50) The method of (48), wherein the tumor and/or cancer include: breast cancer, head and neck tumor, synovial cancer, kidney cancer, connective tissue cancer, melanoma, lung cancer, esophageal cancer, colon cancer, rectal cancer, brain cancer, liver cancer, bone cancer, choriocarcinoma, gastrinoma, pheochromocytoma, prolactinoma, von Hippel-Lindau disease, Zollinger-Ellison syndrome, anal cancer, cholangiocarcinoma, bladder cancer, ureteral carcinoma, glioma, neuroblastoma, meningioma, spinal cord tumor, osteochondroma, chondrosarcoma, Ewing's sarcoma, cancer of unknown primary site, carcinoid, fibrosarcoma, Paget's disease, cervix carcinoma, gallbladder cancer, eye cancer, Kaposi's sarcoma, prostate cancer, testicular cancer, cutaneous squamous cell carcinoma, mesothelioma, multiple myeloma, ovarian cancer, pancreatic endocrine tumor, glucagon tumor, pancreatic cancer, penile cancer, pituitary cancer, soft tissue sarcoma, retinoblastoma, small bowel cancer, gastric cancer, thymic cancer, trophoblastic carcinoma, hydatidiform mole, endometrial cancer, vaginal cancer, vulvar cancer, mycosis fungoides, insulinoma, heart cancer, meningeal cancer, blood cancer, peritoneal cancer and pleural cancer.

Compared to the existing technology, the present invention has the following advantages and positive effects:

In order to improve an effect of TCR-modified immune cells in treatment of tumors and widen the applicable scope of TCR-modified immune cells in treatment of tumors, the present invention is proposed to express exogenous epitope peptides and/or exogenous MHC class I molecules in tumor cells, so as to significantly increase the number of epitope peptide/MHC class I molecule complexes on the surface of tumor cells, and to use TCR-modified immune cells specific to the epitope peptide for combined therapy. When oncolytic viruses are used as vectors to mediate the expression of exogenous epitope peptides and/or exogenous MHC class I molecules in tumor cells, the oncolytic viruses and the TCR-modified immune cells can also produce synergistic therapeutic effects in killing tumors.

Specifically, since the TCR-modified immune cells (especially TCR-modified T cells) recognize the epitope peptide/MHC class I molecular complex presented by the MHC class 1 antigen presentation pathway, the presentation of epitope peptides on the surface of tumor cells cannot be significantly enhanced when expressing exogenous antigens in tumor cells only through conventional exogenous gene expression methods, in particular when tumor cells often have defects in the MHC class I antigen presentation pathway. Thus, the present invention firstly designed a labeling polypeptide amino acid sequence comprising one or more epitope peptide amino acid sequences, and a nucleic acid with the coding sequence of the labeling polypeptide, so that after the nucleic acid transfected tumor cells and/or cancer cells, or after inserting the nucleic acid into the viral genome and infecting tumor cells and/or cancer cells with the resulting recombinant virus, the labeling epitope polypeptide chain can be expressed in the cell and introduced into endoplasmic reticulum (ER) through the amino terminal signal peptide, and then cut/processed into the desired epitope polypeptide fragments, which can be finally presented on the surface of tumor cells and/or cancer cells by MHC class I molecules, so as to achieve an effect of significantly enhancing the presentation of epitope peptides on the surface of tumor cells, and effectively solve the problem of low antigen expression caused by the defect of the antigen presentation pathway caused by the tumor immune evasion mechanism. The present invention further inserted the HLA protein coding sequence into said nucleic acid to solve the problem of low expression or deletion of endogenous HLA protein. The present invention also proposed the combination of an active ingredient comprising or including a nucleic acid encoding the labeling polypeptide and a TCR-modified immune cell that recognizes epitope peptides, so as to improve recognition sensitivity of TCR-modified immune cells on tumor cells, thereby further enhancing the ability of TCR-modified immune cells to kill tumor cells.

Further, the present invention introduces the labeling polypeptide and/or HLA protein coding nucleic acid into tumor cells and/or cancer cells via oncolytic viruses, so that the synergistic therapeutic effect achieved by combination of presentation of foreign epitope peptides on the surface of tumor cells with immune cells modified by T cell receptors is further enhanced while exerting the function of killing tumor cells and/or cancer cells via oncolytic viruses. In addition, the oncolytic viruses can alleviate the immunosuppressive state of the tumor microenvironment while killing tumors, and improve homing of immune cells modified by T cell receptors; Furthermore, TCR-modified immune cells can also effectively eliminate those tumor cells that cannot complete the replication cycle and produce a sufficient number of progeny viruses and thus cannot be lysed upon infection by an oncolytic virus, thereby achieving further synergistic effect. In addition, the antigens released by the tumor cells lysed by the oncolytic virus can further activate the body's own anti-tumor immunity, which can achieve better tumor killing effects than the oncolytic viruses or TCR-modified immune cells alone, and achieve synergistic therapeutic effect.

The present invention provides a novel approach to treat tumors.

Definitions

As used herein, the terms "tumor", "cancer", "tumor cell" and "cancer cell" cover the meanings generally recognized in the art.

As used herein, the term "oncolytic virus" refers to a virus that can replicate selectively in and lyse tumor cells.

As used herein, the term "therapeutically effective amount" or "therapeutically effective dose" refers to an amount of a functional agent or of a pharmaceutical composition useful for exhibiting a detectable therapeutic or inhibitory effect or invoking an antitumor response. The effect can be detected by any assay method known in the art.

As used herein, the term "administer" or "administration" refers to providing a compound, a composite or a composition (including viruses and cells) to a subject.

As used herein, the term "patient" refers to a human or non-human organism. Thus, the methods and compositions described herein are applicable to both human and veterinary diseases. In certain embodiments, the patient has a tumor. In some cases, the patient may suffer from one or more types of cancer simultaneously.

As used herein, the term "synergistic effect" refers to an effect arising between two or more agents that produce an effect greater than the sum of their individual effects.

As used herein, the term "pfu", or "plaque forming unit" refers to the number of viruses forming a plaque.

As used herein, the term "VP" refers to number of viral particles.

As used herein, the term "VP/kg" refers to number of viral particles per kilogram of patient's body weight.

As used herein, the term "TCID50" stands for median tissue culture infective dose and refers to the viral dose that leads to infection and causes a cytopathic effect in 50% of the tissue culture.

As used herein, the term "MOI", or "multiplicity of infection" refers to the ratio between the number of viruses and the number of cells, i.e., the number of virus particles used to initiate viral infection per cell. MOI=pfu/cell, that is, the number of cells×MOI=Total PFU.

BRIEF DESCRIPTION OF THE DRAWINGS

FIG. 1A shows the results of flow cytometric analysis of PBMCs stained with CD8-APC antibody and Her2-E75 pentamer-PE after two cycles of Her2-E75 antigen polypeptide stimulation in vitro. The right panel shows the cells stimulated by the polypeptide. FACS sorting was performed on the CD8$^+$ pentamer$^+$ cytotoxic T cell population to obtain T cell clones. The left panel shows the control cells without peptide stimulation. The abscissa represents fluorescence intensity of the CD8 molecule expression, and the ordinate represents the fluorescence intensity of the bound Her2-E75 pentamer. FIG. 11B shows flow cytometric phenotype analysis of CD8+ E75-tetramer+ cytotoxic T lymphocyte clones after CD8-APC and Her2-E75 tetramer-PE staining. The right panel shows CD8+ Her2 tetramer+ T cell clone Her2 CTL 6A5 is a purified Her2-E75 polypeptide specific CTL cell clone. The left panel shows the control CTL cells without polypeptide stimulation. The abscissa represents the fluorescence intensity of the CD8 molecule expression, and the ordinate represents the fluorescence intensity of the bound Her2-E75 tetramer. FIG. 1C shows main functional fragments of the constructed lentiviral vector carrying the Her2 TCR-6A5-mC gene (i.e., "pCDH-EF1α-Her2 TCR vector"). The fragments as shown express the TCR gene driven by the EF-1α promoter. The constant region fragments of the β and α chains of each TCR are murine constant region fragments, and the β chain and α chain of the TCR are linked by a coding sequence (furin-F2A) of the cleavable linker polypeptide.

FIG. 2A shows the results of flow cytometric analysis after transfection of PBMCs from two different donors with a lentiviral vector encoding Her2 TCR-6A5-mC, and stained with Her2-E75 tetramer-PE and anti-CD8-APC antibody. Firstly, the lymphocyte population is divided according to the cell morphology and size. The Her2-E75 tetramer+ cell population is the cells expressing Her2 TCR-6A5-mC TCR. The abscissa represents the fluorescence intensity of CD8 molecule expression, and the ordinate represents the fluorescence intensity of the bound Her2-E75 tetramer. The percentage shown is a ratio of the number of each positive cell population to the number of divided lymphocytes. The left panel relates to peripheral blood monocyte cells provided by one donor (#1 PBMC), and right panel relates to PBMCs provided by different donor (#2 PBMC). CD8+ Her2-E75 tetramer+ cells are cytotoxic T cells expressing Her2 TCR-6A5-mC. CD8− Her2-E75 tetramer+ cells may be CD4+ helper T cells expressing Her2 TCR-6A5-mC. FIG. 2B shows that T cells expressing Her2 TCR-6A5-mC can recognize the Her2-E75 polypeptide presented by T2 cells. Two different donor PBMCs transfected with a lentiviral vector encoding Her2 TCR-6A5-mC were mixed and cultured with T2 cells presenting different concentration gradients of Her2-E75 polypeptide for 16 hours, and the cell supernatant was taken for IFN-γ ELISA analysis. The target cells in the control group are T2 cells presenting the EBV virus antigen polypeptide LMP2 426-434 that can bind to HLA-A2 molecules (not shown in the figure). In the figure, "0.1 μg/ml" represents the T2 cell group presenting 0.1 μg/ml of Her2-E75 polypeptide, and "0.01 μg/ml" represents T2 cells group presenting 0.01 μg/ml of Her2-E75 polypeptide, "0.001 μg/ml" represents T2 cell group presenting 0.001 μg/ml of Her2-E75 polypeptide, "0.0001 μg/ml" represents T2 cell presenting 0.0001 μg/ml of Her2-E75 polypeptide group. The ordinate represents the concentration of IFN-γ secreted by T cells. FIG. 2C shows the results of the CD8 antibody blocking test of T cell function. Among them, #2 PBMC transfected with the lentiviral vector encoding Her2 TCR-6A5-mC and the Her2-E75 antigen polypeptide presented by T2 cells were co-cultured with anti-human CD8 antibody to detect whether the function of T cells in secreting IFN-γ is inhibited. In the figure, "T2+Her2-E75" represents the T2 cell group without anti-human CD8 antibody and presenting 0.1 μg/ml of Her2-E75 polypeptide, "T2+Her2-E75+anti-CD8" represents T2 cell group with anti-human CD8 antibody and presenting 0.1 μg/ml of Her2-E75 polypeptide. The abscissa represents different experimental groups, and the ordinate represents the concentration of IFN-γ secreted by T cells. "Ns" means that there is no significant difference between the two experimental groups. Each experimental group and control group in FIGS. 2B and 2C was performed in multiple wells, and the results are shown as mean±SEM.

FIG. 3A shows the expression level of HLA-A2 and Her2/neu in different tumor cell strains. The abscissa represents different human tumor cell strains. "Colo205" and "HCT116" are colon cancer cells; "MDA-MB-231" and "MCF-7" are breast cancer cells; "PANC-1" is pancreatic cancer cells; "U87MG" is glioma cells; "NCI-H446" is lung cancer cells. The ordinate "MFI" represents the average fluorescence intensity of cells stained with anti-HLA-A2 fluorescent antibody or anti-Her2/neu fluorescent antibody. The white bars are the expression level of Her2/neu on the cell surface, and the black bars are the expression level of HLA-A2 on the cell surface. FIG. 3B shows the IFN-γ ELISA analysis results, wherein #2 PBMCs transfected with a lentiviral vector encoding Her2 TCR-6A5-mC TCR genes, were mixed and cultured with cells of different tumor cell strains for 24 hours, and then the cell supernatant was taken for IFN-γ ELISA analysis. Each experimental group and control group were performed in three wells, and the results are shown as mean±SEM. The abscissa shows different target cells, and the ordinate shows the concentration of IFN-γ secreted by T cells. The ratio of effector cells to target cells (E:T) is 5:1. White bars indicate that the effector cells are control peripheral blood monocyte cells not transfected with the Her2 TCR-6A5-mC TCR genes, and black bars indicate that the effector cells are peripheral blood monocyte cells transfected with the Her2 TCR-6A5-mC TCR genes. FIGS. 3C, D, E, F, G, H, I, J, and K show killing activity of #2 PBMCs on different tumor cell strains after transfection with the lentiviral vector encoding Her2 TCR-6A5-mC TCR genes. The killing activity of FIGS. 3C-3G was obtained by counting viable cells and the killing activity of FIGS. 3H-3K was determined by MTT method, in which the reaction time was 24 hours. Among them, FIGS. 3C and 3H show the results against the tumor cell line MCF-7, FIG. 3D shows the results against the tumor cell line HCT116, FIG. 3E shows the results against the tumor cell line U87MG, and FIG. 3F shows the results against the tumor cell line NCI-H446, FIG. 3G shows the results against the tumor cell line SKOV3, FIG. 3I shows the results against the tumor cell line PANC-1, FIG. 3J shows the results against the tumor cell line HEPG2, and FIG. 3K shows the results against the tumor cell line HT-29. Each experimental group and control group were performed in three wells, and the results are shown as mean±SEM. The abscissa shows the different ratios of effector cells to target cells E:T. The ordinate shows a percentage value of the killing rate of T cells to target cells. The dot-shaped diagram indicates that the effector cells are control peripheral blood monocyte cells that have not been transfected with the Her2 TCR-6A5-mC TCR genes, and the upper triangle diagram indicates that the effector cells are peripheral blood monocyte cells that have been transfected with the Her2 TCR-6A5-mC TCR genes. In the MTT killing experiment, another group was added with 10 μM of paclitaxel as a positive control (shown as a separate lower triangle point in FIGS. 3H-3K).

FIG. 4A shows that after HLA-A2-negative Her2/neu-negative 293T cells were transfected with a lentiviral plasmid vector capable of expressing HLA-A2 gene and Her2-E75 minigene (without KDEL at the C-terminal), it can activate PBMCs transfected by Her2 TCR-6A5-mC TCR. Each experimental group and control group were performed in duplicate wells, and the results are shown as mean±SME. The abscissa shows 293 T cells as target cells were transfected with different gene vectors. The ordinate represents the concentration of IFN-γ secreted by T cells. The E:T ratio is 10:1. The upper panel of FIG. 4B shows the main functional fragments of the constructed lentiviral vector (i.e., "pCDH-EF1p-A2-PKGp-E75 vector") carrying the HLA-A2 and Her2-E75 minigene (without KDEL at the C-terminal). The fragment as shown expresses the HLA-A2 gene driven by the EF-1α promoter and the Her2-E75 minigene driven by the PKG promoter (without KDEL at the C terminal). The bottom panel of FIG. 4B shows the constitution of the Her2-E75 minigene (without KDEL at the C-terminus), which consists of INSL5 signal peptide, eight Her2-E75 epitope peptide coding sequences and the furin digestion fragment between them. FIG. 4D shows the main functional fragments of the constructed recombinant adenoviral vector (i.e., "Adeasy-A2E75 vector") carrying the HLA-A2 gene and Her2-E75 minigene (with KDEL at the C terminal). The adenovirus is an adenovirus type 5 with deletion of E1 gene and E3 gene in the genome. The expression elements composed of HLA-A2 gene and Her2-E75 minigene driven by a CMV promoter and the Furin-F2A linker fragment between them were inserted in the E1 region. The Her2-E75 minigene is composed of INSL5 signal peptide, eight Her2-E75 epitope peptide coding sequences and the furin digestion fragments between them, and the carboxy-terminal endoplasmic reticulum (ER) retention signal peptide KDEL. FIG. 4C shows that HLA-A2 negative cells SKOV3 can express HLA-A2 after transfected with the vector carrying HLA-A2 gene and Her2-E75 minigene (KDEL at the C terminal) shown in FIG. 4D. The abscissa shows that SKOV3 cells were transfected with the different recombinant adenoviruses. "Adeasy-A2E75" is an adenovirus expressing HLA-A2 and Her2-E75 polypeptides; "Ad control" is a control adenovirus that does not carry HLA-A2 gene and Her2-E75 minigene. The ordinate "HLA-A2+(MFI)" indicates the average fluorescence intensity of cells stained with anti-HLA-A2 fluorescent antibody. "MOI" is the multiplicity of infection of virus.

FIG. 5A shows that T cells expressing Her2 TCR-6A5-mC TCR can be activated by different tumor cell strains infected with adenovirus carrying HLA-A2 gene and Her2 E75 minigene, and secrete IFN-γ. The effector cells are peripheral blood monocyte cells infected with replication-defective lentivirus carrying the Her2 TCR-6A5-mC TCR gene. The target cells are HLA-A2-negative Her/neu-positive ovarian cancer cells SKOV3, HLA-A2-positive Her2/neu-positive breast cancer cells MCF-7, and HLA-A2-negative Her2/neu-negative small cell lung cancer cells NCI-H446. The abscissa shows that different tumor cell strains as target cells are subjected to the different treatments. "Adeasy-A2E75" is target cells infected with replication-defective adenovirus carrying HLA-A2 gene and Her2 E75 minigene alone; "PBMC control" is a mixed culture of target cells and control peripheral blood monocyte cells that have not been transfected with the Her2 TCR-6A5-mC TCR gene; "PBMC control+Adeasy-A2E75" is a mixed culture of target cells after infected with replication defective adenovirus carrying HLA-A2 gene and Her2 E75 minigene for 24 hours and control peripheral blood monocyte cells that have not been transfected with the Her2 TCR-6A5-mC TCR gene; "PBMC with Her2 TCR-6A5" is a mixed culture of target cells and the peripheral blood monocyte cells transfected with the Her2 TCR-6A5-mC TCR gene; "PBMC with Her2 TCR-6A5+Adeasy-A2E75" is a mixed culture of the target cells after infected with replication-defective adenovirus carrying HLA-A2 gene and Her2 E75 minigene for 24 hours and the peripheral blood monocyte cells transfected with Her2 TCR-6A5-mC TCR gene. The ordinate shows the concentration of IFN-γ secreted by T cells. The E:T ratio is 5:1, and the multiplicity of infection of the adenovirus is MOI=10. "**" shows that when compared with the group using the replication-defective adenovirus expressing HLA-A2 and Her2 E75 polypeptide alone, or compared with the group using the peripheral blood monocyte cells expressing Her2 TCR-6A5-mC TCR alone, the combination group using both shows that the replication-defective adenovirus expressing HLA-A2 and Her2 E75 polypeptides can significantly increase the recognition activity of peripheral blood monocyte cells expressing Her2 TCR-6A5-mC TCR to different target cells (p<=0.0001), regardless of whether the target cells themselves express HLA-A2 and Her2/neu antigens. Each experimental group and control group were performed in three wells, and the results are shown as mean±SME. FIG. 5B shows that T cells expressing Her2 TCR-6A5-mC TCR can specifically kill tumor cell strains infected with adenovirus carrying HLA-A2 gene and Her2 E75 minigene. The abscissa shows that different tumor cell strains as target cells are subjected to different treatments, which is the same as the group shown on the abscissa of FIG. 5A. The E:T ratio is 8:1, and the multiplicity of infection of the adenovirus is MOI=10. The ordinate shows the killing rate of T cells to target cells, the killing rate (Cytotoxicity) %=((the number of viable cells of the initial target cells−the number of viable cells of the target cells at the end of culture)/the number of viable cells of the initial target cells)×100. "*" and "" show that when compared with the group using the replication-defective adenovirus expressing HLA-A2 and Her2 E75 polypeptides alone, or compared with the group using the peripheral blood monocyte cells expressing Her2 TCR-6A5-mC TCR alone, the combination group using both shows that the peripheral blood monocyte cells expressing Her2 TCR-6A5-mC TCR have significant specific killing ability to target cells infected with adenovirus expressing HLA-A2 and Her2 E75 polypeptides. "*" indicates p<=0.001, and "**" indicates p<=0.01. Each experimental group and control group were performed in three wells, and the results are shown as mean±SME.

FIG. 6A shows that T cells expressing Her2 TCR-6A5-mC TCR can be activated by tumor cell strains that are infected with oncolytic adenovirus carrying Her2-E75 minigene and express HLA-A2, and secrete IFN-γ. The effector cells are peripheral blood monocyte cells infected with the lentivirus carrying the Her2 TCR-6A5-mC TCR gene. The target cells were HLA-A2-negative Her2/neu-positive ovarian cancer cells SKOV3, HLA-A2-positive Her2/neu-positive breast cancer cells MCF-7, and HLA-A2-negative Her2/neu-negative small cell lung cancer cells NCI-H446. The abscissa shows that different tumor cell strains as target cells are subjected to different treatments. "Ad-E75" are target cells infected with the oncolytic adenovirus carrying the Her2-E75 minigene alone; "PBMC control" is a mixed culture of the target cells and the control peripheral blood monocyte cells that have not been transfected with the Her2 TCR-6A5-mC TCR gene; "PBMC control+Ad-E75" is a mixed culture of the target cells after infected with oncolytic adenovirus carrying Her2-E75 minigene for 24 hours and the control peripheral blood monocyte cells that have not been transfected with Her2 TCR-6A5-mC TCR gene; "PBMC with Her2 TCR-6A5" is a mixed culture of the target cells and the peripheral blood monocyte cells transfected with the Her2 TCR-6A5-mC TCR gene; "PBMC with Her2 TCR-6A5+Ad-E75" is a mixed culture of the target cells after infected with the oncolytic adenovirus carrying the Her2-E75 minigene for 24 hours and the peripheral blood monocyte cells transfected with the Her2 TCR-6A5-mC TCR gene. The ordinate shows the concentration of IFN-γ secreted by T cells. The E:T ratio is 5:1, and the multiplicity of infection of the adenovirus is MOI=10. "" shows that when compared with the group using the oncolytic adenovirus expressing Her2-E75 polypeptide alone, or compared with the group using the peripheral blood monocyte cells expressing Her2 TCR-6A5-mC TCR alone, the combination group using both indicates that the oncolytic adenovirus expressing Her2-E75 polypeptide can significantly increase the recognition activity of the peripheral blood monocyte cells expressing Her2 TCR-6A5-mC TCR to HLA-A2 expressing target cells ($p<=0.01$), wherein the target cells themselves mainly express HLA-A2 antigen. Each experimental group and control group were performed in three wells, and the results are shown as mean±SME. FIG. 6B shows that T cells expressing Her2 TCR-6A5-mC TCR can specifically kill tumor cell strains infected with oncolytic adenovirus carrying Her2-E75 minigene. The abscissa shows that different tumor cell strains as target cells are subjected to different treatments, which is the same as the group shown on the abscissa of FIG. 6A. The ordinate shows the killing rate of T cells to target cells, and the killing rate (Cytotoxicity) %=((the number of viable cells of the initial target cells−the number of viable cells of the target cells at the end of culture)/the number of viable cells of the initial target cells)×100. The E:T ratio is 5:1, and the multiplicity of infection of the adenovirus is MOI=10. "" and "*" show that when compared with the group using oncolytic adenovirus expressing Her2-E75 polypeptide alone, or compared with the group using peripheral blood monocyte cells expressing Her2 TCR-6A5-mC TCR alone, the combination group using both shows that the peripheral blood monocyte cells expressing Her2 TCR-6A5-mC TCR have significant specific killing ability to target cells infected with oncolytic adenovirus expressing Her2-E75 polypeptide. "" indicates $p<=0.01$, "***" indicates $p<=0.001$. Each experimental group and control group were performed in three wells, and the results are shown as mean±SME.

FIGS. 7A and 7B are the same experimental reaction. FIG. 7A is a factor level detection of the supernatant, and FIG. 7B is cell-related kill count detection. FIG. 7A shows that T cells expressing Her2 TCR-6A5-mC TCR can be activated by tumor cell strains that are infected with replication-defective adenoviruses carrying HLA-A2 gene and Her2-E75 minigene and express HLA-A2, and secrete IFN-γ. The effector cells are peripheral blood monocyte cells infected with the lentivirus carrying the Her2 TCR-6A5-mC TCR gene. The target cells are HLA-A2 negative Her2/neu positive large cell lung cancer cells NCI-H460, HLA-A2 negative Her2/neu positive colon cancer cells HT-29, HLA-A2 positive Her2/neu negative glioma cells U87MG. The abscissa shows that different tumor cell strains as target cells are subjected to different treatments. "Adeasy-A2E75" is target cells infected with the oncolytic adenovirus carrying HLA-A2 gene and Her2-E75 minigene alone; "PBMC control" is a mixed culture of the target cells and the control peripheral blood monocyte cells that have not been transfected with the Her2 TCR-6A5-mC TCR gene; "PBMC control+Adeasy-A2E75" is a mixed culture of target cells after infected with adenovirus carrying HLA-A2 gene and Her2-E75 minigene for 24 hours and the control peripheral blood monocyte cells that have not been transfected with the Her2 TCR-6A5-mC TCR gene; "PBMC with Her2 TCR-6A5" is a mixed culture of the target cells and the peripheral blood monocyte cells transfected with Her2 TCR-6A5-mC TCR gene; "PBMC with Her2 TCR-6A5+Adeasy-A2E75" is a mixed culture of target cells after infected with replication-defective adenovirus carrying HLA-A2 gene and Her2-E75 minigene for 24 hours and the peripheral blood monocyte cells transfected with Her2 TCR-6A5-mC TCR gene. The ordinate shows the concentration of IFN-γ secreted by T cells. The E:T ratio is 10:1, and the multiplicity of infection of the adenovirus is MOI=10. "" shows that when compared with the group using the replication-defective adenovirus expressing HLA-A2 and Her2-E75 polypeptides alone, or compared with the group using the peripheral blood monocyte cells expressing Her2 TCR-6A5-mC TCR alone, the combination group using both shows that the replication-defective adenovirus expressing HLA-A2 and Her2-E75 polypeptides can significantly increase the recognition activity of peripheral blood monocyte cells expressing Her2 TCR-6A5-mC TCR to different target cells ($p<=0.01$), regardless of whether the target cells themselves express HLA-A2 and Her2/Neu antigens. Each experimental group and control group were performed in three wells, and the results are shown as mean±SME. FIG. 7B shows that T cells expressing Her2 TCR-6A5-mC TCR can specifically kill tumor cell strains infected with replication-defective adenovirus carrying HLA-A2 gene and Her2-E75 minigene. The abscissa shows that different tumor cell strains as target cells are subjected to different treatments. The ordinate shows the killing rate of T cells to target cells, the killing rate (Cytotoxicity) %=((the number of viable cells of the initial target cells−the number of viable cells of the target cells at the end of culture)/the number of viable cells of the initial target cells)×100. The E:T ratio is 10:1, and the multiplicity of infection of the adenovirus is MOI=10. "*", "**" and "*" show that when compared with the group using the replication-defective adenovirus expressing HLA-A2 and Her2-E75 polypeptide alone, or compared with the group using the peripheral blood monocyte cells expressing Her2 TCR-6A5-mC TCR alone, the combination group using both shows that the peripheral blood monocyte cells expressing Her2 TCR have significant specificity in killing the target cells infected with replication-defective adenovirus expressing HLA-A2 and Her2-E75 polypeptides. "*" indicates $p<=0.001$, "" indicates $p<=0.01$, and "*" indicates $p<=0.05$. Each experimental group and control group were performed in three wells, and the results are shown as mean±SME. FIG. 7C shows the flow cytometry results of cells. The abscissa shows the target cell group. The ordinate "HLA-A2+(MFI)" represents the average fluorescence intensity of cells stained with anti-HLA-A2 fluorescent antibody. After the tumor cells are infected with the oncolytic adenovirus Ad-E75A2 carrying Her2-E75 minigene and HLA-A2 gene and the replication-defective adenovirus Adeasy-A2E75 carrying HLA-A2 gene and Her2-E75 minigene, the expression of HLA-A2 in the tumor cells can be increased and the sensitivity thereof to TCR-T are also promoted.

FIG. 8A and FIG. 8B are the same experimental reaction, FIG. 8A is factor level detection of the supernatant, and FIG. 8B is cell-related kill count detection. FIG. 8A shows that the T cells expressing Her2 TCR-6A5-mC TCR can be activated by different tumor cell strains that are infected with oncolytic adenovirus carrying Her2-E75 minigene and HLA-A2 gene, and secrete IFN-γ. The effector cells are the peripheral blood monocyte cells infected with the lentivirus carrying the Her2 TCR-6A5-mC TCR gene. The target cells are HLA-A2 negative Her2/neu positive large cell lung cancer cells NCI-H460, HLA-A2 negative Her2/neu positive colon cancer cells HT-29, HLA-A2 positive Her2/neu negative glioma cells U87MG. The abscissa shows that different tumor cell strains as target cells are subjected to different treatments. "Ad-E75A2" are target cells infected with the oncolytic adenovirus carrying Her2-E75 minigene and HLA-A2 alone; "PBMC control" is a mixed culture of the target cells and the control peripheral blood monocyte cells that have not been transfected with the Her2 TCR-6A5-mC TCR gene; "PBMC control+Ad-E75A2" is a mixed culture of the target cells infected with oncolytic adenovirus carrying Her2-E75 minigene and HLA-A2 gene for 24 hours and the control peripheral blood monocyte cells that have not been transfected with Her2 TCR-6A5-mC TCR gene; "PBMC with Her2 TCR-6A5" is a mixed culture of the target cells and the peripheral blood monocyte cells transfected with Her2 TCR-6A5-mC TCR gene; "PBMC with Her2 TCR-6A5+Ad-E75A2" is a mixed culture of the target cells infected with oncolytic adenovirus carrying Her2-E75 minigene and HLA-A2 gene for 24 hours and the peripheral blood monocyte cells transfected with Her2 TCR-6A5-mC TCR gene. The ordinate shows the concentration of IFN-γ secreted by T cells. The E:T ratio is 10:1, and the multiplicity of infection of the adenovirus is MOI=10. "*" and "" show that when compared with the group using the oncolytic adenovirus expressing Her2-E75 polypeptide and HLA-A2 alone, or compared with the group using the peripheral blood monocyte cells expressing Her2 TCR-6A5-mC TCR alone, the combination group using both indicates that the oncolytic adenovirus expressing Her2-E75 polypeptide and HLA-A2 can significantly increase the recognition activity of the peripheral blood monocyte cells expressing Her2 TCR-6A5-mC TCR to different target cells, regardless of whether the target cells themselves express HLA-A2 and Her2/Neu antigens. "*" indicates $p \leq 0.001$, "**" indicates $p \leq 0.0001$. Each experimental group and control group were performed in three wells, and the results are shown as mean±SME. FIG. 8B shows that T cells expressing Her2 TCR-6A5-mC TCR can specifically kill tumor cell strains infected with the oncolytic adenovirus carrying Her2-E75 minigene and HLA-A2. The abscissa shows that the different tumor cell strains as target cells are subjected to different treatments. The ordinate shows the killing rate of T cells to target cells, the killing rate (Cytotoxicity) %=((the number of viable cells of the initial target cells–the number of viable cells of the target cells at the end of culture)/the number of viable cells of the initial target cells)×100. The E:T ratio E:T is 10:1, and the multiplicity of infection of the adenovirus is MOI=10. "" and "*" show that when compared with the group using the oncolytic adenovirus expressing Her2-E75 polypeptide and HLA-A2 alone, or the group using the peripheral blood monocyte cells expressing Her2 TCR-6A5-mC TCR alone, the combination group using both indicates that the peripheral blood monocyte cells expressing Her2 TCR-6A5-mC TCR have significant specific killing ability to the target cells infected with oncolytic adenoviruses expressing Her2-E75 polypeptide and HLA-A2. "**" indicates $p \leq 0.01$, "*" indicates $p \leq 0.05$. Each experimental group and control group were performed in three wells, and the results are shown as mean±SME.

In FIG. 11, the solid dots indicate initiating time of subcutaneous inoculation of tumor cells in the animals, and the hollow dots indicate the grouping time for animal experiments.

16A shows the number of human CD3+ T cells per 20,000 tumor cells in the tumor tissues of the six groups of animals, and FIG. 16B shows the number of human CD8+ T cells per 20,000 tumor cells in the tumor tissues of the six groups of animals, and FIG. 16C shows the number of human CD4+ T cells per 20,000 tumor cells in the tumor tissues of six groups of animals. The abscissa in each figure represents the different groups in the experiments, and the ordinate represents the number of T cells after normalization. Among them, normalization means that the immune cells infiltrated in the tumors of each group of animals are expressed according to the number of immune cells detected in every 20,000 tumor-derived cells.

DETAILED DESCRIPTION OF THE PREFERRED EMBODIMENTS

Figure 1:
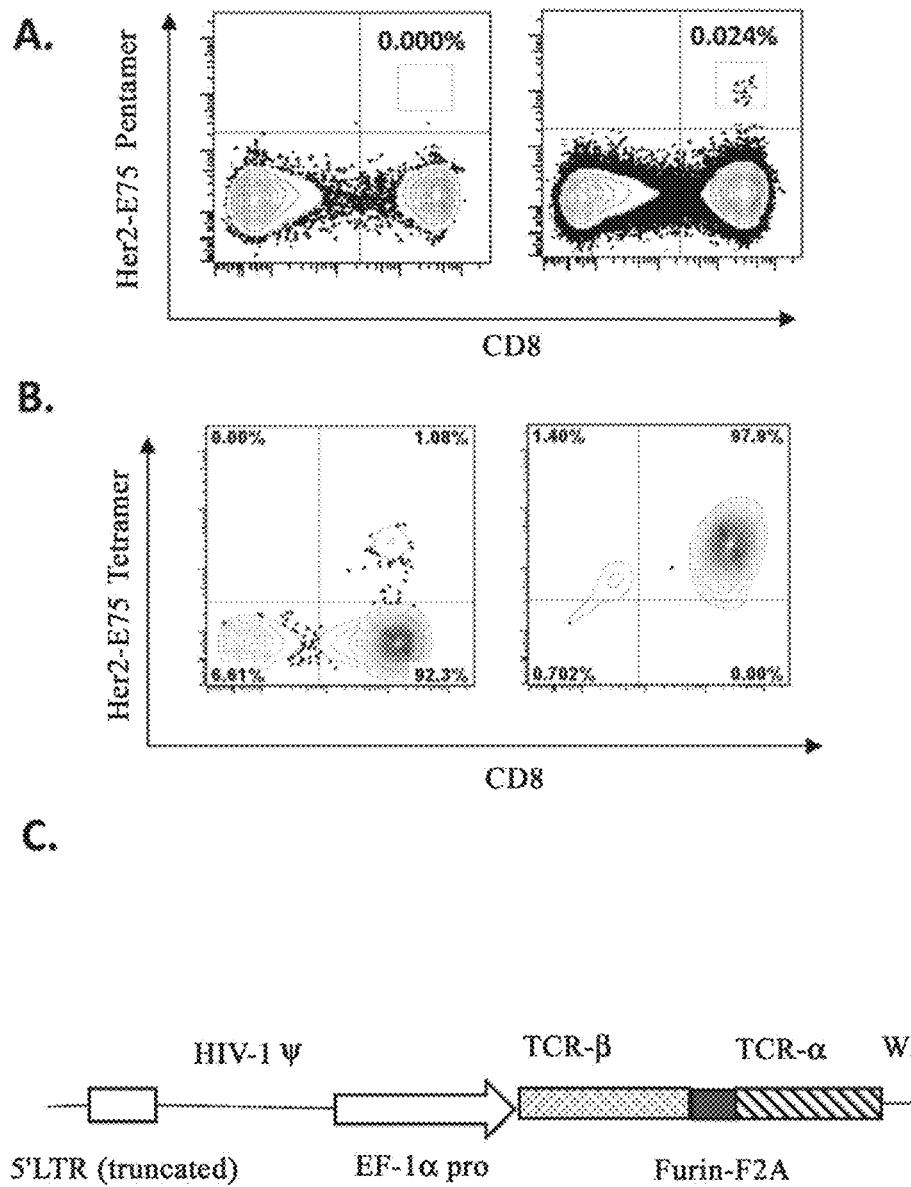
FIG. 1 shows the phenotype and functional detection results of Her2/neu 369-377 polypeptide (Her2-E75) specific cytotoxic T cells induced from HLA-A2$^+$ normal donor PBMCs (specifically #1 PBMC) in Example 1 of the present invention.

The present disclosure is further explained with the following detailed description of preferred embodiments with references to the accompanying drawings, which is not to be taken in a limiting sense, and it will be apparent to those skilled in the art that various modifications or improvements can be made accordingly without departing from the spirit of the present disclosure and these are therefore within the scope of the present disclosure.

In view of the problems and difficulties of the adoptive immune cell therapy and oncolytic virus treatment of tumors, the inventors of the present invention, through theoretical research and experimental verification, proposed a concept of combined therapy, which is achieved by combing significantly enhanced presentation of exogenous epitope peptides on the surface of tumor cells with the TCR-modified immune cells specifically targeted the epitope peptides. Through this inventive concept, the present invention has effectively addressed the problems of low expression or deletion of endogenous HLA protein, which is resulted from defect of the antigen presentation pathway caused by the tumor immune evasion mechanism, and improves the recognition sensitivity of tumor cells against the TCR-modified immune cells, further enhancing the homing ability of and the ability in killing the tumor cells of the TCR-modified immune cells. In addition, the present invention also expands an applicable scope of adoptive immune cell therapy based on TCR gene modification in treating tumors, and avoids the limitation in a narrow applicable scope caused by HLA restrictions.

Specifically, the present invention provides a therapeutic agent for treatment of tumors and/or cancers, comprising:

(a) a first composition, wherein the first composition comprises a first active ingredient in a first pharmaceutically acceptable carrier, and the first active ingredient includes or contains a nucleic acid having a labeling polypeptide coding sequence for being introduced into a tumor cell and/or a cancer cell; the labeling polypeptide has one or more amino acid sequences of epitope polypeptide, the epitope polypeptides can be presented on the surface of the tumor cell and/or cancer cell by MHC class I molecules; and (b) a second composition, wherein the second composition comprises a second active ingredient in a second pharmaceutically acceptable carrier, and the second active ingredient comprises a TCR-modified immune cell; the TCR-modified immune cell can specifically recognize and bind to the epitope polypeptide presented by the MHC class I molecules.

Usually, the antigen protein expressed in the cytoplasm can enter the MHC class I antigen presentation pathway. After a series of protease hydrolysis, the formed short peptides (containing epitope polypeptide) are transduced into the endoplasmic reticulum through the TAP molecule on the endoplasmic reticulum membrane, and combine with HLA protein and $\beta_2$-microglobulin therein to form a trimer. Then, the trimer is presented on the cell surface (where HLA protein and $\beta_2$-microglobulin pair to form MHC class I molecules), which can be recognized by immune cells. Due to the lack in function of the MHC class I antigen presentation pathway in tumor cells, the tumor antigens expressed in the cytoplasm cannot effectively form epitope polypeptides or enter the endoplasmic reticulum and combine with HLA and $\beta_2$ microglobulin to form a complex.

In the present invention, by introducing the nucleic acids with the labeling polypeptide coding sequences into tumor cells and/or cancer cells, the exogenous labeling polypeptide expressed in the tumor cells and/or cancer cells can enter the MHC class I antigen presentation pathway. Therefore, the expression level of the HLA/epitope polypeptide complex on the surface of tumor cells is increased, thereby enhancing the recognition sensitivity of the TCR-modified immune cells to the tumor cells and/or cancer cells.

The amino acid sequence of the epitope polypeptide may be derived from the amino acid sequence of naturally occurring proteins, or an artificially synthesized amino acid sequence that does not exist in nature. Preferably, the naturally occurring proteins include human-derived proteins and proteins of species other than human. More preferably, the amino acid sequence of the epitope polypeptide is derived from the amino acid sequences of a tumor-associated antigen or a tumor-specific antigen.

"Tumor-associated antigen" usually refers to a normal protein that is derived from oneself, but overexpressed or abnormally expressed in tumor cells, including carcinoembryonic antigen, tumor-testis antigen (CT antigen), etc.

"Tumor-specific antigen" usually refers to a mutant protein derived from oneself, or a foreign viral protein associated with tumorigenesis and development.

In the present invention, "tumor-associated antigen" and "tumor-specific antigen" are sometimes collectively referred to as "tumor antigen".

The tumor antigen may be a tumor antigen as described in Cancer Antigenic Peptide Database (website hypertext transfer protocol caped.icp.ucl.ac.be). Preferably, the tumor antigen may be a tumor antigen as shown in Table 1 below. It is also preferred that the tumor antigen may be human Her2/neu, NY-ESO-1, N-ras, K-ras, H3.3K27M, SSX-2, MAGE-C2, MAGE-A1, KK-LC-1. p53. The amino acid sequence of Her2/neu is as shown in SEQ ID NO:21.

The epitope polypeptide may be a peptide fragment with 8-11 amino acids that can be presented by MHC class I molecules. The epitope polypeptide may be an epitope polypeptide as described in Cancer Antigenic Peptide Database (website hyptertext transfer protocol caped.icp.ucl.ac.be). Preferably, the epitope polypeptide may be an epitope polypeptide as shown in Table 1 below. In other embodiments, the epitope polypeptide may be an epitope polypeptide having the 4-9 consecutive identical amino acids (for example, 4, 5, 6, 7, 8 or 9 consecutive identical amino acids) as the epitope polypeptide shown in Table 1 below, and the length of these polypeptides is 8-11 amino acids. It is also preferred that the epitope polypeptides include, but are not limited to, Her2/neu 369-377 as shown in SEQ ID NO: 3, Her2/neu 373-382 as shown in SEQ ID NO: 22, NY-ESO-1 157-165, NY-ESO-1 1-11, NY-ESO-1 53-62, NY-ESO-1 18-27, N-ras 55-64, K-ras 224-232, K-ras 10-18, K-ras 10-19, H3.3K27M 26-35, SSX-2 41-49, MAGE-C2 336-344, MAGE-C2 191-200, MAGE-C2 307-

315, MAGE-C2 42-50, MAGE-A1 120-129, MAGE-A1 230-238, MAGE-A1 161-169, KK-LC-1 76-84, p53 99-107, HPV16-E6 29-38, HPV16-E7 11-19, HPV16-E7 11-19, EBV-LMP1 51-59 and EBV-LMP1 125-133.

TABLE 1

Preferred tumor antigens and epitope polypeptides

| Names of Tumor antigens | HLA type | The sites of amino acid sequence |
|---|---|---|
| N-ras | A1 | 55-64 |
| MART2 | A1 | 446-455 |
| MATN | A11 | 226-234 |
| CDKN2A | A11 | 125-133 |
| CDK12 | A11 | 924-932 |
| k-ras | A2 | 224-232 |
| hsp70-2 | A2 | 286-295 |
| HAUS3 | A2 | 154-162 |
| GAS7 | A2 | 141-150 |
| CSNK1A1 | A2 | 26-34 |
| CLPP | A2 | 240-248 |
| CDK4 | A2 | 23-32 |
| a-actinin-4 | A2 | 118-127 |
| β-catenin | A24 | 29-37 |
| SIRT2 | A3 | 192-200 |
| GPNMB | A3 | 179-188 |
| EFTUD2 | A3 | 668-677 |
| MUM-3 | A68 | 322-330 |
| Elongation factor 2 | A68 | 581-589 |
| CASP-8 | B35 | 476-484 |
| SNRPD1 | B38 | 19-Oct |
| OS-9 | B44 | 438-446 |
| MUM-2 | B44 | 123-133 |
| MUM-1 | B44 | 30-38 |
| KIAAO205 | B44 | 262-270 |
| NFYC | B52 | 275-282 |
| RBAF600 | B7 | 329-337 |
| HSDL1 | Cw14 | 20-27 |
| MUM-2 | Cw6 | 126-134 |
| K-ras | Cw8 | (10-18) |
| K-ras | Cw8 | (10-19) |
| MAGE-A3 | A1 | 168-176 |
| MAGE-A1 | A1 | 161-169 |
| SSX-2 | A2 | 41-49 |
| NY-ESO-1/LAGE-2 | A2 | 157-165 |
| NY-ESO-1/LAGE-2 | A2 | (1-11) |
| MAGE-C2 | A2 | 336-344 |
| MAGE-C2 | A2 | 191-200 |
| MAGE-A10 | A2 | 254-262 |
| LAGE-1 | A2 | (1-11) |
| HERV-K-MEL | A2 | (1-9) |
| GAGE-3,4,5,6,7 | A29 | (10-18) |
| NY-ESO-1/LAGE-2 | A31 | 53-62 |
| NY-ESO-1/LAGE-2 | A31 | (18-27) |
| LAGE-1 | A31 | (18-27) |
| MAGE-A6 | A34 | 290-298 |
| KK-LC-1 | B15 | 76-84 |
| MAGE-A6 | B35 | 168-176 |
| MAGE-A6 | B37 | 127-136 |
| MAGE-A3 | B37 | 127-136 |
| MAGE-A2 | B37 | 127-136 |
| MAGE-A1 | B37 | 120-129 |
| MAGE-C2 | B44 | 307-315 |
| MAGE-C2 | B57 | 42-50 |
| MAGE-A6 | Cw16 | 293-301 |
| MAGE-A1 | Cw16 | 230-238 |
| BAGE-1 | Cw16 | (2-10) |
| GAGE-1,2,8 | Cw6 | (9-16) |
| MAGE-A12m | Cw7 | 170-178 |
| Tyrosinase | A1 | 243-251 |
| Tyrosinase | A1 | 146-156 |
| Tyrosinase | A2 | (1-9) |
| Tyrosinase | A2 | 369-377 |
| Melan-A/MART-1 | A2 | 32-40 |
| Melan-A/MART-1 | A2 | 26(27)-35 |
| Tyrosinase | A24 | 368-373 and 336-340e |
| Tyrosinase | A24 | 206-214 |
| Tyrosinase | A26 | 90-98 |
| TRP-2 | A31 | 197-205 |

TABLE 1-continued

Preferred tumor antigens and epitope polypeptides

| Names of Tumor antigens | HLA type | The sites of amino acid sequence |
|---|---|---|
| TRP-2 | A33 | 197-205 |
| Tyrosinase | B35 | 312-320 |
| Tyrosinase | B35 | 309-320 |
| Melan-A/MART-1 | B35 | 26-35 |
| Tyrosinase | B38 | 388-397 |
| Tyrosinase | B44 | 192-200 |
| Melan-A/MART-1 | B45 | 24-33(34) |
| TRP-2 | Cw8 | 387-395 |
| MMP-2 | A2 | 560-568 |
| HER-2/neu | A2 | 369-377 |
| CPSF | A2 | 1360-1369 |
| CPSF | A2 | 250-258 |
| CALCA | A2 | 16-25 |
| PRAME | A24 | 301-309 |
| FGF5 | A3 | 172-176 and 217-220 |
| p53 | B46 | 99-107 |
| PBF | B55 | 499-510 |
| H3.3K27M | A2 | 26-35 |
| HPV16-E6 | | 29-38 |
| HPV16-E7 | | 11-19 |
| HPV16-E7 | | 11-19 |
| EBV-LMP1 | | 51-59 |
| EBV-LMP1 | | 125-133 |

In certain embodiments, each of the epitope polypeptides has flexible linker fragments at both ends, which function as digestion sites for proteolytic enzymes in the cytoplasm to release the epitope polypeptide. The flexible linker fragments include GSGSR, AGSGSR and AGSGS.

In certain embodiments, the labeling polypeptide has a signal peptide that can introduce the labeling polypeptide into the endoplasmic reticulum at the amino terminus of the one or more amino acid sequence of the epitope polypeptide. The core of the signal peptide comprises a long fragment of hydrophobic amino acids, which forms a single helix. The amino terminus of the signal peptide usually starts with a short positively charged amino acid sequence, and there is usually an amino acid cleavage site at the end of the signal peptide that is recognized and cleaved by signal peptidase. After the connected exogenous polypeptide enters the endoplasmic reticulum, the signal peptide is recognized and cleaved by signal peptidase, and the exogenous polypeptide is released in the endoplasmic reticulum. Therefore, the labeling polypeptides carrying signal peptides can directly enter the endoplasmic reticulum without protease hydrolysis in the MHC class I antigen presentation pathway and the transport of TAP molecules. The signal peptide may be a signal peptide (SEQ ID NO: 28) composed of amino acids at position 1 to 22 from an amino terminal of insulin-like protein (INSL5).

In the case where the labeling polypeptide has a plurality of the epitope polypeptides, every two of the epitope polypeptides may be connected by a cleavable linker polypeptide. The cleavable linker polypeptide includes furin cleavage recognition polypeptide, which has a standard four-amino acid motif that can be cleaved by Furin enzyme, that is, the RX—[KR]—R amino acid sequence (see "Molecular Therapy 2007; vol. 15 no. 6, 1153-1159"). Preferably, the amino acid sequence of the cleavable linker polypeptide is R—R—K—R. After the labeling polypeptide is introduced into the endoplasmic reticulum by the above-mentioned signal peptide, the epitope polypeptide connected by the RX—[KR]—R amino acid sequence is cleaved and hydrolyzed by furin enzyme in the endoplasmic reticulum to release the epitope polypeptide, and then the epitope polypeptide binds to HLA and β₂-microglobulin in the endoplasmic reticulum to form an antigen complex. The aminopeptidase and carboxypeptidase in the endoplasmic reticulum may also be involved in the enzymatic hydrolysis and release of epitope polypeptide (see "J Immunol. 2009 Nov. 1; 183(9): 5526-5536"). Therefore, the cleavable linker polypeptide may also include aminopeptidase and carboxypeptidase digestion recognition polypeptide.

In order to enable the labeling polypeptide introduced into the endoplasmic reticulum by the signal peptide to be retained in the endoplasmic reticulum cavity to facilitate release of the epitope polypeptide and bind to HLA and β2 microglobulin to form an antigen complex, in some embodiments, the labeling polypeptide has an endoplasmic reticulum retention signal peptide at the carboxylic terminal of one or more amino acid sequence of the epitope polypeptide. The amino acid sequence of the endoplasmic reticulum retention signal of the soluble polypeptide (i.e., non-transmembrane protein) is KDEL, and the ER retention signal of the ER membrane protein is KKXX (see "Molecular Biology of the Cell. 2003; 14 (3): 889-902"). In the present invention, said labeling polypeptide is a soluble polypeptide. Therefore, it is preferable that the endoplasmic reticulum retention signal peptide is a K-D-E-L fragment composed of lysine-aspartic acid-glutamic acid-leucine residues.

In a specific embodiment, the labeling polypeptide includes the following amino acid sequences that are operatively linked in an orderly tandem fashion: the amino acid sequence of the N-terminal signal peptide, one or more amino acid sequences of the epitope polypeptide, optional amino acid sequence of the C-terminal ER retention signal, wherein when the labeling polypeptide includes a plurality of amino acid sequences of the epitope polypeptides, one of the amino acid sequences of every two adjacent epitope polypeptides may be linked by the amino acid sequence of the cleavable linker polypeptide; the amino acid sequence of the epitope polypeptide and the optional C-terminal ER retention signal amino acid sequence may be linked by the amino acid sequence of the cleavable linker polypeptide. Preferably, the labeling polypeptide includes the amino acid sequence of the C-terminal ER retention signal.

Preferably, the labeling polypeptide includes n of the epitope polypeptides (preferably Her2/neu 369-377 epitope polypeptides) linked by the cleavable linker polypeptide RRKR, wherein n is an integer greater than or equal to 1, For example, n=1, 2, 3, 4, 5, 6, 7, 8, 9, 10, 11, 12 . . . . Preferably, n is an integer between 1 and 20 (for example, an integer between 2 and 20); More preferably, n is an integer between 1 and 10 (for example, an integer between 2 and 10); Still more preferably, n=8.

Considering that tumor cells and/or HLA proteins in cancer cells often have expression defects, including complete deletions, haplotype deletions or allelic deletions and the range of deletions for different tumors ranges from 65% to 90% (see "Immunol Today. 1997; 18:89-95"), in one embodiment, the nucleic acids also have an HLA protein coding sequence, wherein the HLA protein coding sequence and the labeling polypeptide coding sequence are under control of their respective promoter, or the HLA protein coding sequence and the labeling polypeptide coding sequence are under control of the same promoter, and the HLA protein coding sequence may be operatively connected with the labeling polypeptide coding sequence by a cleavable linking polypeptide coding sequence. Preferably, the phenotype of the HLA protein is consistent with the phenotype of the HLA protein to which the labeling polypeptide can bind. The promoter may be a eukaryotic promoter, including a continuous expression promoter and an inducible expression promoter, including (for example): PGK1 promoter, EF-1α promoter, CMV promoter, SV40 promoter, Ubc promoter, CAG promoter, TRE promoter, CaMKIIa promoter, human β actin (human beta actin) promoter.

In this way, the present invention further increases the expression level of the MHC/epitope polypeptide complex on the surface of tumor cells, thereby enhancing the recognition sensitivity of the TCR-modified immune cells to tumor cells.

More specifically, the MHC protein is an HLA class I protein. More specifically, the HLA includes HLA-A, B, and C. Preferably, the HLA protein is HLA-A2 protein, and HLA-A2 has an amino acid sequence as shown in SEQ ID NO: 29.

Examples of the cleavable linker polypeptide connecting the HLA protein and the labeling polypeptide are known in the art, such as 2A polypeptides, which include but are not limited to, F2A polypeptides from Picornavirus, and similar 2A class polypeptides from other viruses; it may also be a Furin-F2A linker fragment.

Preferably, in the therapeutic agent of the present invention, the first composition and the second composition are present separately in the therapeutic agent without being mixed with each other.

Preferably, in the therapeutic agent of the present invention, the nucleic acids include DNA or RNA; the RNA includes mRNA transcribed from the DNA.

In one embodiment, the first active ingredient is a recombinant virus, and the genome of the recombinant virus has a labeling polypeptide coding sequence and an optional HLA protein coding sequence; wherein the recombinant virus includes a replication-selective recombinant oncolytic virus or a replication-defective recombinant virus.

The replication-defective recombinant virus is a viral vector lacking one or several essential functional genes related to virus replication, proliferation and virus particle assembly. The viral vector cannot replicate in normal cells to form progeny viruses, but can express the virus itself or foreign gene products. The replication-defective recombinant virus is preferably derived from adenovirus, adeno-associated virus (AAV), herpes simplex virus, vaccinia virus, influenza virus, alpha virus (Alphavirus), and Sendai virus.

Preferably, the replication-defective recombinant virus is a recombinant adenovirus obtained by genetically modifying an adenovirus type 5, wherein the E1 gene is deleted from the genome of the recombinant adenovirus, and the labeling polypeptide coding sequence and optional HLA protein coding sequence are inserted at a site of the deleted E1 gene.

The replication-selective recombinant oncolytic virus is derived from a genetically mutated virus with an oncolytic effect and a wild-type virus with an oncolytic effect. Preferably, the replication-selective recombinant oncolytic virus is derived from adenovirus, vaccinia virus, herpes simplex virus, measles virus, Semliki forest virus, vesicular stomatitis virus, polio virus, retrovirus, reovirus, Seneca valley virus, Echo-type enterovirus, Coxsackie virus, Newcastle disease virus and Malaba virus with the oncolytic effect.

After the oncolytic virus infects the tumor cells, it selectively replicates in the tumor cells, and the tumor cells are lysed through massive proliferation of the progeny viruses to achieve the effect of specifically killing the tumor cells. The released progeny viruses can further selectively infect and lyse other tumor cells to eliminate tumor tissue to the greatest extent (see "Nat Biotechnol. 2012 Jul. 10; 30(7):

658-70"). Abnormal RAS, TP53, RB1, PTEN, WNT and other signal transduction pathways in tumor cells affect the cell's own antiviral mechanism, making it easier for viruses to replicate in tumor cells, which is the main reason for tumor selectivity. Since a molecule mechanism of inhibiting virus replication in normal cells is complete, the oncolytic virus cannot replicate and spread effectively after infecting normal cells, which greatly limits damage to normal tissue cells (see "Nat Rev Cancer. 2017 11; 17(11):633"). Genetically engineering the viral genome further enhances the tumor selectivity of oncolytic viruses, and can carry functional foreign genes to enhance the anti-tumor activity of oncolytic viruses. In addition to oncolytic effect per se, the oncolytic viruses can also change the microenvironment of tumor tissues, mainly by inducing the secretion of cytokines, attracting natural immune cells, releasing tumor antigens, and providing immune danger signals, etc., thereby enhancing immune response of local tumor resistance (see "J. Clin. Invest. 2018; 128, 1258-1260"). Adenovirus as a vector is an oncolytic virus that was developed earlier. The Ad5 adenovirus H101 based on E1B-55K and E3 gene defects is the first oncolytic virus product approved for marketing (see "Hum Gene Ther. 2018 February; 29(2):151-159"). The molecule structure and biological characteristics of adenoviruses have been studied in depth, making it easier for adenoviruses to become oncolytic viruses through genetic engineering. Adenovirus has some characteristics, including: adenovirus genome may be modified to allow the insertion of larger fragments of foreign genes; adenovirus genome DNA will not integrate into the host genome; it will not cause malignant transformation of human cells; it can infect most of human tumors cells; and the ability to produce virus particles with stable high titer. These characteristics make adenovirus more suitable as an oncolytic virus vector (see "Curr Opin Virol. 2016 12; 21:9-15"). The different designs of oncolytic adenoviruses depend on different mechanisms of tumor selectivity thereof. For example, after the Ad5 adenoviruses with E1B-55K gene defects infect normal cells with p53 function, apoptosis is induced before the virus replication cycle is completed. About 50% of tumor cells that have lost p53 function due to genetic mutations will complete replication and lyse the cells (see "Nat Med 1998; 4(9):1098-72"). The oncolytic adenovirus partially deleted in E1A gene will also restrict its replication in normal cells. The defective protein (E1AΔ24) produced after 24 bases of CR2 region of E1A is removed will lose its function in release of E2F1 from E2F1/pRB complex. Free E2F1 is essential for initiating downstream replication. The pRB pathway in tumor cells is often abnormal, so a large amount of free E2F1 is produced to ensure the selective replication of the virus in tumor cells (see "Cell 2000; 100(1):57-70"). The tumor selectivity of the oncolytic adenoviruses carrying VA-RNA gene defects depends on activation of the RAS signaling pathway in tumor cells and the incomplete interferon pathway (see "Cancer Res. 2003; 63(17):5544-50"). Another tumor-selective mechanism of the oncolytic adenovirus is to use tumor-specific gene promoters to drive genes necessary for adenovirus replication. For example, an alpha-fetoprotein promoter in liver cancer cells (see "Hum Gene Ther. 1999; 10(10): 1721-33"); a prostate specific antigen (PSA) promoter in prostate cancer cells (see "Cancer Res. 1997; 57(13):2559-63"), or an osteocalcin (hOC) promoter (see "Cancer Res. 2002; 62(11): 3084-92"); or a DF3/MUC1 promoter in MUC-1 positive breast cancer (see "J Clin Invest. 2000; 106(6):763-71") and other promoters that are mainly activated in specific tumor cells can be used to drive the gene expression of E1A-deficient adenovirus E1A, in order to achieve selective replication in these tumor cells. If a promoter whose activity depends on the free E2F1 transcription factor, such as the E2F1 promoter that can bind to the palindrome of E2F1, is used to drive the expression of genes necessary for virus replication, it can only effectively express downstream molecules of viral replication in tumor cells rich in free E2F1 to achieve selective lysis of tumor cells (see "Mol Ther. 2007; 15(9): 1607-15"; "Cancer Cell. 2002; 1(4):325-37").

Although the genetically engineered oncolytic adenovirus enhances selective killing of tumor cells, the oncolytic ability of the virus must be further strengthened to improve its clinical efficacy. Since completion of the replication cycle of oncolytic viruses requires the cellular components of the host tumor cells and specific molecular mechanisms, and the diversity of tumors determines that when tumor cells having different growth states and properties are infected by oncolytic viruses, in some tumor cells, the replication cycle cannot be completed and the number of progeny viruses cannot be produced enough to lysis the cell. In addition, when the E1B-55K is deleted in the oncolytic adenovirus, it may cause obstacles in the process of exporting the mRNA encoding late viral proteins from the nucleus to the cytoplasm for protein translation, thereby affecting the replication of the virus in tumor cells (see "Viruses. 2015 November; 7(11): 5767-5779"). These factors will limit the clinical efficacy of oncolytic viruses when used alone.

In one embodiment of the present invention, the nucleic acids containing the labeling polypeptide coding sequence and the optional HLA protein coding sequence are introduced into tumor cells and/or cancer cells by an oncolytic virus, while playing the role in oncolytic virus killing tumor cells and/or cancer cells, TCR-modified immune cells can also effectively eliminate those tumor cells that cannot complete the replication cycle and produce a sufficient number of progeny viruses and thus cannot be lysed upon infection by oncolytic viruses. As a result, synergy effect is achieved.

Preferably, the replication-selective recombinant oncolytic virus is a recombinant oncolytic adenovirus obtained by genetically modifying an adenovirus type 5. In one embodiment, the E1B-55K gene and/or E1B-19K gene are deleted from the genome of the recombinant oncolytic adenovirus (for example, the E1B-55K gene is deleted, or the E1B-55K gene and E1B-19K gene are deleted), and the genome of the recombinant oncolytic adenovirus comprises an E1A gene coding sequence; preferably, the E1A gene coding sequence is under control of an exogenous promoter.

In one embodiment, the coding sequence of the labeling polypeptide inserted into the oncolytic adenovirus genome can be expressed in tumor cells under control of the adenovirus's own E1B gene promoter, E1B TATA box sequence, and E1B polyadenylation addition signal sequence.

In another embodiment, the coding sequence of the labeling polypeptide inserted into the genome of the oncolytic virus may be under control of a eukaryotic promoter. The eukaryotic promoter includes but is not limited to, the CMV promoter, the EF1a promoter, SV40 promoter, PGK1 promoter, Ubc promoter, human β-actin promoter.

The E1A gene of the recombinant oncolytic adenovirus may be modified so that the expressed E1A protein cannot bind to the pRb protein. In a specific embodiment, the nucleic acid sequence encoding the CR2 region of the E1A protein in the recombinant oncolytic adenovirus genomic DNA has deleted 24 nucleotides at position 923 to 946 of the adenovirus type 5 genomic DNA (oncolytic adenovirus E1A-δ24), and the amino acid sequence of the encoded E1A protein has deleted L-T-C-H-E-A-G-F. The deleted amino acid sequence is the binding region of E1A protein and Rb protein. The E1A protein that deleted this amino acid sequence cannot bind to Rb protein, such that the oncolytic adenovirus E1A-δ24 selectively replicate in tumor cells deficient in Rb/E2F1 pathway and then lyse these tumor cells.

Preferably, the E1A gene of the recombinant oncolytic adenovirus is under control of a tissue-specific promoter or a tumor-specific promoter. The tissue-specific promoter or tumor-specific promoter includes E2F-1 promoter, telomerase hTERT promoter, tyrosinase promoter, prostate specific antigen promoter, alpha-fetoprotein promoter and COX-2 promoter. Preferably, the tumor-specific promoter is the E2F-1 promoter (its nucleotide sequence is SEQ ID NO: 30). In normal cells, because E2F-1 binds to pRb, the expression of E1A regulated by the E2F-1 promoter is inhibited. In tumor cells, due to the deletion or hyperphosphorylation of pRb, the level of "free" E2F-1 increases. The activation of the E2F-1 promoter drives the expression of E1A, and leads to the selective replication of adenovirus in tumor cells which then lyse these tumor cells.

Preferably, the E3 gene of the recombinant oncolytic adenovirus is completely or partially deleted. This can prevent the E3-19K protein from inhibiting the HLA class I antigen presentation pathway, so that the exogenously introduced epitope polypeptide and endogenous tumor antigen can be more effectively presented to the surface of tumor cells.

In certain embodiments, at least one immunodominant epitope recognized by T cells is deleted from the structural protein and functional protein of the adenovirus. Structural and functional proteins include E1A, E1B, hexon, penton substrate, fibrin, capsid protein IX, DNA polymerase, and single-stranded DNA binding protein. In one embodiment, the immunodominant epitope recognized by T cells on the viral protein is removed by site-directed mutagenesis (see WO2016178167A1).

In the therapeutic agent of the present invention, the immune cells modified by T cell receptors include primitive T cells or their precursor cells, NKT cells, or T cell strains.

The T cell receptor includes at least one of an α chain and a β chain, and both the α chain and the β chain include a variable region and a constant region, and the T cell receptor may specifically recognize the epitope polypeptide on the cell surface of tumor cells and/or cancer cells.

Preferably, the amino acid sequence of the variable region of the α chain has at least 98%, preferably at least 98.5%, and more preferably at least 99% identity with the amino acid sequence shown in SEQ ID NO: 1. The amino acid sequence of the variable region of the β chain has at least 98%, preferably at least 98.5%, and more preferably at least 99% identity with the amino acid sequence shown in SEQ ID NO: 2, as long as it does not significantly affect the effect of the present invention. It is also preferred that the amino acid sequence of the variable region of the α chain is as shown in SEQ ID NO: 1, and the amino acid sequence of the variable region of the β chain is as shown in SEQ ID NO: 2.

The variable regions of the α chain and β chain of TCR function to bind the antigen polypeptide/major histocompatibility complex (MHC I), and each includes three hypervariable regions, or called complementarity determining regions (CDRs), that is, CDR1, CDR2, CDR3. Among them, the CDR3 region is very important to specifically recognize the antigen polypeptide presented by the MHC molecule. The α chain of the TCR is formed by the recombination of different V and J gene fragments, and the β chain is formed by the recombination of different V, D, and J gene fragments. The corresponding CDR3 region formed by the recombination of specific gene fragments, as well as the palindromic and random nucleotide additions in the binding region, result in specificity of TCR to antigen polypeptide recognition (see "Immunobiology: The immune system in health and disease. 5$^{th}$ edition, Chapter 4, The generation of Lymphocyte antigen receptors"). The MHC class I molecules include human HLA. The HLA includes: HLA-A, B, and C.

The foreign α chain and β chain of the TCR expressed by T cells may be mismatched with the α chain and β chain of the own TCR of the T cells, which will not only reduce the expression level of the correctly paired foreign TCR, but also render the antigen specificity of the mismatched TCR uncertain, so there is a potential risk of recognizing self-antigens. Therefore, it is preferable to modify the constant regions of the α chain and β chain of the TCR to reduce or avoid mismatches.

In one embodiment, the constant region of the α chain and/or the constant region of the β chain are derived from humans; preferably, the present invention found that the constant region of the α chain can be replaced in whole or in part by homologous sequences derived from other species, and/or the constant region of the β chain can be replaced in whole or in part by homologous sequences derived from other species. More preferably, the other species is mouse.

The replacement can increase the expression level of TCR in the cell, and can further improve specificity of the cell modified by the TCR to the Her2/neu antigen.

The constant region of the α chain may be modified with one or more disulfide bonds, and/or the constant region of the β chain may be modified with one or more disulfide bonds, for example, 1 or 2 disulfide bonds.

In a specific embodiment, TCRs modified in two different ways are prepared. One way is to add a disulfide bond to the constant region of the TCR by site mutation. The method is described in "Cancer Res. 2007 Apr. 15; 67(8): 3898-903.", which is incorporated herein by reference in its entirety. Her2 TCR-1B5-mC is obtained by replacing the corresponding human TCR constant region sequence with the mouse TCR constant region sequence. The method is described in "Eur. J. Immunol. 2006 36: 3052-3059", which is incorporated herein by reference in its entirety.

In a specific embodiment, the amino acid sequence of the α chain is as shown in SEQ ID NOs: 4, 5 or 6, and the amino acid sequence of the β chain is as shown in SEQ ID NOs: 7, 8 or 9.

Among them, for the α chain with an amino acid sequence as shown in SEQ ID NO: 4, its sequence is the original human sequence; for the α chain with an amino acid sequence as shown in SEQ ID NO: 5, its constant region is modified with one disulfide bond; and for the α chain with amino acid sequence as shown in SEQ ID NO: 6, its constant region is replaced with a murine constant region.

Among them, for the β chain with an amino acid sequence as shown in SEQ ID NO: 7, its sequence is the original human sequence; for the β chain with an amino acid sequence as shown in SEQ ID NO: 8, its constant region is modified with one disulfide bond; for the β chain whose amino acid sequence as shown in SEQ ID NO: 9, its constant region is replaced with a murine constant region.

In a specific embodiment, the amino acid sequence of the α chain of the TCR is shown in SEQ ID NO: 4, and the amino acid sequence of the β chain is shown in SEQ ID NO: 7. In another specific embodiment, the amino acid sequence of the α chain of the TCR is shown in SEQ ID NO: 5, and the amino acid sequence of the β chain is shown in SEQ ID NO: 8. In another specific embodiment, the amino acid sequence of the α chain of the TCR is shown in SEQ ID NO: 6, and the amino acid sequence of the β chain is shown in SEQ ID NO: 9.

In other specific embodiments of the present invention, the α chain of the TCR has an amino acid sequence obtained by substituting, deleting, and/or adding one or more amino acids in the amino acid sequence shown in SEQ ID NOs: 4, 5 or 6; For example, the α chain has at least 90%, preferably at least 95%, more preferably at least 99% identity with the amino acid sequence shown in SEQ ID NOs: 4, 5 or 6.

In other specific embodiments of the present invention, the β chain of the TCR has an amino acid sequence obtained by substituting, deleting, and/or adding one or more amino acids in the amino acid sequence shown in SEQ ID NOs: 7, 8 or 9; For example, the β chain has at least 90%, preferably at least 95%, more preferably at least 99% identity with the amino acid sequence shown in SEQ ID NOs: 7, 8 or 9.

The α chain and/or β chain of the TCR of the present invention may also be combined with other functional sequences at the terminal (such as the C-terminal), such as the functional region sequence of the costimulatory signals CD28, 4-1 BB and/or CD3zeta.

The present invention also relates to an isolated nucleic acid encoding a T cell receptor, comprising the coding sequence of at least one of the α chain and the β chain of the T cell receptor, in which the α chain coding sequence and the β chain coding sequence both comprise a variable region coding sequence and a constant region coding sequence, the T cell receptor may specifically recognize the epitope polypeptide on the surface of tumor cells and/or cancer cells.

The amino acid sequence encoded by the α chain variable region coding sequence has at least 98%, preferably at least 98.5%, more preferably at least 99% identity with the amino acid sequence shown in SEQ ID NO: 1, and amino acid sequence encoded by the β chain variable region coding sequence has at least 98%, preferably at least 98.5%, and more preferably at least 99% identity with the amino acid sequence shown in SEQ ID NO: 2, as long as it does not significantly affect the effect of the present invention. It is also preferred that the α chain variable region coding sequence encodes the amino acid sequence shown in SEQ ID NO: 1, and the β chain variable region coding sequence encodes the amino acid sequence shown in SEQ ID NO: 2.

The nucleic acid can be DNA or RNA.

Preferably, the coding sequence of the α chain variable region is shown in SEQ ID NO: 10, and the coding sequence of the β chain variable region is shown in SEQ ID NO: 11.

In one embodiment, the constant region of the α chain and/or the constant region of the β chain are derived from humans; preferably, the coding sequence of the α chain constant region may be replaced in whole or in part by homologous sequences derived from other species, and/or the coding sequence of the β chain constant region may be replaced in whole or in part by homologous sequences derived from other species. More preferably, the other species is mouse. The replacement can increase the expression level of TCR in the cell, and can further improve the specificity of the cell modified by the TCR to the Her2/neu antigen.

The coding sequence of the α chain constant region may include one or more disulfide bond coding sequences, and/or the coding sequence of the β chain constant region may include one or more disulfide bond coding sequences.

In a specific embodiment, the coding sequence of the α chain is shown in SEQ ID NOs: 12, 13 or 14, and the coding sequence of the β chain is shown in SEQ ID NOs: 15, 16 or 17.

Among them, for the α chain with the coding sequence shown in SEQ ID NO: 12, its sequence is the original human sequence; for the α chain with the coding sequence shown in SEQ ID NO: 13, its constant region is modified with one disulfide bond; for the α chain with coding sequence as shown in SEQ ID NO: 14, its constant region is replaced with a murine constant region.

Among them, for the β chain with the coding sequence shown in SEQ ID NO: 15, its sequence is the original human sequence; for the β chain with the coding sequence shown in SEQ ID NO: 16, its constant region is modified with one disulfide bond; for the β chain with coding sequence as shown in SEQ ID NO: 17, the constant region is replaced with a murine constant region.

In a specific embodiment, the coding sequence of the α chain of the TCR is shown in SEQ ID NO: 12, and the coding sequence of the β chain is shown in SEQ ID NO: 12 ID NO: 15. In another specific embodiment, the coding sequence of the α chain of the TCR is shown in SEQ ID NO: 13, and the coding sequence of the β chain is as shown in SEQ ID NO: 16. In another specific embodiment, the coding sequence of the α chain of the TCR is shown in SEQ ID NO: 14, and the coding sequence of the β chain is as shown in SEQ ID NO: 17.

In another embodiment, the α chain coding sequence and the β chain coding sequence are linked by a cleavable linker polypeptide coding sequence, which can increase the expression level of the TCR in the cell. The term "cleavable linker polypeptide" means that the polypeptide plays a linker role and can be cleaved by a specific enzyme, or the nucleic acid sequence encoding this polypeptide is translated through ribosome skipping, so that the linker polypeptides are separated from each other. Examples of cleavable linker polypeptides are known in the art, such as F2A polypeptides. F2A polypeptide sequences include, but are not limited to, F2A polypeptides from Picornavirus and similar 2A class sequences from other viruses. For example, the cleavable/ribosome skipping 2A linker sequence may be derived from different viral genomes, including F2A (foot-and-mouth disease virus 2A), T2A (thosea asigna virus 2A), and P2A (porcine teschovirus-1 type 2A) and E2A (equine rhinitis A virus 2A). In addition, the cleavable linker polypeptide also includes a canonical four amino acid motif that can be cleaved by Furin enzyme, that is, the R—X—[KR]—R amino acid sequence. The TCR encoded in this embodiment is a single-chain chimeric T cell receptor. After the single-chain chimeric T cell receptor is expressed, the cleavable linker polypeptide connecting the α chain and the β chain will be cleaved by a specific enzyme in the cell, thereby forming an equal amount of free α chain and β chain.

The α chain and β chain that make up the single-stranded chimeric TCR can also be described as above, that is, the constant region (and its corresponding coding sequence) may be replaced with homologous sequences derived from other species in whole or in part, and/or modified with one or more disulfide bonds.

In a specific embodiment, the sequence of the nucleic acids is shown in SEQ ID NOs: 18, 19, or 20.

Preferably, the nucleotide sequence of the nucleic acids is optimized to increase gene expression, protein translation efficiency, and protein expression, thereby enhancing the ability of TCR to recognize antigens. Codon optimization includes, but is not limited to, modification of the translation initiation region, modification in mRNA structural fragments, and application of different codons encoding the same amino acid.

In other embodiments, mutations may be made to the sequence of the above-mentioned TCR-encoding nucleic acid, including deletion, insertion and/or substitution of one or more amino acid codons, so that the function of the expressed TCR epitope polypeptide is unchanged or enhanced. For example, in one embodiment, conservative amino acid substitutions include the substitution of one amino acid in the variable region of the above-mentioned α chain and/or β chain of the TCR with another amino acid with similar structure and/or chemical properties. The term "similar amino acids" refers to amino acid residues with similar properties such as polarity, electrical load, solubility, hydrophobicity, and hydrophilicity. The mutated TCR still has the biological activity for recognizing the above-mentioned epitope polypeptide presented by the target cell. In another embodiment, TCR maturation modification is performed, that is, the amino acids in the complementarity determining region 2 (CDR2) and/or CDR3 region in the variable region of the above-mentioned α chain and/or β chain of the TCR are modified by deletion, insertion and/or replacement to change the affinity of the TCR for binding to the epitope polypeptide.

The present invention also relates to a recombinant expression vector for expressing the TCR, which comprises the nucleic acid (for example, DNA) encoding the T cell receptor according to the present invention operatively linked to a promoter, and/or its complementary sequence.

Preferably, in the recombinant expression vector, the DNA encoding the T cell receptor of the present invention is suitably operatively linked to a promoter, an enhancer, a terminator and/or a polyA signal sequence.

The combination of the above acting elements of the recombinant expression vector can promote the transcription and translation of DNA and enhance the stability of mRNA.

The basic skeleton of a recombinant expression vector can be any expression vector knows in the art, including plasmids or viruses. Viral vectors include, but are not limited to, for example, retroviral vectors (the virus prototype is Moloney Murine Leukemia Virus (MMLV)) and lentivirus vector (the virus prototype is human immunodeficiency virus (HIV) type I). The recombinant vector expressing the TCR of the present invention can be obtained by conventional recombinant DNA technology in the art.

In one embodiment, the expression of the α-chain and β-chain genes on the recombinant expression vector may be driven by two different promoters. The promoters include various known types, such as strong expression, weak expression, continuous expression, inducible, tissue-specific, and differentiation-specific promoters. Promoters may be viral or non-viral (for example, eukaryotic promoters), such as CMV promoter, MSCV promoter on LTR, EF1-α promoter, PGK-1 promoter, SV40 promoter, Ubc promoter, CAG promoter, TRE promoter, CaMKIIa promoter, human β-actin promoter. The driving directions of the two promoters can be the same or reverse.

In another embodiment, the expression of the α chain and β chain genes on the recombinant expression vector may be driven by the same promoter, for example, in the case of encoding a single-stranded chimeric T cell receptor, the nucleotide sequence of the α chain and the nucleotide sequence of the β chain is connected by the Furin-F2A polypeptide coding sequence.

In other embodiments, the recombinant expression vector may contain coding sequences of other functional molecules in addition to the α chain and β chain genes. One embodiment includes expression of autofluorescent proteins (such as GFP or other fluorescent proteins) for in vivo tracking imaging. Another embodiment includes expression of an inducible suicide gene system, such as inducing the expression of herpes simplex virus-thymidine kinase (HSV-TK) protein, or inducing the expression of Caspase 9 (iCasp9) protein. The expression of these "safety-switch molecules" can increase the safety of the cells modified by the TCR gene of the present invention when used in vivo (see "Front. Pharmacol., 2014; 5: 1-8"). Therefore, the recombinant expression vector can comprises a suicide gene coding sequence, and the suicide gene may be selected from: iCasp9, HSV-TK, mTMPK, truncated EGFR, truncated CD19, truncated CD20, or a combination thereof. Alternatively, the suicide gene coding sequence is under control of a promoter, and the promoter used to control the suicide gene coding sequence may be the same or different (and independent of each other) from the promoter linked to the nucleic acid of the present invention. Alternatively, the suicide gene coding sequence and the nucleic acid of the present invention are under control of the same promoter, and the suicide gene coding sequence may be cleavably linked to the coding sequence of the polypeptide or the internal ribosome entry site (IRES) sequence is connected to the nucleic acid of the present invention. The coding sequence of the cleavable linker polypeptide may be the cleavable/ribosome skipping 2A linker sequence described above, which may be derived from different viral genomes, including F2A, T2A, P2A and E2A. Another embodiment includes expression of human chemokine receptor genes, such as CCR2. These chemokine receptors may bind to corresponding chemokine ligands highly expressed in tumor tissues, thereby increasing homing of cells modified by the TCR gene of the present invention in tumor tissues.

Preferably, the first composition comprises a therapeutically effective amount of the DNA or a therapeutically effective amount of the mRNA.

More preferably, the first composition comprises a therapeutically effective amount of the recombinant virus. Preferably, when the recombinant virus is a recombinant oncolytic adenovirus, the dosage of the recombinant oncolytic adenovirus is $5 \times 10^7$-$5 \times 10^{12}$ vp/day, 1-2 times a day for 1-7 days.

More preferably, the second composition contains a therapeutically effective amount of the T cell receptor modified immune cells. Preferably, the T cell receptor-modified immune cells with a total dose range of $1 \times 10^3$-$1 \times 10^9$ cells/Kg body weight per treatment course are included.

The DNA can be formulated to be administered by intratumoral injection, for example, it can be administered by direct intratumoral injection in the form of plasmids, or by intratumoral injection after packaged by a liposome, or by intratumoral injection after connection to nanoparticles (such as polymers like poly-L-lysine, polyamino acid, polyethyleneimine and chitosan, and the like), or by electrotransfection after intratumoral injection to enhance the transfection rate. The mRNA may also be formulated to be administered by intratumoral injection in a similar manner.

The recombinant virus can be formulated to be administered by intratumoral injection, intraperitonealy, intra-subarachnoidly or intravenously.

The immune cells can be formulated to be administered intraarterially, intravenously, hypodermically, intracutaneously, intratumorally, intralymphatically, intralympnode, intra-subarachnoidly, intramedullarily, intramuscularily or intraperitoneally.

Preferably, the therapeutic agent is composed of the first composition and the second composition.

Those skilled in the art can understand that the therapeutic agent of the present invention can also comprise suitable pharmaceutically acceptable auxiliary materials, including pharmaceutical or physiological carriers, excipients, diluents (includes physiological saline, PBS solution), and various additives, including sugars, lipids, polypeptides, amino acids, antioxidants, adjuvants, preservatives, etc.

The present invention also provides the use of the therapeutic agent in the preparation of drugs for the treatment of tumors and/or cancers.

The tumors and/or cancers include: head and neck tumor, synovial cancer, kidney cancer, connective tissue cancer, melanoma, lung cancer, esophageal cancer, colon cancer, rectal cancer, brain cancer, liver cancer, bone cancer, choriocarcinoma, gastrinoma, pheochromocytoma, prolactinoma, blood cancer, neuroma, von Hippel-Lindau disease, Zollinger-Ellison syndrome, anal cancer, cholangiocarcinoma, bladder cancer, ureteral cancer, glioma, neuroblastoma, meningioma, spinal cord tumor, osteochondroma, chondrosarcoma, Ewing's sarcoma, carcinoma of unknown primary site, carcinoid, fibrosarcoma, breast cancer, Paget's disease, cervix carcinoma, esophageal cancer, gallbladder cancer, eye cancer, Kaposi's sarcoma, prostate cancer, testicular cancer, skin cancer, mesothelioma, multiple myeloma, ovarian cancer, pancreatic endocrine tumor, glucagonoma, pancreatic cancer, penile cancer, pituitary cancer, soft tissue sarcoma, retinoblastoma, small bowel cancer, gastric cancer, thymic cancer, trophoblastic carcinoma, hydatidiform mole, endometrial cancer, vaginal cancer, vulvar cancer, mycosis fungoides, insulinoma, heart cancer, meningeal cancer, blood cancer, peritoneal cancer and pleural cancer. The tumors and/or cancers may include those that are HLA-A2 positive and Her2/neu negative, HLA-A2 negative and Her2/neu positive, HLA-A2 and Her2/neu both positive, or HLA-A2 and Her2/neu both negative. The therapeutic agent within the scope of the present invention can be administered to the patient according to the actual condition of the tumors and/or cancers in patients.

The present invention also provides the labeling polypeptide described above herein.

Preferably, the amino acid sequence of the labeling polypeptide has at least 98%, more preferably at least 98.5%, and still more preferably at least 99% identity with the amino acid sequence shown in SEQ ID NO: 24, SEQ ID NO: 36, SEQ ID NO: 56, or SEQ ID NO: 60. Further preferably, the amino acid sequence of the labeling polypeptide is as shown in SEQ ID NO: 24, SEQ ID NO: 36, SEQ ID NO: 56 or SEQ ID NO: 60.

The present invention also provides an isolated nucleic acid having the coding sequence of the labeling polypeptide according to the present invention. The amino acid sequence of the labeling polypeptide has at least 98%, more preferably at least 98.5%, and still more preferably at least 99% identity with the amino acid sequence shown in SEQ ID NO: 24, SEQ ID NO: 36, SEQ ID NO: 56, or SEQ ID NO: 60. The various embodiments of the nucleic acid are as described above.

Preferably, the nucleic acid is DNA, and its nucleotide sequence is shown in SEQ ID NO: 25 (corresponding to the sequence not including HLA-A2), SEQ ID NO: 26 (corresponding to the sequence including HLA-A2 is positioned before the labeling polypeptide), SEQ ID NO: 27 (corresponding to the sequence including HLA-A2, where HLA-A2 is positioned after the labeling polypeptide), SEQ ID NO: 57, SEQ ID NO: 58 or SEQ ID NO: 61. The corresponding amino acid sequence is as shown in SEQ ID NO: 24 (corresponding to the sequence not including HLA-A2), SEQ ID NO: 31 (corresponding to the sequence including HLA-A2, where HLA-A2 is positioned before the labeling polypeptide), SEQ ID NO: 32 (corresponding to the sequence including HLA-A2, wherein HLA-A2 is positioned after the labeling polypeptide), SEQ ID NO: 56, SEQ ID NO: 36 or SEQ ID NO: 60.

The present invention also provides the use of the nucleic acid in the preparation of medication for the treatment or prevention of tumors and/or cancers.

The invention also provides a recombinant expression vector containing the nucleic acid according to the invention and/or its complementary sequence.

Preferably, in the recombinant expression vector, the nucleic acid of the present invention is suitably effectively linked to a promoter, an enhancer, a terminator and/or a polyA signal sequence.

The combination of the above-mentioned functional elements of the recombinant expression vector of the present invention can promote DNA transcription and translation, and enhance the stability of mRNA.

The basic skeleton of a recombinant expression vector may be any expression vector known in the art, including plasmids or viruses. Viral vectors include, but are not limited to, for example, retroviral vectors (the virus prototype is MMLV) and lentivirus vector (the virus prototype is HIV type I). The recombinant vector expressing the labeling polypeptide of the present invention may be obtained by conventional recombinant DNA technology in the art.

In some embodiments, the basic backbone of the recombinant expression vector is an oncolytic adenovirus. The promoter is an endogenous viral gene promoter, such as an E1A promoter, an E1B promoter, or an E3 promoter. In certain embodiments, the promoter is a tissue-specific or tumor-specific promoter. Preferably, in some embodiments, the promoter is the E2F-1 promoter shown in SEQ ID NO:30.

In other embodiments, in addition to the nucleic acid described herein, the recombinant expression vector may also comprise coding sequences of other functional molecules, such as reporter genes, which can be used to identify whether cells are transfected with the recombinant expression vector, or used to determine protein levels and activities, for example, by flow cytometry, amplification/expression methods, immunohistochemical methods, FISH and release antigen assays, Southern blotting, Western blotting or PCR techniques. Therefore, methods for measuring protein levels in cells are generally known in the art.

The present invention also provides the use of the recombinant expression vector in the preparation of medication for the treatment or prevention of tumors and/or cancers.

The present invention also provides an isolated recombinant virus, wherein the genome of the recombinant virus has the nucleic acid according to the present invention; and the recombinant virus includes a replication-selective recombinant oncolytic virus or a replication-defective recombinant virus. The various embodiments of the isolated recombinant virus are as described above.

The present invention also provides the use of the recombinant virus in the preparation of medication for the treatment or prevention of tumors and/or cancers.

The present invention also provides a kit of combinational drugs with synergistic effects for the treatment of tumors and/or cancers, including:

a first container comprising the first composition of the therapeutic agent according to the present invention;

a second container comprising the second composition of the therapeutic agent according to the present invention, wherein the first container is separate from the second container; and instructions specifying the timing and routes of administration.

The invention also provides the use of the kit in the preparation of drugs for the treatment or prevention of tumors and/or cancers.

The tumors and/or cancers include: head and neck tumor (including nasopharyngeal cancer), synovial cancer, kidney cancer, connective tissue cancer, melanoma, lung cancer, esophageal cancer, colon cancer, rectal cancer, brain cancer, liver cancer, bone cancer, choriocarcinoma, gastrinoma, pheochromocytoma, prolactinoma, blood cancer, neuroma, von Hippel-Lindau disease, Zollinger-Ellison syndrome, anal cancer, cholangiocarcinoma, bladder cancer, ureteral cancer, glioma, neuroblastoma, meningioma, spinal cord tumor, osteochondroma, chondrosarcoma, Ewing's sarcoma, carcinoma of unknown primary site, carcinoid, fibrosarcoma, breast cancer, Paget's disease, cervical carcinoma, esophageal cancer, gallbladder cancer, eye cancer, Kaposi's sarcoma, prostate cancer, testicular cancer, skin cancer, mesothelioma, multiple myeloma, ovarian cancer, pancreatic endocrine tumor, glucagon tumor, pancreatic cancer, penile cancer, pituitary cancer, soft tissue sarcoma, retinoblastoma, small bowel cancer, gastric cancer, thymic cancer, trophoblastic carcinoma, hydatidiform mole, endometrial cancer, vaginal cancer, vulvar cancer, mycosis fungoides, insulinoma, heart cancer, meningeal cancer, blood cancer, peritoneal cancer and pleural cancer. The tumors and/or cancers may include those that are HLA-A2 positive and Her2/neu negative, HLA-A2 negative and Her2/neu positive, HLA-A2 and Her2/neu both positive, or HLA-A2 and Her2/neu both negative. The kit within the scope of the present invention can be provided to the patient according to the actual situation of the tumors and/or cancers in patients.

The present invention also provides a method for the treatment of tumor and/or cancer, including:

administering the first composition of the therapeutic agent according to the present invention to a patient suffering from tumor and/or cancer; and administering the second composition of the therapeutic agent according to the present invention to a patient suffering from tumor and/or cancer.

The first composition and the second composition of the therapeutic agent may be administered simultaneously (for example, simultaneous intratumor injection as a mixture), separately but simultaneously (for example, administered by intratumoral and intravenous injection respectively) or in sequence (for example, first composition is administered first, and then the second composition is administered; or the second composition is administered first, and then the first composition is administered).

Preferably, the method comprises the following steps in a sequential manner:

1) administering the first composition to the patient suffering from tumor and/or cancer; and
2) administering the second composition of the therapeutic agent to the patient suffering from tumor and/or cancer after the administration of the first composition.

Preferably, 1-30 days after the administration of the first composition, the second composition of the therapeutic agent is administered to the patient suffering from tumor and/or cancer.

The phrase "1-30 days after the administration of the first composition, the second composition of the therapeutic agent is administered to the patient suffering from tumor and/or cancer" means that the time interval between the first administration of the second composition and the first administration of the first composition is in the range of 1 day to 30 days (for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days), or the time interval between the first administration of the second composition and the most recent administration of the first composition is 1 day to 30 days (for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days). Preferably, the time interval between the first administration of the second composition and the most recent administration of the first composition is 3 days to 14 days (for example, 3, 4, 5, 6, 7, 8, 9, 10, 11, 12, 13, 14 days).

In a preferred embodiment of the present invention, the first composition comprises the recombinant oncolytic adenovirus, and the administration dose of the recombinant oncolytic adenovirus is $5 \times 10^7$-$5 \times 10^{12}$ vp/day, 1-2 times per day, and consecutively for 1-7 days, or any value in the above range.

In a preferred embodiment of the present invention, the administered dose of the T cell receptor-modified immune cells is $1 \times 10^3$-$1 \times 10^9$ cells/Kg body weight for total dose per treatment course. Preferably, it is administered 1-3 times per day, and consecutively for 1-7 days.

In certain embodiments, the method for treatment of tumor and/or cancer further includes administering other drugs for treatment of tumors and/or cancers to the patient, and/or medicaments for regulating the patient's immune system, to enhance the number and function of TCR-modified immune cells in the body. The other medicaments used to treat tumors and/or cancers include but are not limited to: chemotherapy drugs, such as cyclophosphamide, fludarabine; radiotherapy drugs; immunosuppressants, such as cyclosporine, azathioprine, Methotrexate, mycophenolate, FK50; antibodies, such as antibodies against CD3, IL-2, IL-6, IL-17 and TNFα.

In certain embodiments, the method for the treatment of tumors and/or cancers further includes administering to the patient other drugs for the treatment of tumors and/or cancers, and/or drugs for regulating the patient's immune system, which is used to eliminate the number and function of the TCR-modified immune cells carrying the suicide gene in the body when the TCR-modified immune cells produces serious side effects. The other drugs used to treat tumors and/or cancers include but are not limited to: chemically induced dimerization (CID) drugs, AP1903, phosphorylated ganciclovir, anti-Cd20 antibodies, anti-CMYC antibodies, and anti-EGFR Antibody.

The DNA may be formulated to be administered by intratumoral injection, for example, it can be administered by direct intratumoral injection in the form of plasmids, intratumoral injection after being packaged by a liposome, or intratumoral injection after connection to nanoparticles (such as poly-L-lysine, polyamino acid, polyethyleneimine and chitosan, and other polymers), or electrotransfection after intratumoral injection to enhance the transfection rate. The mRNA can also be formulated to be administered by intratumoral injection in a similar manner.

The recombinant virus can be formulated to be administered by intratumoral injection, intraperitonealy, intra-subarachnoidly or intravenously.

The T cell receptor-modified immune cells can be formulated to be administered intraarterially, intravenously, hypodermically, intracutaneously, intradermally, intratumorally, intralymphatically, intralympnode, intra-subarachnoidly, intramedullarily, intramuscularily or intraperitoneally.

The tumors and/or cancers include: head and neck tumor (including nasopharyngeal cancer), synovial cancer, kidney cancer, connective tissue cancer, melanoma, lung cancer, esophageal cancer, colon cancer, rectal cancer, brain cancer, liver cancer, bone cancer, choriocarcinoma, gastrinoma, pheochromocytoma, prolactinoma, blood cancer, neuroma, von Hippel-Lindau disease, Zollinger-Ellison syndrome, anal cancer, cholangiocarcinoma, bladder cancer, ureteral cancer, glioma, neuroblastoma, meningioma, spinal cord tumor, osteochondroma, chondrosarcoma, Ewing's sarcoma, carcinoma of unknown primary site, carcinoid, fibrosarcoma, breast cancer, Paget's disease, cervical carcinoma, esophageal cancer, gallbladder cancer, eye cancer, Kaposi's sarcoma, prostate cancer, testicular cancer, skin cancer, mesothelioma, multiple myeloma, ovarian cancer, pancreatic endocrine tumor, glucagon tumor, pancreatic cancer, penile cancer, pituitary cancer, soft tissue sarcoma, retinoblastoma, small bowel cancer, gastric cancer, thymic cancer, trophoblastic carcinoma, hydatidiform mole, endometrial cancer, vaginal cancer, vulvar cancer, mycosis fungoides, insulinoma, heart cancer, meningeal cancer, blood cancer, peritoneal cancer and pleural cancer. The tumors and/or cancers may include those that are HLA-A2 positive and Her2/neu negative, HLA-A2 negative and Her2/neu positive, HLA-A2 and Her2/neu both positive, or HLA-A2 and Her2/neu both negative. The method within the scope of the present invention can be provided to the patient according to the actual situation of the tumors and/or cancers in patients.

The following will further explain or illustrate the content of the present invention by way of examples, but these examples should not be construed as limiting the protection scope of the present invention.

EXAMPLES

Unless otherwise specified, the experimental methods used in the following examples are performed using conventional experimental procedures, operations, materials, and conditions in the field of medical biological engineering.

Unless otherwise specified, all the percentage concentrations (%) of the respective agents indicate percentage by volume (% (v/v)).

1. Cell strains: The cell strains used to prepare the lentiviral particles is 293T cells (ATCC CRL-3216). The presenting cell line for presenting antigenic peptides is T2 cells (174×CEM.T2, ATCC CRL-1992). The tumor cell strains used to detect functions are human colorectal cancer colo205 cells (ATCC CCL-222), HT-29 cells (HTB-38) and HCT116 cells (ATCC CCL-247), human breast cancer MDA-MB-231 cells (ATCC HTB-26) and MCF7 cells (ATCCHTB-22), human ovarian cancer SKOV3 cells (ATCC HTB-77), human pancreatic cancer PANC-1 cells (ATCCCRL-1469), human glioma U87MG cells (ATCC HTB-14), human hepatocellular carcinoma HepG2 cells (ATCC HB-8065), human non-small cell lung cancer NCI-H460 cells (ATCC HTB177), small cell lung cancer NCI-H446 cells (ATCC HTB-171). The cell strains are cultured in RPMI-1640 complete medium (Lonza, cat #12-115F). The RPMI-1640 complete medium is supplemented with 10% of fetal bovine serum FBS (ATCC 30-2020), 2 mmol/L of L-glutamic acid, 100 μg/ml of penicillin and 100 μg/ml of streptomycin.

Peripheral blood product: unless otherwise specified, the human peripheral blood products (including peripheral blood monocyte cells) from healthy donors used in the test are from Pacific Blood Center in San Francisco (#1 PBMC and #2 PBMC are Trima residual cell components #R32334 and #R33941 from the Apheresis method collection kit, respectively).

Counting by trypan blue staining method: the cells was washed with PBS, digested with trypsin, then suspended in PBS, trypan blue dye solution at a final concentration of 0.04% (w/v) was added, and counted under a microscope. Dead cells will be stained in light blue, and live cells resist staining. Take the number of live cells as the final data.

In vitro induction of Her2/neu 369-377 specific cytotoxic T cells (CTL): peripheral blood was centrifuged by Ficoll-Paque Premium (Sigma-Aldrich, cat #GE-17-5442-02) density gradient centrifugation (×400 g) for 30 minutes to obtain a single monocyte cell (PBMC). Firstly, the HLA-A2 phenotype of the cells was detected by staining with fluorescein FITC-labeled anti-HLA-A2 antibody (Biolegend, cat #343303), and the RNA of positive cells was extracted after analyzed by flow cytometry (flow cytometer is MACSQuant Analyzer 10 (Miltenyi Biotec), and the result is analyzed with Flowjo software (Flowjo company)), reverse transcribed into cDNA and cloned into the vector, and then HLA gene sequencing analysis was performed to determine the cell type as HLA-A*0201. HLA-A2 positive PBMCs were cultured in the culture wells of a 24-well culture plate, and the culture medium was the above-mentioned RPMI-1640 complete medium. 2×10e6/ml PBMCs per well was achieved and Her2/neu 369-377 polypeptide (Her2-E75, synthesized with Peptide2.0, 10 μg/ml dissolved in DMSO) was added such that the final concentration was 1 μg/ml. After culturing in an incubator at 37° C. in 5% $CO_2$ for 16-24 hours, the cytokines were added at the following final concentrations: 100 IU/ml of human IL-2 (Peprotech, cat #200-02), 5 ng/ml of human IL-7 (Peprotech Company, cat #200-07), 5 ng/ml of human IL-15 (Peprotech Company, cat #200-15). After culturing for 10 to 14 days, the cultured T cells were re-stimulated with antigen: 10e6 cells of the above-obtained cultured cells were added to each well of the 24-well plate, and 2×10e6 cells HLA-A2-positive PBMCs treated by 25 μg/ml of mitomycin C (Santa Cruz Biotechnology, cat #SC-3514) for 2 hours were added as trophoblasts, and Her2/neu 369-377 polypeptide at a final concentration of 1 μg/ml was added to each well, and 100 IU/ml of IL-2, 5 ng/ml of IL-7, 5 ng/ml of IL-15 (final concentration) were added after culturing overnight. After two cycles of antigen stimulation and re-stimulation, the amplified T cells were collected for phenotype analysis and T cell cloning.

Flow cytometry analysis and single cell separation: The phenotype of T cells expressing Her2/neu 369-377 specific TCR was analyzed by flow cytometry. The tested cells were collected in a 1.5 ml of tube (the number of cells was about 10e5), washed once time with 1 ml of DPBS solution (2.7 mM KCl, 1.5 mM $KH_2PO_4$, 136.9 mM NaCl, 8.9 mM $Na_2HPO_4 \cdot 7H_2O$, pH 7.4) and replaced in 100 μl of DPBS containing 1% calf serum, 5 μl of fluorescein APC-labeled anti-human CD8 antibody (Biolegend, cat #300912), and 10 μl of fluorescein PE-labeled Her2-E75/HLA-A2 tetramer (Her2-E75 tetramer, MBL International Co., cat #T01014) or Her2-E75/HLA-A2 pentamer (Her2-E75 pentamer, Proimmune, cat #F214-2A-D), after ice incubation for 30 minutes, washed twice with DPBS solution and resuspended in 100 μl of PBS solution (8 mM $Na_2HPO_4$, 136 mM NaCl, 2 mM $KH_2PO_4$, 2.6 mM KCl, pH7.2-7.4) for flow cytometric analysis. The flow cytometer was MACSQuant Analyzer 10 (Miltenyi Biotec), and Flowjo software (Flowjo) was used to analyze the results. T cell clones were obtained by culturing single cells after separation using a flow cytometer (FACS sorter). The PBMCs stimulated by Her2/neu369-377 polypeptide antigen were stained with APC-labeled anti-human CD8 antibody and PE-labeled Her2-E75/HLA-A2 pentamer, and then subjected to flow cytometry (Model: Sony cell sorter SH800) for separation. After a single CD8+Her2-E75/HLA-A2 pentamer+ cell was sorted into a single culture well of a 96-well culture plate, HLA-A2-positive PBMCs treated with 25 µg/ml mitomycin C for 2 hours were added, 10e5 cells per well, 1 µg/ml of Her2/neu 369-377 peptide was added to culture overnight, and then RPMI-1640 complete culture medium containing 100 IU/ml of IL-2, 5 ng/ml of IL-7, and 5 ng/ml of IL-15 were added. The culture medium containing the cytokines was replaced every 3-4 days, and the growth of T cell clones was observed under a microscope. The proliferated T cells were collected, and antigen re-stimulation was performed according to the above method to obtain a sufficient number of cells. Phenotypic or functional testing was performed, and RNA was extracted to clone the TCR gene.

T cell function test: in order to test the ability of T cells transfected with TCR gene to recognize epitope polypeptides, 10e5 of T cells transfected with TCR gene and 10e5 of T2 cells were added to each well of a 96-well plate, mixed for cultivation at 100 µl/Each well of RPMI-1640 complete medium and each experimental group was performed in duplicate wells. Then Her2/neu 369-377 polypeptides at different final concentrations (1 µg/ml, 0.5 µg/ml, 0.1 µg/ml, 0.05 µg/ml, 0.01 µg/ml, 0.005 µg/ml, 0.001 µg/ml and 0.0001 µg/ml respectively) were added, and then placed in an incubator at 37° C. in 5% $CO_2$ for overnight culture.

In order to test the ability of T cells transfected with TCR gene to recognize tumor cell strains, a certain number of PBMCs and tumor cells transfected with TCR gene as target cells were added to each well of a 96-well plate according to different E:T (effector cells to target cells) ratio. After 24 hours of cultivation, the supernatant was collected to detect the secreted IFN-γ in the supernatant. Each experimental group was duplicate wells or three wells. In the antibody function blocking test, an anti-human CD8 antibody (Biolegend, cat #300912) at a final concentration of 10 µg/ml was added to the cell culture well at the same time, and the cells were cultured overnight in an incubator at 37° C. in 5% $CO_2$. The cell supernatant was collected at 18-24 hours and the human IFN-γ ELISA Read-set-Go kit (eBioscience, cat #88-7316) or human IFN-γ DuoSet ELISA kit (R&D Systems, cat #DY285B) was used to detect the IFN-γ in the supernatant according to the manufacturer's instructions.

In order to test the ability of T cells transfected with TCR gene to kill tumor cells, 1×10e4 of target cells were added to each well of a 24-well culture plate and cultured for 24 hours to fully adhere the target cells on the wall, and then the suspended cells were removed. A certain number of T cells transfected with TCR gene were added according to the set E:T ratio. After 24 hours of cultivation, the suspended cells were removed, and adherent cells were collected by trypsinization and stained with trypan blue to count viable cells. Cytotoxicity %=((the number of viable cells in the target cells at the initial of culture−the number of viable cells in the target cells at the end of culture)/the number of viable cells in the target cells at the initial of culture)×100. Each experimental group was duplicate wells or three wells, and the difference significance was analyzed by Student's t-test.

MTT Counting Method:

The cells in the logarithmic growth phase were digested with trypsin. After the digestion was terminated, the cells were centrifuged and collected, blown evenly to prepare a single cell suspension; the cell concentration was adjusted to 0.1~10×10⁴/ml with cell culture solution (the number of inoculated cells was adjusted depending on different cell growth conditions), inoculated on a 96-well cell culture plate with a culture system of 100 µl/well, placed in an incubator at 37° C. in 5% $CO_2$ overnight to make the cells fully adherent, reaching 70-80% confluence on the next day; counting method: counting with a counting board, and a countstar counter was used to verify the counting correctness. The 96-well plate was taken out, and 100 µl of pre-prepared T cell and TCR-T cell suspension were added, vortex mixed slightly before loading, 100 µl of serum-free medium for cell culture was added to a blank control well; placed in an incubator at 37° C. in 5% $CO_2$ for 24 hours respectively; after 24 hours, cells were taken, centrifuged at 400 g, and 10 minutes later, 180 µl of culture medium was drawn into a new 96-well plate. The sample was kept and used for later ELISA detection of IFN-γ level in supernatant. Please refer to the test instructions for the detection steps. Note: The supernatant can be frozen at −80° C. for subsequent testing. A new 100 µl of complete medium was added to each well, and 10 µl of MTT solution (5 mg/ml, or 0.5% MTT) was added to each well, continued to culture for 4-6 hours; an effector cell control group was set up, and after adding MTT for 4 hours, centrifuged at 300 g for 5 minutes, the effector cells stained with MTT were centrifuged at the bottom of the plate, the supernatant was discarded, and DMSO was added for detection. 150 µl of DMSO was added to each well, placed on a shaker and shaken at low speed for 10 minutes to fully dissolve the crystals, and the absorbance at 490 nm was detected on a microplate reader.

Obtaining monoclonal TCR gene: Zymo Quick-RNA Microprep kit (Zymo Research, cat #R1050) was used to purify total RNA from T cell clones, and cDNA was obtained using Smarter RACE 5/3' kit (Takara, USA) Bio company, cat #634858) by using the total RNA as a template. PCR was performed with 5'-CDS primer and TCR β chain 3'primer 5'-GCCTCTGGAATCCTTTCTCTTG-3' (SEQ ID NO: 33) and α chain 3'primer 5'-TCAGCTGGAC-CACAGCCGCAG-3' (SEQ ID NO: 34), such that a full sequence of α and β gene fragments of TCR were amplified and cloned into pRACE vector (Takara Bio, USA, cat #634858) respectively. The competent bacteria Stellar (Takara Bio, USA, cat #636763) was transformed and then the plasmids were obtained for sequencing.

Preparation of recombinant TCR lentiviral expression vector: The viral vector used to express TCR is a replication-defective lentiviral vector, including: the GFP-expressing lentiviral vector pCDH-EF1α-MCS-(PGK-GFP), which can be purchased from System Biosciences (Cat #CD811A-1); and the vector pCDH-EF1α-MCS that does not express GFP, obtained by removing the PGK promoter and GFP gene on the pCDH-EF1α-MCS-(PGK-GFP) vector by using conventional techniques in the art. Based on the obtained TCR gene sequence, a complete gene sequence of β chain, α chain of TCR and a cleavable F2A sequence and Furin digestion fragment between them were synthesized, and then it was linked to a multiple cloning site downstream of the EF-1α promoter of the vector, the transcription sequence of inserting TCR is @ chain of TCR (without stop codon), Furin digestion fragment, F2A fragment, α chain of TCR sequentially (as for the method, see "Gene Ther. 2008 November; 15(21): 1411-1423"). The vector expressing GFP is driven by ta reverse PGK promoter. For vectors that do not express GFP, the PGK promoter and GFP fragment are removed.

Preparation of recombinant TCR lentiviral particles: TCR lentiviral particles were obtained by transfecting 293T/293FT cells with Lipofectaine 2000 transfection reagent (invitrogen, #11668019). 293T/293FT cells and transfection process were prepared according to the manufacturer's instructions. Transfection was carried out in a 6-well culture plate. Firstly, Opti-MEM 1 medium (Thermo Fisher Company, cat #51985091) was used to prepare a liposome mixture solution of transfected plasmid. According to the manufacturer's instructions, 6 μl of lipofectaine 2000 reagent, 0.8 μg of TCR lentiviral vector plasmid and 1.8 μg of pCDH system virus packaging plasmid (SBI company, cat #LV500A-1) were added to 250 μl of culture liquid, mixed and incubated for 25 minutes, and then added to 293T/293FT cell culture wells. Then, the resultant was incubated at 37° C. in 5% $CO_2$ for 16 hours. A FBS-free DMEM medium (Thermo Fisher, cat #11965092) was used to replace the old medium, and after continuing to culture for 24 hours and 48 hours, the cell supernatants were collected respectively, and centrifuged at 2000 g for 10 minutes. A 0.4 μm filter membrane was used for filtration, and the virus supernatant as obtained was concentrated with lentivirus concentrate (GeneCopoeia™ #LPR-LCS-01) according to the manufacturer's instructions for infecting cells.

Recombinant TCR lentivirus transfected human T cells: The frozen primary PBMCs were thawed and cultured in RPMI-1640 complete medium for 24 hours. Dead cells were removed by Ficoll-Paque Premium density gradient centrifugation (×400 g) for 30 minutes. It was placed in wells of a 24-well plate, which was treated with 2 μg/ml of anti-human CD3 antibody (Biolegend, OKT3 clone cat #317303) and 2 μg/ml of anti-human CD28 antibody (Biolegend, cat #302914) (wherein each well was added with 100 μl DPBS solution containing the above-mentioned CD3 antibody and CD28 antibody) for 24 hours. The cell concentration is 2×10e6/ml, and it is also possible to use Dynabead human T-CD3/CD8 magnetic beads (Thermo Fisher Company, cat #11131D) according to the manufacturer's instructions to conduct stimulation activation of PBMCs. After 24 hours of cultivation, the cells were collected, and 100 μl of concentrated TCR lentiviral particles (3×10e8 Tu/ml) were added to the wells of a 24-well plate. The cells were continued for cultivation with the RPMI-1640 complete culture medium containing IL-2 100 IU/ml, IL-7 5 ng/ml and IL-15 5 ng/ml, or X-VIVO15 (Lonza #04-418Q), and replaced with fresh culture medium containing the above-mentioned cytokines every 3 days. It is also possible to use a culture plate pretreated with Restro-Nectin (Takara Company, cat #T110A) to infect activated PBMCs with the virus according to the manufacturer's instructions. Generally, phenotypic and functional tests can be performed after 72 hours. Transfection of T cell strains was also carried out in accordance with the above steps. If the viral vector is labeled with GFP, the GFP-positive cells can be observed under a fluorescence microscope 48 hours after transfection.

Preparation Example 1: Preparation of the Recombinant Lentiviral Vector Expressing Labeling Polypeptide Firstly, the exogenously expressed gene was obtained, and the HLA-A201 gene fragment was obtained by RT-PCR. RNA was extracted from HLA-A201+ PBMCs, and HLA-A201 gene was obtained using Superscript RT-PCR kit (Thermo Fisher, cat #12574018) according to the manufacturer's instructions. The sequencing confirmed that it was complete sequence (the amino acid sequence thereof is as shown in SEQ ID NO: 29, the nucleotide sequence is as shown in SEQ ID NO: 35). The gene fragments of the labeling polypeptide were gene fragments obtained by DNA synthesis (Integrated DNA Technologies, gblocks Gene Fragments), including: labeling polypeptide "E75×1" (without KDEL at the C-terminal) (the amino acid sequence thereof is as shown in SEQ ID NO: 56, and the nucleotide sequence thereof is as shown in SEQ ID NO: 57); labeling polypeptide "E75×4" (without KDEL at the C-terminus) (the amino acid sequence thereof is as shown in SEQ ID NO: 36, and the nucleotide sequence thereof is as shown in SEQ ID NO: 58); the labeling polypeptide "E75×8" (without KDEL at the C terminal) (its amino acid sequence is as shown in SEQ ID NO: 60, and its nucleotide sequence is as shown in SEQ ID NO: 61). The lentiviral vector pCDH-EF1α-MCS-(PGK-GFP) was purchased from System Biosciences (Cat #CD811A-1). The HLA-A2 gene fragment was inserted into the multiple cloning sites downstream of the EF1a promoter by using the conventional gene cloning techniques in the art. After the plasmid was digested with Xcm-1, the GFP gene fragments were removed, and the synthetic gene fragments of the labeling polypeptide were inserted into the downstream of the PGK promoter to replace the GFP gene by using conventional gene cloning techniques in the art, and "pCDH-EF1p-A2-PKGp-E75×1", "pCDH-EF1p-A2-PKGp-E75×4" and "pCDH-EF1p-A2-PKGp-E75×8" were obtained respectively. The sequencing results of each plasmid were correct.

The HLA-A2 gene was connected with the coding sequence of the labeling polypeptide "E75×8" (with KDEL at the C terminal) by the furin digestion sequence and F2A sequence to form the A2-Her2E75 sequence fragment (its nucleotide sequence is as shown in SEQ ID NO: 26). In-fusion cloning kit (Takara Bio, cat #638909) was used to carry out PCR according to the manufacturer's instructions, and the primers as used were 5'-AGAGCTAGCGAATT-CAACATGGCCGTCATG-3' (SEQ ID NO: 37) and 5'-TGATTGTCGACGCCCTTAAAGCTCGTCTTTAAG-GAAG-3' (SEQ ID NO: 38). After the gene fragments were amplified by high-fidelity PCR, the A2-Her2E75 fragment was inserted into the multi-gene cloning sites downstream of the EF1α promoter of the lentiviral vector pCDH-EF1α-MCS-(PGK-GFP) (purchased from System Biosciences, Cat #CD811A-1) by using conventional gene cloning techniques in the art, so as to obtain the CD811-EF1α-A2-F2A-HerE75 plasmid.

Preparation Example 2: Preparation of Replication-Defective Recombinant Adenovirus Expressing Labeling Polypeptide/HLA-A2

1) Preparation of Replication-Defective Recombinant Adenovirus Vector Expressing Labeling Polypeptide/HLA-A2

Recombinant adenovirus was mainly prepared according to the preparation method of AdEasy system (see "Nature protocols 2007; 2:1236-1247"). Firstly the exogenously expressed gene was obtained, and the HLA-A201 gene fragment was obtained by RT-PCR. RNA was extracted from HLA-A201+ PBMCs, and the HLA-A201 gene was obtained according to the manufacturer's instructions using Superscript RT-PCR kit (Thermo Fisher, cat #12574018). It was confirmed to be the complete sequence by sequencing. Other exogenous genes, such as Her2-E75 minigenes, or tandem minigenes and expression regulatory elements, were gene fragments obtained by DNA synthesis (Integrated DNA Technologies, gblocks Gene Fragments), including: the labeling polypeptide "E75×8" (the C-terminal has KDEL) (its amino acid sequence is as shown in SEQ ID NO: 24, and its nucleotide sequence is as shown in SEQ ID NO: 59). The HLA-A2 gene was connected with the coding sequence of the labeling polypeptide "E75×8" by the furin digestion sequence and F2A sequence through In-Fusion cloning technology, so as to form A2-Her2E75 sequence fragment (its nucleotide sequence is as shown in SEQ ID NO: 26). PCR was performed using In-fusion cloning kit (Takara Bio, cat #638909) according to the manufacturer's instructions. The primers used were 5'-TAGAGAT CTGGTACCAACATGGCCGTCATGG-3' (SEQ ID NO: 39) and 5'-GGCTCGAGCGGCCGCTTAAAGCTCGT CTTTAAGGAAG-3' (SEQ ID NO: 40). After the gene fragments were obtained by PCR amplification, the A2-Her2E75 fragment was inserted into the polygene cloning sites of the pShttle-CMV vector (Agilent technologies, cat #24007) by using conventional gene cloning techniques in the art to obtain pShuttle-CMV-A2E75-SV40 pA. After the pShuttle vector plasmid carrying the foreign gene was purified, it was digested with Pme I enzyme (NEB Biolabs, cat #R0560s), and after purification, it was electrotransfected (Bio-Rad Gene Pulse) with an electroporator according to the manufacturer's instructions. The BJ5183-AD-1 bacterial strain (Agilent technologies, cat #200157) and the pShuttle vector plasmid carrying exogenous genes digested with Pme I were added into a 2 mm cuvette. 0.5 μg of plasmid was added to 50 μl of strain, and electrotransfection was performed under the conditions of 2500 v, 200 Ohms and 25 micro-FD. After culturing overnight on an LB culture plate containing 50 μg/ml of kanamycin, a small number of colonies were picked out and the plasmid was obtained for sequencing to determine whether there was any foreign gene fragment inserted into the adenovirus vector plasmid by recombination. The sequencing results are correct.

2) Preparation and Infection of Replication-Defective Recombinant Adenovirus Particles Expressing Labeling Polypeptide/HLA-A2

Virus particles were obtained by transfecting ADENO-X 293 cells (Takara, cat #632271) with Lipofectaine 3000 transfection reagent (Thermo Fisher Company, cat #L30-00001). ADENO-X 293 cells were cultured in a 6-well plate to reach 50-75% confluence and then transfection was performed. After the purified recombinant adenovirus plasmid was digested by Pac I (NEB Biolabs, cat #R0547s) and purified, the cells were transfected with Lipofectaine 3000 according to the manufacturer's instructions. After 24 hours, the old culture medium was replaced with fresh DMEN culture medium. Cytopathies began to appear in 10-14 days, showing the cells were suspended in spots. The cells were collected and suspended in a PBS solution, frozen and thawed 4 times in dry ice and a 37° C. water bath. The supernatant after centrifugation was the initial preparation of the virus and stored at −80° C. In order to obtain high-titer virus, ADENO-X 293 cells was cultured in a T75 culture dish (Corning, cat #430661), and 30%-50% of the initial virus cryopreservation solution was added after reaching 75% confluence. After the cytopathic changes occurred within 3-5 days, the cells were collected and frozen and thawed according to the above method to obtain a virus suspension. The virus titer was measured using an adenovirus titer kit (Takara, cat #632270) according to the manufacturer's instructions. When infecting target cells, the target cells was resuspended in fresh culture medium, the adenoviruses with a quantitative titer were added according to the number of cells, and the expression of foreign genes was detected after culturing for 3-4 days. The results showed that the foreign gene expression was positive.

Preparation Example 3: Preparation of Recombinant Oncolytic Adenovirus Expressing Labeling Polypeptide and Preparation of Recombinant Oncolytic Adenovirus Expressing Labeling Polypeptide/HLA-A2

1) Construction of Type 5 Oncolytic Adenovirus Vector

Firstly, the genomic DNA of H101 commercial oncolytic adenovirus (oncolytic adenovirus H101 purchased from Shanghai Sunway Biotech Co., Ltd.) was extracted as a template, and two primers (P26: 5'GGAAGATCTGGACT-GAAAATGAG3' (SEQ ID NO: 41) and P27: 5'TGAG GTCAGATGTA ACCAAGATTA 3'(SEQ ID NO: 42)) were designed. The E1A coding region of adenovirus type 5 was amplified by high-fidelity PCR. The size of the PCR product was 1173 bp. The obtained PCR fragment was purified and recovered upon BglII restriction enzyme digestion and ligated to a site between the BglII and EcoRV sites in the multiple cloning site of pShuttle-CMV vector (purchased from Agilent technologies, cat #24007) to obtain pShuttle-E1A. The E1A sequence was sequenced, confirming that the sequence was correct.

Figure 9:
FIG. 9 shows a schematic diagram of a main structure of the type 5 oncolytic adenovirus backbone vector pShuttle-MCS-CMV-E1A-SV40 pA constructed according to an embodiment of the present invention.

Two primers (P36: 5'CGCGTCGACTACTGTAATAGT-AATCAATTACG G3' (SEQ ID NO: 43) and P37: 5'GACGTCGACTAAGATACATTGATGAGTTTGGAC3') (SEQ ID NO: 44) were designed again, and the vector pShuttle-E1A was used as a template to amplify a 2017 bp DNA fragment including the CMV promoter, E1A coding region and SV40polyA sequence in the vector by high-fidelity PCR. The obtained PCR fragment was purified and recovered upon SalI digestion and ligated to the SalI site in the multiple cloning site on the pShuttle vector (purchased from Agilent, cat #240006) to obtain pShuttle-MCS-CMV-E1A-SV40polyA (FIG. 9). The CMV-E1A-SV40polyA sequence was sequenced, confirming that the sequence was correct.

Figure 10:
FIG. 10 shows a schematic diagram of a main structure of the type 5 oncolytic adenovirus genomic DNA (i.e., "OAd-E75", above) expressing the labeling polypeptide alone, and a schematic diagram of a main structure of the type 5 oncolytic adenovirus genomic DNA (i.e., "OAd-E75-A2", below) that co-expresses the labeling polypeptide and HLA-A2 constructed according to an embodiment of the present invention.
Figure 10:
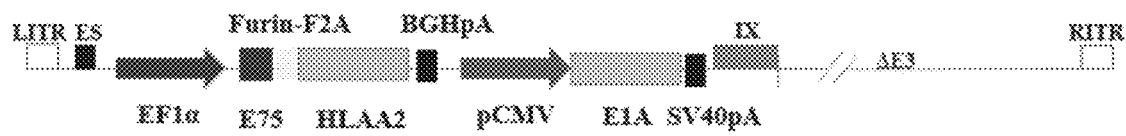

2) Preparation of genomic DNA of oncolytic adenovirus expressing Her2-E75 minigene (with KDEL at the C terminal) and preparation of genomic DNA of oncolytic adenovirus co-expressing Her2-E75 minigene (with KDEL at the C terminal) and HLA-A2 gene To the above resulting type 5 oncolytic adenovirus skeleton, a gene expression cassette that can express Her2-E75 minigene and a gene expression cassette that can co-express Her2-E75 minigene and HLA-A2 gene was added respectively, finally obtaining a genomic DNA of type 5 oncolytic adenovirus which can express Her2-E75 minigene alone ("OAd-E75") and a genomic DNA of type 5 oncolytic adenovirus which can co-express Her2-E75 minigene and HLA-A2 gene ("OAd-E75-A2") (see FIG. 10).

Among them, the target gene expression cassette includes three parts: EF-1α promoter, Her2-E75 minigene (or Her2-E75 minigene and HLA-A2) coding region sequence and BGHpolyA sequence. After obtaining the above two fragments, they were respectively inserted into the KpnI and XhoI sites on the type 5 oncolytic adenovirus backbone plasmid pShuttle-MCS-CMV-E1A-SV40 pA. The BGH-polyA sequence was amplified from pcDNA3.1 plasmid (purchased from Invitrogen) by high-fidelity PCR method. After obtaining the BGHpolyA fragment, it was inserted into the HindIII site on the type 5 oncolytic adenovirus backbone plasmid pShuttle-MCS-CMV-E1A-SV40polyA to obtain the pShuttle-EF1α-MCS-BGHpA-CMV-E1A-SV40 pA plasmid.

Cloning of E75 (Her2-E75 minigene, simply referred to as "E75" in this section) and E75-HLAA2 fragments Cloning of E75 Fragment Two primers (P105: 5' CCGCTCGAGATGAAAGGTTC-CATCTTCACATTG 3'(SEQ ID NO: 45) and P106: 5'CCGCTCGAGTTAAAGCTCGTCTTTAAGGAAGGC 3'(SEQ ID NO: 46)) were designed, and high-fidelity PCR was performed by using the CD811-EF1a-A2-F2A-HerE75 plasmid obtained in Preparation Example 1 as a template and the above primers, finally obtaining an E75 fragment containing XhoI restriction sites on both sides, with a size of 399 bp. The obtained PCR fragment was purified and recovered upon XhoI digestion and ligated to the XhoI site on the pShuttle-EF1a-MCS-BGHpA-CMV-E1A-SV40 pA vector to obtain pShuttle-EF1a-E75-BGHpA-CMV-E1A-SV40 pA. The E75 sequence thereof was sequenced and it was confirmed that the sequence was correct.

Cloning of E75-HLAA2 Fragment

The HLA-A2, Furin-F2A and E75 sequences in this part of the work were all amplified by high-fidelity PCR using the CD811-EF1a-A2-F2A-HerE75 plasmid as a template. In order to switch HLAA2 to the back of the Furin-F2A linker fragment and switch E75 to the front of the Furin-F2A linker fragment, firstly the HLAA2 fragment, Furin-F2A linker fragment and E75 fragment were amplified separately, and when amplifying the HLAA2 fragment, a stop codon need to be added to its end, while a stop codon need to be removed from the end of the E75 fragment. Finally, the three fragments were combined in sequence as planned by the overlap extension PCR method to obtain the E75-Furin-F2A-HLAA2 fragment. Firstly, 5 primers (P107: 5'TTCCG-GATCGCTTGGCACGAAGCTCGTCTTTAAGGAAGG 3'(SEQ ID NO: 47), P108: 5'CCTTCCTTAAAGACG-AGCTTCGTGCCA AGCGATCCGGAA 3'(SEQ ID NO: 48), P109: 5' CGGGGCGCCATGACGGCCATGGGCCC-AGGGTTGGACTC (SEQ ID NO: 49), P110: 5'GAGTC-CAACCCTGGGCCCATGGCCGTCATGGCGCCCC G 3'(SEQ ID NO: 50) and P111: 5'CTTCTCGAGT-CACACTTTACAAGCTGTGAGAG 3'(SEQ ID NO: 51)) were designed, and by using CD811-EF1a-A2-F2A-HerE75 plasmid as a template, two primers P105 and P107 were used for high-fidelity PCR amplification of the E75 fragment that did not contain a stop codon but contained part of the 5' end repeat sequence of the Furin-F2A linker fragment in which the fragment size was 406 bp; two primers P108 and P109 were used for high-fidelity PCR to amplify the Furin-F2A linker fragment including part of 3' end repeat fragment of the E75 and part of 5' end repeat fragment of the HLA-A2 in which the size of the fragment is 136 bp; two primers P110 and P111 were used for high-fidelity PCR to amplify a HLAA2 fragment including part of 3' end repeat fragment of Furin-F2A linker fragment, in which the fragment size is 1125 bp; then by using the PCR products of the E75 and Furin-F2A linker fragments as a template, the two primers P105 and P109 were used for high-fidelity PCR to amplify the E75-Furin-F2A fragment, in which the fragment size is 503 bp; then, by using the PCR products of E75-Furin-F2A and HLAA2 as templates, the E75-Furin-F2A-HLAA2 fragment was amplified by high-fidelity PCR using two primers P105 and P111 in which the fragment size is 1587 bp. The finally obtained PCR fragment of E75-Furin-F2A-HLAA2 was purified and recovered upon XhoI digestion and ligated into the XhoI site on the pShuttle-EF1a-MCS-BGHpA-CMV-E1A-SV40 pA vector to obtain pShuttle-EF1a-E75-HLA-A2-BGHpA-CMV-E1A-SV40 pA. The E75-HLAA2 fragment therein was sequenced, confirming that the fragment sequence was correct.

3) Obtaining the oncolytic adenovirus genomic DNA that expresses Her2-E75 minigene (with KDEL at the C-terminal) alone and the oncolytic adenovirus genomic DNA that co-expresses Her2-E75 minigene (with KDEL at the C-terminal) and HLA-A2 gene The pShuttle-EF1a-E75-BGHpA-CMV-E1A-SV40 pA and pShuttle-EF1α-E75-HLA-A2-BGHpA-CMV-E1A-SV40 pA plasmids (1 g each) obtained in the previous step, which have been sequenced and confirmed were PmeI digested, phenol/chloroform extraction and ethanol/ammonium acetate precipitation were carried out after reaction at 37° C. for 2-3 hours, rinsed with 70% ethanol for three times, the supernatant was discarded, and after drying at room temperature for 3 minutes, 10 µl of clean deionized water was added to completely dissolve the linearized DNA fragments; then 100 µl of BJ5183 (containing pAdEasy-1 plasmid) (purchased from Agilent) super-competent bacteria was added, mixed gently, placed on ice for 30 minutes, incubated at 42° C. for 90 seconds, then was put back on ice to continue incubation for 2 minutes, 500 µl of LB medium was added to each tube, and upon culturing with shaking at 37° C. and 150 RPM for 45 minutes, the resultant was spread on a kana-resistant LB plate, and cultured overnight at 37° C. On the next day, small clones appearing on the LB plate were picked and inoculated into 4 ml kana-resistant LB medium, and cultured at 37° C. and 200 RPM with shaking overnight. On the third day, the plasmid DNA of each tube of bacterial solution was extracted with a small amount of plasmid extraction kit. First, the obtained plasmid DNA was analyzed by agarose gel electrophoresis. The obviously smaller plasmid was discarded, and the larger plasmid was subjected to PacI digestion analysis. The correctly recombined pAdEasy plasmid will produce a smaller fragment of 4.5 kb or 3 kb after PacI digestion.

In this part, two plasmids with correct recombination were obtained (after PacI digestion, a smaller band with a size of 4.5 kb was produced): OAd-E75 and OAd-E75A2. The above two plasmids contain type 5 oncolytic adenovirus that was used for packaging and expressing Her2-E75 or co-expressing HLA-A2 and Her2-E75.

4) Packaging, amplification and purification of the oncolytic adenoviruses expressing Her2-E75 minigene (with KDEL at C-terminal) alone and the oncolytic adenoviruses co-expressing Her2-E75 minigene (with KDEL at C-terminal) and HLA-A2 gene Linearization of adenovirus genomic DNA: 2-3 µg of plasmid DNA (OAd-E75 and OAd-E75A2) obtained in the previous step were subjected to complete PacI digestion, reacted at 37° C. for 2-3 hours, and then subjected to phenol/chloroform extraction and ethanol ammonium acetate precipitation, the linearized DNA was rinsed with 70% ethanol twice and dried at room temperature for 3 minutes, and dissolved in 10 µl of clean deionized water. The DNA was used to directly transfect AD293 cells, or the linearized DNA was stored at −20° C. for later use.

Adenovirus packaging: The day before adenovirus packaging, the well-grown AD293 cells were seeded in a 6-well plate, and it is preferable for the cell density that the cell coverage rate was about 70% when the transfection experiment was carried out on the next day. The PacI linearized DNA was transfected into AD293 cells using Lipo2000 or a similar transfection reagent (the transfection reagent does not need to be removed). The DNA-transfected AD293 cells was put back into the CO₂ incubator and continued culturing for about 14 days until the AD293 cells float up after a large area of cytopathy appears, which represents successful packaging of the adenovirus. The diseased AD293 cells and virus mixture in the 6-well plate were pipetted to make them float completely, and then collected in a clean centrifuge tube. The cell suspension can be briefly shaken vigorously to release as much adenovirus as possible from the cells. The mixture can be stored at 4° C. for a short time and at −80° C. for a long time.

Amplification of adenovirus: The well-grown AD293 was inoculated into a 60 mm petri dish the day before amplification, and the cell coverage rate was about 80% when infected with adenovirus on the next day. About 1 ml of the adenovirus mixture collected from the 6-well plate was pipetted and directly added to a 60 mm petri dish inoculated with AD293. After slightly shaking and mixing homogenously, it was returned to the CO₂ incubator for proceeding with cultivation. After about 2-3 days, most of the cells may be observed as floating after cytopathy, the cells were pipetted as above to collect all the cell suspension in a clean centrifuge tube; then the collected 2 ml of virus suspension was added to a 10 cm petri dish with 80% coverage rate of AD293 cells, and after continuing cultivation in a CO₂ incubator for about 2-3 days, most of the cells can be seen as floating after cytopathy; the virus suspension was collected in the 10 cm petri dish; 2 ml of the virus suspension was pipetted and added to the 10 cm petri dish with 80% coverage rate of AD293 cells, and after continuing for cultivation in a CO₂ incubator for about 2-3 days, most of the cells can be seen as floating after cytopathy; the virus suspension was collected in the 15 cm petri dish, at this time the adenovirus titer in the cell supernatant reaches about $10^8$ PFU/ml. At this point, a large amount of adenovirus can be amplified using the virus suspension in a 15 cm petri dish. Usually, it is necessary to amplify and collect 40-80 cell suspensions in 15 cm petri dishes according to experimental needs and virus yield before conducting CsCl density gradient centrifugal purification of adenovirus amplification.

Adenovirus purification: After the virus suspension collected in the previous step was centrifuged, it was divided into two parts: the supernatant and the cell pellet. The adenoviruses in the supernatant were precipitated using PEG8000/NaCl and resuspended in 10 mM Tris·Cl (pH8.0); the cell pellet was resuspended in 10 mM Tris·Cl (pH8.0) and frozen and thawed for 3-5 times so as to completely release the adenoviruses in the cell. The cell suspension was centrifuged again, and the supernatant was kept for the subsequent CsCl density gradient centrifugal purification. Next, the obtained adenovirus suspension was centrifuged twice with light CsCl (1.2 g/ml) and heavy CsCl (1.45 g/ml), and the Ad white band after the second centrifugation was drawn with a syringe. Finally, the CsCl that dissolves the adenovirus was replaced by the PD-10 desalting column with the adenovirus preservation solution (10 mM Tris (pH7.4), 1 mM MgCl₂, 10% Glycerol, filtered, sterilized and stored at 4° C.), and stored at −80° C. after aliquoting.

The titration of adenovirus titer: The titration of adenovirus titer was carried out by using an adenovirus titer titration kit. The basic principle is to infect AD293 cells with the adenovirus after diluting the adenovirus at an appropriate titer, and then detect the expression of Hexon protein on the cell surface after 48 hours. The titer of active adenovirus (PFU/ml) was determined by counting the number of cells expressing Hexon protein in a specified area.

5) Detection of HLAA2 Protein Expression in Adenovirus

The HLAA2-negative cell line (SKOV3) was selected, and the cells were seeded in a 24-well cell culture plate the day before the experiment. On the next day, adenoviruses OAd-E75 and OAd-E75A2 were added to the wells of inoculated cells according to different multiplicity of infection (MOI=5, 10, and 20). In this experiment, H101 was used as a negative control virus. After mixing homogenously and continuing cultivation in a CO₂ incubator for 48 hours, the cells were recovered, and the cells incubated with anti-HLAA2 flow cytometry antibody according to the conventional FACS process, and then analyzed on the machine. The expression of HLA-A2 on the surface of SKOV3 cells was finally determined, and the result was positive.

Example 1: Induction of Her2/Neu 369-377 Polypeptide (Her2-E75 Epitope Polypeptide) Specific Cytotoxic T Cells from HLA-A2 Positive Normal Donor Peripheral Blood In this example, the polypeptide-specific cytotoxic T cells were induced using a low concentration of 1 µg/ml of Her2/neu 369-377 polypeptide from HLA-A2-positive normal PBMCs (#2) after two cycles of in vitro stimulation, and flow cytometric analysis and single cell separation were performed. The specific method is as described above. The results are as follows:

The right panel of FIG. 1A shows that 0.024% of lymphocytes are CD8-positive killing T cells that can bind to Her2/neu 369-377/HLA-A2 pentamer (Her2-E75 pentamer). The control cells without Her2 polypeptide-stimulation in the left panel did not show CD8-positive pentamer-positive cells. The results show that in the natural T cell bank, the number of specific T cells that recognize the Her2/neu 369-377 antigen polypeptide is very small. Despite the small number, this group of T cells that can recognize the Her2/neu 369-377 polypeptide can still be clearly distinguished. In addition, according to the fluorescence intensity of the bound Her2-E75 pentamer, the positive cells contained high-affinity T cells and low-affinity T cells. After separating 300 CD8-positive pentamer-positive cells by flow cytometry, they were cultured monoclonally. After two cycles of antigen peptide restimulation and cytokine amplification, a proliferated T cell clone Her2 CTL clone 6A5 (referred to as Her2 CTL 6A5) was obtained from the 300 isolated single T cells. The right panel of FIG. 1B shows that 97.9% of CD8+ CTL cells can bind to Her2/neu 369-377/HLA-A2 tetramer (i.e., Her2-E75 tetramer), showing that this purified T cell clone is not mixed with other unrelated cells. The left panel shows control T cells that cannot bind to Her2-E75 tetramer.

Example 2: Obtaining a Full Sequence of Her2/Neu 369-377 Polypeptide-Specific TCR In this example, total RNA was purified directly from a certain number of Her2 CTL 6A5 cells obtained in Example 1, and the paired α chain and β chain gene sequences of TCR were obtained by 5-RACE RT-PCR method (that is, the two chains can jointly form a functional TCR that recognizes the antigen polypeptide), and the TCR encoded thereby is called "Her2 TCR-6A5". The amino acid sequence of the a chain of the TCR is shown in SEQ ID NO: 4, the coding sequence is shown in SEQ ID NO: 12, and the amino acid sequence of the β chain of the TCR is shown in SEQ ID NO: 7, and the coding sequence is shown in SEQ ID NO: 15. This TCR exists in the peripheral T cell pool of HLA-A2-positive normal people, and will not cross-react with normal cells that slightly express the Her2/neu protein to cause autoimmune reactions. In order to test the antigenic specificity and function of the obtained TCR, the α chain and β chain sequences of TCR were cloned into a replication-defective lentiviral expression vector. FIG. 1C shows a schematic diagram of the constructed TCR lentiviral vector structure fragment. The constant regions of the α chain and β chain sequences of TCR are changed to murine sequences from human sequences, and are connected by a cleavable linker polypeptide. The expression of α chain and β chain of 6A5 TCR is driven by the EF-1α promoter. This promoter is a highly expressed promoter in eukaryotic cells, and will not be affected by methylation and other factors to cause loss of function, and is suitable for long-term expression of foreign genes in vivo. The α chain and β chain of TCR are connected by F2A polypeptide sequence therebetween. The α chain gene and β chain gene of TCR can be transcribed at the same time, and translated through ribosome skipping, so that the α chain and β chain of TCR polypeptides are separated from each other. This ensures the consistency of the expression of the α chain and β chain of TCR, so as to form a TCR dimer more efficiently. There is a furin digestion site between the α chain and β chain of TCR, which is used to remove excess peptides at the carboxylic terminal of the β chain.

The nucleotide sequences of the β chain and α chain of the TCR (SEQ ID NO: 20) (corresponding TCR is Her2 TCR-6A5-mC and the amino acid sequence is as shown in SEQ ID NO: 23), which is linked by the cleavable linker polypeptide and the human sequence of the constant region is replaced with murine sequence, were connected to the above vector so as to obtain the Her2 TCR-6A5-mC recombinant lentiviral vector. The Her2 TCR-6A5-mC gene fragment was amplified by PCR and cloned into the downstream of the EF1-promoter of the above-mentioned lentiviral vector (i.e., pCDH-EF1α-MCS): p fragment of Her2 TCR-6A5-mC carrying the mouse constant region sequence was obtained by amplifying 5' primer 5'-AGAGCTAGCGAAT-TCAACATGGGCTGCAGGCTGCTC-3' (SEQ ID NO: 52) and 3' primer 5'-GGATCGCTTGGCACGTGAAT-TCTTTCTTTTGACCATAGCCAT-3' (SEQ ID NO: 53); the α gene fragment of Her2 TCR-6A5-mC carrying the murine constant region sequence was obtained by amplifying 5' primer 5'-TCCAACCCTGGGCCCATGCTCCTGTTGCT-CATACCAGTG-3' (SEQ ID NO: 54) and 3' primer 5'-GTT-GATTGTCGACGCCCTCAACTGGACCACAGCCT-3' (SEQ ID NO: 55). Q5 high-fidelity PCR kit (NEB, cat #M0543S) was used for PCR. The reaction conditions are: 98° C. for 30 seconds, then 25 cycles: 98° C. for 10 seconds, 65° C. for 10 seconds, and 72° C. for 3 minutes. The obtained TCR fragment was cloned into the MCS region downstream of the EF1α promoter of the pCDH-EF1α-MCS vector.

The respective recombinant TCR lentiviral particles were prepared using the constructed recombinant TCR lentiviral expression vector according to the aforementioned method.

Figure 2:
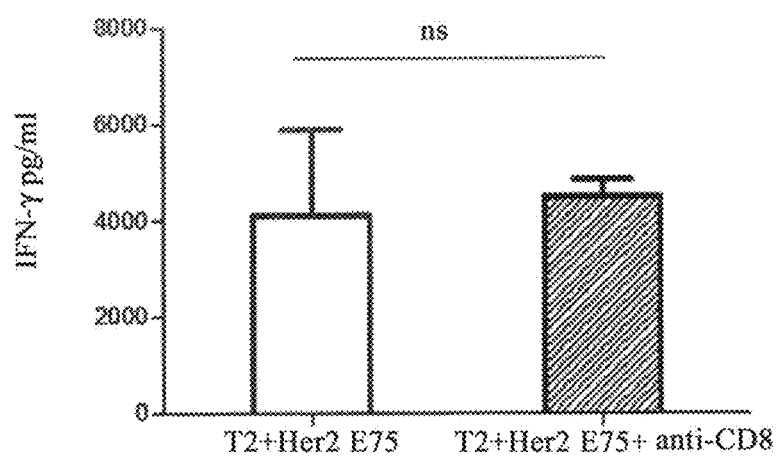
FIG. 2 shows the phenotype and functional detection results of peripheral blood monocyte cells (PBMCs) transfected with the Her2 TCR-6A5-mC TCR gene.

Example 3: Normal Peripheral Blood T Cells are Transfected with Her2 TCR-6A5-mC Recombinant Lentivirus to Express a Specific TCR that can Recognize Her2/Neu 369-377 Polypeptide In order to further verify whether the TCR obtained in the present invention can be expressed in primary T cells and has the function of recognizing Her2/neu antigen polypeptides, the CD3/CD28 antibody activated peripheral blood T cells from two different normal donors were transfected with the recombinant lentiviral particles carrying the Her2 TCR-6A5-mC gene (Her2 TCR-6A5-mC recombinant lentiviral vector). After 14 days, the cells were collected for Her2-E75 tetramer staining. The specific method is as described above. The results are as follows:

FIG. 2A showed that the two donor peripheral blood monocyte cells (#1 PBMC and #2 PBMC, respectively) have lymphocytes that can bind to Her2-E75 tetramer, indicating that the Her2 TCR-6A5-mC expressed by these cells can specifically recognize the Her2/neu antigen polypeptide presented by HLA-A2. The results also showed that the $CD8^+$ T killer cells was similar to that of $CD8^-$ lymphocytes in terms of a positive rate among Her2-E75 tetramer positive cells (that is, Her2 TCR-6A5-mC was expressed). $CD8^-$ lymphocytes are likely to be $CD4^+$ T helper cells. If the transfection efficiency at which $CD8^+$ and $CD4^+$ T cells are infected by the lentivirus is the same, it means that the exogenous Her2/neu 369-377 specific TCR on $CD4^+$ cells can effectively bind Her2-E75 tetramer. This further showed that the transfected Her2 TCR-6A5-mC can effectively bind to the Her2/HLA-A2 complex even without requiring the auxiliary function of the CD8 molecule, that is, recognition of Her2 TCR-6A5-mC to Her2/neu 369-377 epitope polypeptide presented by HLA-A2 is CD8 independent. CD4 cells expressing Her2 TCR-6A5-mC TCR recognize Her2 antigen and then secrete cytokines, which can not only facilitate the function of the cytotoxic T cells and extend survival time in the body, but also induce specific T cells against endogenous tumor antigens by regulating the tumor microenvironment, thereby enhancing anti-tumor immunity.

10e5 TCR-transfected PBMCs were added to each well of a 96-well plate, and after mixing with Her2/neu 369-377 antigen polypeptide at the different concentrations (Her2/neu 369-377 antigen peptides were diluted 10-fold from 0.1 μg/ml to obtain different groups with final concentrations of 0.1 μg/ml, 0.01 μg/ml, 0.001 μg/ml and 0.0001 μg/ml) presented by T2 cells (1×10e5 per well), the IFN-γ secreted by T cells in the supernatant was detected to confirm the function of the TCR-expressed PBMCs in specifically recognizing Her2/neu 369-377 polypeptide. FIG. 2B shows that PBMCs expressing Her2 TCR-6A5-mC can be activated by the Her2/neu 369-377 antigen polypeptide presented by T2 cells to secrete IFN-γ, indicating that the primary T cells expressing exogenous Her2 TCR-6A5-mC can specifically recognize the Her2/neu 369-377 polypeptide presented by HLA-A2 molecules. The ability to recognize antigenic polypeptides is related to the amount of exogenous TCR expressed on T cells. The half-maximum reaction (EC50) peptide concentration of the recognized antigen peptide by the two different donor PBMCs transfected with Her2 TCR-6A5-mC is approximately 1.6 ng/ml and 2.9 ng/ml, respectively, by curve fitting calculation (IC50 Tool program, world wide web ic50.tk). Although the sensitivity of this reaction is lower than EC50 (EC50 is about 10e-10M) of high-affinity TCR that recognizes foreign antigens such as viral antigens (see "CANCER RESEARCH 1998, 58. 4902-4908" and "HUMAN GENE THERAPY 2014, 25:730-739"), it is still within the mid-to-high affinity range of TCR that can recognize common tumor-associated antigens (as described in "Eur J Immunol (2012) 42:3174-9").

FIG. 2C shows that addition of the anti-human CD8 antibody when T cells were co-cultured with antigen polypeptides presented by T2 cells ($T2^+$ Her2-E75, that is, Her2/neu 369-377 polypeptide) did not significantly inhibit the function of T cells to secrete IFN-γ. This indicates that the function of the exogenous TCR to recognize the Her2/neu 369-377 antigen polypeptide does not require the auxiliary role of the CD8 molecule, and also shows that the recognition function of the Her2 TCR-6A5-mC TCR of the present invention is a CD8 function-independent TCR.

Figure 3:
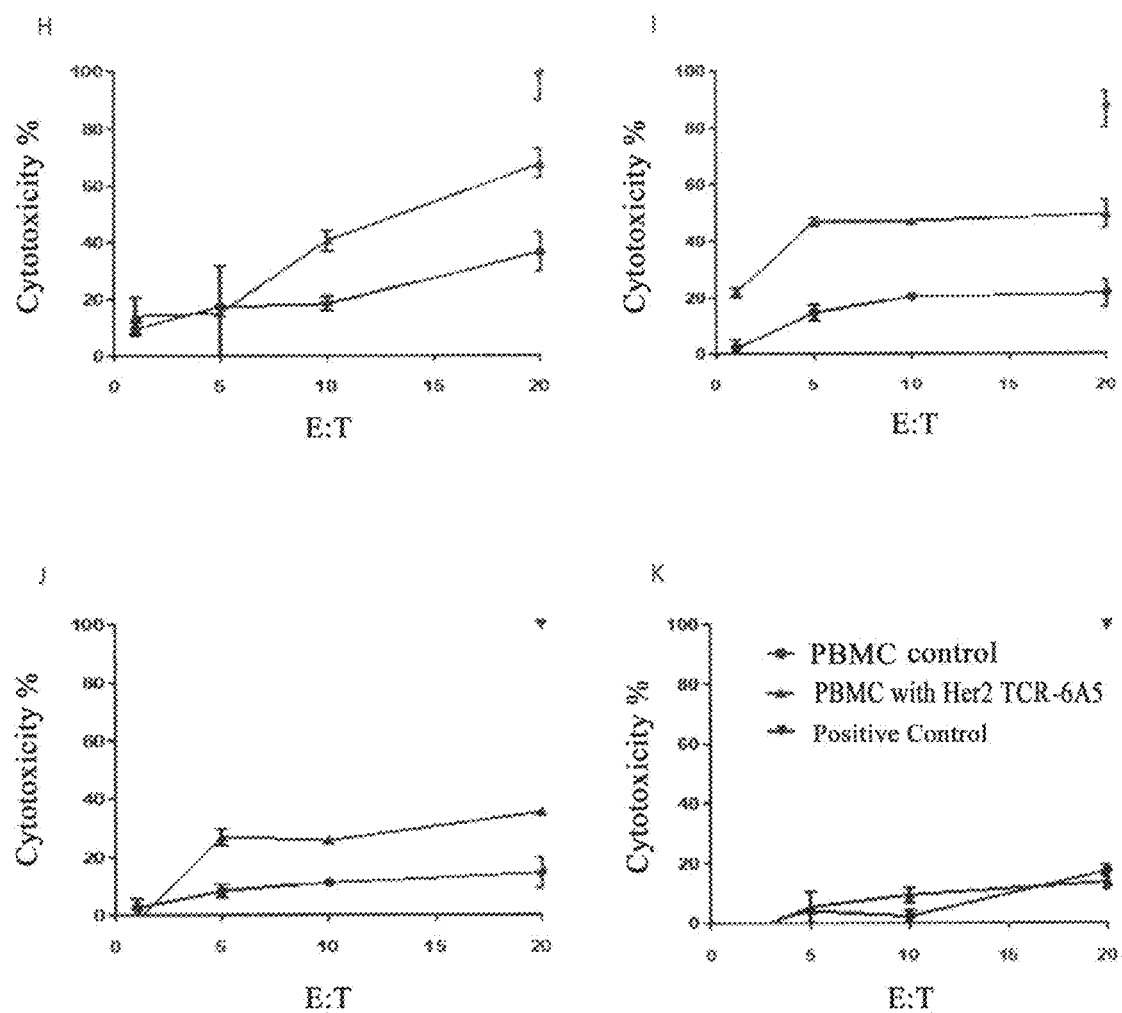
FIG. 3 shows the functional detection results of the peripheral blood monocyte cells (PBMCs) transfected with the Her2 TCR-6A5-mC TCR gene in recognizing tumor cell strains.

Example 4: The Her2/Neu 369-377 Polypeptide-Specific TCR Expressed by Normal Peripheral Blood T Cells Transfected with Her2 TCR-6A5-mC Recombinant Lentivirus can Recognize HLA-A2$^+$ Her2/Neu$^+$ Tumor Cells Firstly, the expression of HLA-A2 and Her2/neu was detected in the selected tumor cell strains. The tumor cell strains include colorectal cancer Colo205 and HCT116, breast cancer MDA-MB-231 and MCF-7, pancreatic cancer PANC-1, glioma U87MG, and small cell lung cancer NCI-H446. The tumor cells were stained with anti-HLA-A2 antibody (BD Bioscences, cat #561341) and anti-human CD340 (erbB2) antibody (Biolegend, cat #324406) and then analyzed by flow cytometry. The results in FIG. 3A show that Colo205, MDA-MB-231, MCF-7, HCT116, and PANC-1 are all HLA-A2$^+$ Her/neu$^+$; U87MG is HLA-A2$^+$, Her2/neu$^-$, NCI-H446's HLA-A2 and Her2/neu are both negative. These tumor cell strains not only originate from different tissues, but also express differently HLA-A2 and Her2/neu. Among them, U87MG and NCI-H446 cells can be used as negative controls for Her2 TCR-6A5-mC T cell function testing.

After adding 1×10e4 tumor cells to each well of the 96-well plate, a certain amount of PBMCs transfected with Her2 TCR-6A5-mC TCR were added to each well of the 96-well plate, or PBMCs not transfected with Her2 TCR-6A5-mC TCR were added as a control group based on the E:T ratio (5:1). The E:T ratio is 5:1. T cells were mixed and cultured with different tumor cell strains, and then the IFN-γ secreted in the supernatant was detected. The specific method is as described above. The results are as follows:

FIG. 3B shows that T cells expressing Her2 TCR-6A5-mC can be activated by HLA-A2$^+$ Her2/neu$^+$ tumor cell strains and secrete IFN-γ. The tumor cell strains include colon cancer Colo205 and HCT116, breast cancer MDA-MB-231 and MCF-7, pancreatic cancer PANC-1. However, the control group HLA-A2$^+$ Her2/neu$^-$ glioma U87MG and HLA-A2$^-$ Her2/neu$^-$ lung cancer NCI-H446 cannot activate the T cells transfected with Her2 TCR-6A5-mC, indicating that Her2 TCR-6A5-mC TCR can specifically recognize the Her2/neu antigen presented by HLA-A2 on the surface of tumor cells. Control T cells derived from the same donor PBMCs and cultured in parallel but not transfected with Her2 TCR-6A5-mC cannot be activated by the listed tumor cell strains, indicating that the response to tumor cells is not non-specific. The results also show that the ability of Her2 TCR-6A5-mC T cells to recognize the Her2/neu antigen presented by HLA-A2 is not closely related to the expression level of HLA-A2 and Her2/neu molecules on the surface of tumor cells. Different tumor cells may have different inhibitory effects on T cells. On the other hand, the expression level on the cell surface does not necessarily reflect the total expression level of Her2/neu. Some tumor cells express Her2/neu that mainly exists in the cell cytoplasm. These antigens are more easily presented by HLA-A2 (see "J Immunol 2006; 177:5088-5097").

1×10e4 target cells were added to each well of the culture plate, and a certain amount of PBMCs transfected with TCR gene were added based on the set E:T ratio (1:1, 5:1, 10:1, 20:1, 40:1), and the killing activity of T cells on tumor cells was measured 24 hours later. FIG. 3C-K shows that compared with control T cells without transfected TCR, the T cells expressing Her2 TCR-6A5-mC TCR can specifically recognize and kill HLA-A2$^+$ Her2/neu$^+$ tumor cell strains MCF-7, HCT116, PANC-1 and HEPG-2. The killing ability has a dose-effect relationship with the number of Her2 TCR-6A5-mC T cells. However, the control group HLA-A2$^+$ Her2/neu$^-$ glioma U87MG, HLA-A2$^-$ Her2/neu$^+$ SKOV3 and HT-29, and HLA-A2$^-$ Her2/neu$^-$ lung cancer NCI-H446 cannot be specifically killed by Her2 TCR-6A5-mC T cells. The results also show that when Her2 TCR-6A5-mC T cells increase to a certain number, they exhibit significant specific recognition and killing ability to HLA-A2$^+$ Her2/neu$^+$ tumor cells. When the E:T ratio is less than 10:1, the specific killing ability is not significant, which may be related to the number of Her2/neu epitope peptides presented by HLA-A2 on the surface of tumor cells. In order to further enhance the recognition and killing sensitivity of Her2 TCR-6A5-mC T cells to tumor cells, one strategy is to increase the amount of HLA-A2 and Her2/neu expressed by the tumor target cells.

Example 5: Transfection of Gene Vectors Expressing HLA-A2 and Her2/Neu Epitope Polypeptides Allows Target Cells to Express Exogenous HLA-A2 and Her2/Neu Epitope Polypeptides In order to further enhance the recognition and killing sensitivity of Her2 TCR-6A5-mC T cells to tumor cells, it can be achieved by making the tumor cells express exogenous Her2/neu antigen, thereby increasing the Her2/neu epitope presented by HLA-A2. Since the expression of endogenous HLA class I molecules is often low or missing in tumor cells, the transfection vector can simultaneously express the exogenous HLA-A2 gene to increase the expression level of HLA class I molecules. In addition, the tumor cells often have functional defects in the HLA class I antigen presentation pathway. As a result, the tumor antigen proteins cannot be effectively degraded into epitope polypeptides and presented to the cell surface by HLA class I molecules. If the epitope polypeptide is directly introduced into the endoplasmic reticulum through a signal peptide, it will not undergo protease degradation in the cytoplasm and the transport of TAP molecules. The epitope polypeptide can directly form a complex with the HLA molecules and β2 microglobulin in the endoplasmic reticulum, and then the complex is presented to the surface of tumor cells. The minigenes expressing epitope polypeptides can be linked by the digestion fragments of Furin enzyme to form multiple minigenes of epitope polypeptides in tandem. After entering the endoplasmic reticulum, the minigenes are cleaved by furin enzyme so as to release more epitope peptides. Adding the KDEL fragment of the endoplasmic reticulum retention signal at the terminal of the tandem epitope polypeptide chain can prevent the epitope polypeptide chain from being transported to the downstream secretory organelles, thereby increasing the possibility of forming HLA/polypeptide complexes.

Figure 4:
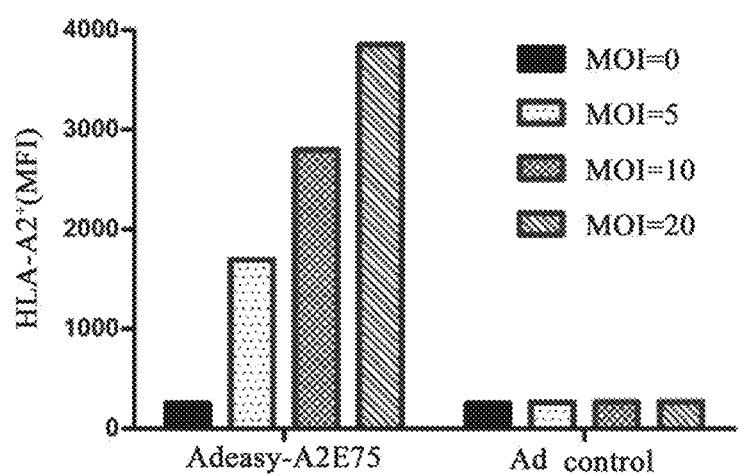
FIG. 4 shows that the target cells transfected with a vector carrying the HLA-A2 gene and Her2-E75 minigene can express HLA-A2, and the expressed Her2-E75 polypeptide can be combined with HLA-A2 to form an antigen complex recognized by Her2 TCR-6A5-mC TCR.
Figure 4:
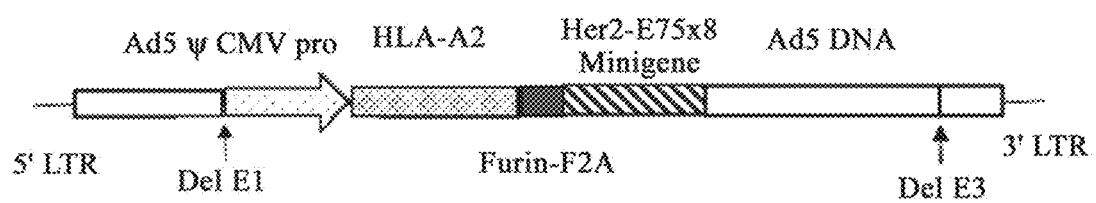

Three lentiviral vector plasmids were prepared according to the method of Preparation Example 1: "pCDH-EF1p-A2-PKGp-E75×1" (carrying HLA-A2 coding sequence and one Her2-E75 epitope polypeptide coding sequence), "pCDH-EF1p-A2-PKGp-E75×4" (carrying HLA-A2 coding sequence and four repeated Her2-E75 epitope polypeptide coding sequences) and "pCDH-EF1p-A2-PKGp-E75×8" (carrying the HLA-A2 coding sequence and eight repeated Her2-E75 epitope polypeptide coding sequences) which are collectively referred to as "pCDH-EF1p-A2-PKGp-E75 vector". The upper panel of FIG. 4B is a schematic diagram of the overall structure of a lentiviral vector containing HLA-A2 and Her2/neu epitope polypeptide (Her2-E75) minigene (pCDH-EF1p-A2-PKGp-E75 vector). HLA-A2 is driven by the EF-1α promoter, and the epitope polypeptide (shown as Her2-E75 in the figure) minigene is driven by the PKG promoter. The lower panel of FIG. 4B is a schematic diagram of the constitution of the Her2/neu epitope polypeptide minigene in "pCDH-EF1p-A2-PKGp-E75×8", showing eight Her2-E75 epitope polypeptides connected by the cleavage site of Furin enzyme (Her2-E75×8 minigenes).

The three lentiviral plasmid vectors constructed above were respectively transfected into 293T cells, which are used as target cells to detect the recognition function of Her2 TCR-6A5 T cells. 293T cells are human kidney epithelial cell strains and are HLA-A2 negative and Her2/neu negative. PBMCs transfected with Her2 TCR-6A5-mC TCR and 293T cells transfected with pCDH-EF1p-A2-PKGp-E75 were mixed and cultured, and the E:T ratio was 10:1. After 24 hours, the supernatant was collected to detect IFN-γ secretion. The number of epitope polypeptide minigenes on plasmid pCDH-EF1p-A2-PKGp-E75 is 1, 4 and 8, respectively (shown as 293-A2-PKG-E75×1, 293-A2-PKG-E75×4, and 293-A2-PKG-E75×8). 293T cells without transfecting plasmid were used as the negative control group (shown as the 293 control in the figure), and T2 cells that present 0.1 µg/ml of Her2/neu 369-377 antigen peptide were used as the positive control group (shown as T2+Her2-E75 in the figure)). FIG. 4A shows that Her2 TCR-6A5-mC T cells can specifically recognize 293T cells transfected with plasmid vectors expressing HLA-A2 and Her2/neu epitope polypeptides and secrete IFN-γ, indicating HLA-A2 and Her2/neu 369-377 epitope polypeptides are both expressed by 293T and presented to the cell surface in the form of HLA/polypeptide complexes to be recognized by Her2 TCR-6A5-mC TCR. In addition, as the number of epitope polypeptides in minigenes increases, the recognition activity of T cells is enhanced accordingly, indicating that the number of HLA-A2/epitope polypeptide complexes presented on the cell surface can be increased as the expression of Her2/neu epitope polypeptide increases.

In order to enable the replication-defective adenovirus vector to express HLA-A2 and Her2/neu epitope polypeptides, the HLA-A2 gene and Her2/neu epitope polypeptide minigene (with KDEL at the C terminal) are loaded into the E1 region of adenovirus type 5 vector. The replication-defective adenovirus Adeasy-A2-Her2 E75 (referred to as "Adeasy-A2E75") was prepared according to the method described in Preparation Example 2, which is replication-defective adenovirus expressing HLA-A2 and eight Her2/neu epitope polypeptides. The schematic diagram of the vector is shown in FIG. 4D (Adeasy-A2E75 vector). This adenovirus vector is derived from an adenovirus type 5 that was deleted in E1 and E3 sequences (see "Nature Protocols 2007; 2: 1236-1247"). The expression of HLA-A2 gene and Her2/neu epitope polypeptide minigene is driven by exogenous CMV promoter. HLA-A2 gene and Her2/neu epitope polypeptide minigene are separated by the cleavable fragment Furin enzyme recognition fragment and F2A fragment. In this way, on the one hand, it can ensure that the expression levels of HLA-A2 and Her2/neu epitope polypeptides are similar. The length of the nucleic acid sequence of the foreign gene can also be kept within the size range of the foreign gene which is allowed to be loaded by the adenovirus genome. In addition, a KDEL fragment of the ER retention signal was added to the terminal of the tandem epitope polypeptide chain to increase the possibility of forming HLA/polypeptide complexes. Since the E3-19K protein inhibits the antigen presentation function of HLA, the adenovirus lacking the sequence of the E3 region will not interfere with the presentation of the expressed foreign epitope polypeptide after infecting cells.

In order to verify whether the replication-defective adenovirus vector Adeasy-A2-Her2 E75 expresses foreign genes, the ovarian cancer cells SKOV3 were infected with Adeasy-A2-Her2 E75 adenovirus particles. SKOV3 cells are HLA-A2 negative. The expression of HLA-A2 on the surface of SKOV3 cells may be used to determine whether the Adeasy-A2-Her2 E75 adenovirus vector can express foreign genes. The SKOV3 cell strain was cultured in a 10 cm petri dish, digested with trypsin digestion solution when its confluence was about 80%, washed with culture medium one time, centrifuged, resuspended with culture medium McCony5A (Gibco #16600-082), and then plated into a 24-well plate, 1×10e5 per well, 500 µl medium per well; after 24 hours, Adeasy-A2-Her2 E75 adenovirus was added, the same volume of virus preparation solution at 0 MOI, 5 MOI, 10 MOI, 20 MOI was added, and continued to culture for 24 hours. Then, the supernatant was discarded, the cells were harvested after digesting the cells with trypsin, and resuspended in a 1.5 ml of EP tube with 100 µl of PBS, and 2 µl of APC-anti-human HLA-A2 antibody (BD #561341) was added to each tube. After incubating for 30 minutes, and then washing with 1% BSA in PBS, flow cytometric testing was performed, and Flowjo software was used for analysis after testing. FIG. 4C shows that SKOV3 cells can express HLA-A2 24 hours after infection with Adeasy-A2-Her2 E75 adenovirus. There is a dose-effect relationship between the expression level of HLA-A2 and the titer of the used virus, while SKOV3 cells infected with control adenovirus that does not express foreign genes (shown as the Ad control in the figure) do not express HLA-A2, indicating that adenovirus carrying the HLA-A2 gene and the Her2/neu epitope polypeptide minigene can effectively express foreign HLA-A2 molecules.

Example 6: Infecting Tumor Cells with a Replication-Defective Adenovirus Expressing HLA-A2 and Her2/Neu Epitope Polypeptide Minigenes can Significantly Enhance the Recognition and Killing Sensitivity of Her2 TCR-6A5-mC T Cells to Tumor Cells To further verify whether the replication-defective adenovirus vector Adeasy-A2-Her2 E75 increases the number of HLA-A2/Her2 epitope polypeptide complexes that can be recognized by Her2 TCR-6A5-mC T cells after infecting tumor cells, so as to enhance the recognition and killing sensitivity of T cells to tumor cells, the tumor cell strains SKOV3, MCF-7 and NCI-H446 were respectively infected with Adeasy-A2-Her2 E75 adenovirus. After 24 hours, they were mixed with PBMCs transfected with Her2 TCR-6A5-mC TCR and co-cultured for additional 24 hours, and the function of Her2 TCR-6A5-mC T cells to specifically secrete IFN-γ and kill target cells was tested.

Figure 5:
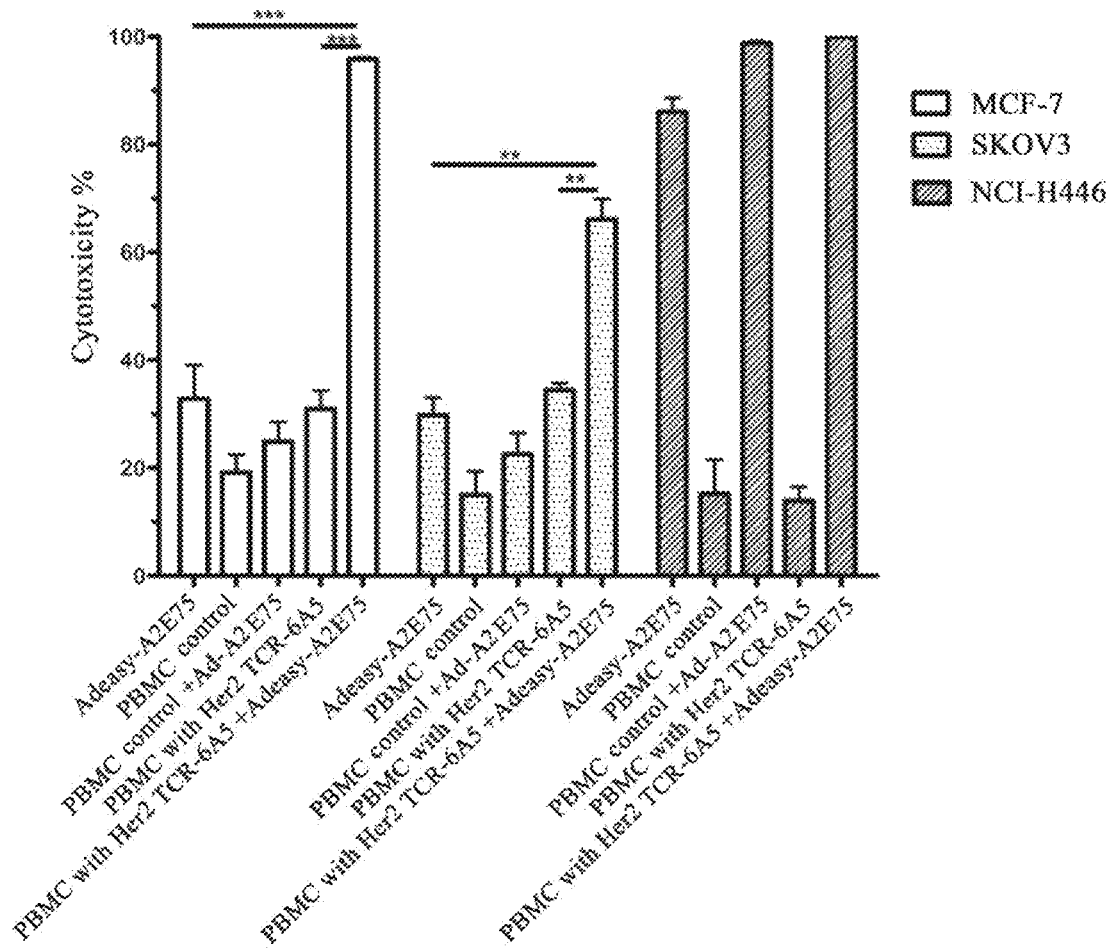
FIG. 5 shows that the replication-defective adenovirus carrying the HLA-A2 gene and Her2-E75 minigene can increase the recognition sensitivity of Her2 TCR-6A5-mC TCR to different target cells after infecting tumor cells.

FIG. 5A shows that the tumor cells infected with Adeasy-A2-Her2 E75 adenovirus can significantly stimulate Her2 TCR-6A5-mC T cells to specifically secrete IFN-γ. The MOI of the adenovirus that infects tumor cells is 10, and the E:T ratio thereof with the co-cultured PBMCs transfected with Her2 TCR-6A5-mC TCR is 5:1. The tumor cell strains are HLA-A2$^+$ Her2/neu$^+$ MCF-7 cells, HLA-A2$^-$ Her2/neu$^+$ SKOV3 cells and HLA-A2$^-$ Her2/neu$^-$ NCI-H446 cells. The results showed that after the tumor cells were infected with Adeasy-A2-Her2 E75 adenovirus alone, they hardly secreted IFN-γ (experimental group "Adeasy-A2E75"). The PBMCs transfected with Her2 TCR-6A5-mC TCR at lower E:T ratio cannot effectively recognize HLA-A2$^+$ Her2/neu$^+$ MCF-7 cells and secrete IFN-γ (experimental group "PBMC with Her2TCR-6A5"). For SKOV3 cells, the PBMCs transfected with Her2 TCR-6A5-mC TCR ("PBMC with Her2TCR-6A5") cannot specifically secrete IFN-γ compared with control PBMC (experimental group "PBMC control"), either. However, when tumor cells were infected with Adeasy-A2-Her2 E75 adenovirus, the recognition function of Her2 TCR-6A5-mC T cells can be significantly enhanced, regardless of whether the tumor cells express endogenous HLA-A2 and Her2/neu (experimental group "PBMC with Her2TCR-6A5+Adeasy-A2E75"). In each target cell group, Her2 TCR-6A5-mC T cells were significantly more active in recognizing tumor cells infected with Adeasy-A2-Her2 E75 adenovirus than non-infected target cells (p<=0.001). However, Adeasy-A2-Her2 E75 adenovirus infected tumor cells cannot increase the recognition activity of control PBMCs that have not been transfected with Her2 TCR-6A5-mC TCR (experimental group "PBMC control" and experimental group "PBMC control+Adeasy-A2E75"), indicating that the increase in secretion of IFN-γ after adenovirus infection is produced by enhancing the recognition activity of Her2 TCR-6A5-mC TCR on tumor cells. The results show that after Adeasy-A2-Her2 E75 adenovirus infects the tumor cells, it not only makes HLA-A2-negative cells SKOV3 and NCI-H446 express exogenous HLA-A2, but it can also increase the expression of Her2/neu epitope polypeptide mini-genes. The number of HLA-A2/Her2/neu 369-377 polypeptide complexes recognized by Her2 TCR-6A5-mC T cells on the surface of tumor cells is increased, thereby enhancing the recognition sensitivity of Her2 TCR-6A5-mC T cells.

In order to further verify whether the replication-defective adenovirus vector Adeasy-A2-Her2 E75 increases the killing ability of Her2 TCR-6A5-mC T cells to target cells after infection of tumor cells, the tumor cell strains SKOV3, MCF-7 and NCI-H446, respectively, were infected with Adeasy-A2-Her2 E75 adenovirus. After 24 hours, they were mixed with PBMCs transfected with Her2 TCR-6A5-mC TCR and co-cultured for additional 24 hours. The number of surviving adherent living cells was detected by Trypan blue to determine killing ability of T cells on target cells. The MOI of the virus that has infected tumor cells is 10, and the E:T ratio of mixed culture is 8:1.

FIG. 5B shows that after Adeasy-A2-Her2 E75 adenovirus infects tumor cells alone, it can cause the cell death of most NCI-H446 cells (the experimental group "Adeasy-A2E75" with the target cells NCI-H446). This may be because the replication-defective adenovirus with deletion of E1/E3 can sometimes cause apoptosis of certain cells, especially when the infection titer is high (see "Gene Ther. 1999 June; 6(6):1054-63"). The adenovirus-infected NCI-H446 cells shown in FIG. 5A can stimulate Her2 TCR-6A5-mC T cells mixed and co-cultured with them to secrete IFN-γ, but since this target cell is too sensitive to Adeasy-A2-Her2 E75, it is temporarily impossible to determine in the test results shown in FIG. 5B whether the target cell death is resulted from the killing of Her2 TCR-6A5-mC T cells on the target cells infected with adenovirus or the apoptosis induced by adenovirus (the experimental group "PBMC with Her2 6A+Adeasy-A2E75 5" with the target cells NCI-H446). However, it can be seen from FIG. 5B that in case that the target cells in the experiment are MCF-7 cells, the cell killing rate when the replication-deficient adenovirus expressing HLA-A2 and Her2 E75 polypeptides is administrated alone is about 32.8%, and the cell killing rate when the peripheral blood monocyte cells expressing Her2 TCR-6A5-mC TCR is administrated alone is about 30.9%. Compared with the cell killing rate of a single administration, the cell killing rate of combined administration of the above two is improved, and the cell killing rate is about 95.8%, showing a significant synergistic effect. In case that the target cells in the experiment are SKOV3 cells, the cell killing rate when the replication-deficient adenovirus expressing HLA-A2 and Her2 E75 polypeptides is administrated alone is about 29.7%, and the cell killing rate when the peripheral blood monocyte cells expressing Her2 TCR-6A5-mC TCR is administrated alone is about 34.3%. Compared with the cell killing rate of a single administration, the cell killing rate of combined administration of the above two is improved, and the cell killing rate is about 66%, which also shows a significant synergistic effect.

These results show that Her2 TCR-6A5-mC T cells can specifically kill tumor cells infected with Adeasy-A2-Her2 E75 adenovirus, regardless of whether the tumor cells express endogenous HLA-A2 and Her2/neu antigens. If the adenovirus expressing HLA class I molecules and tumor antigen epitope polypeptide minigene is an oncolytic adenovirus, not only the tumor cells infected with the oncolytic virus can be selectively killed by the oncolytic virus, but also can be recognized and killed by T cells transfected with TCR that can recognize specific tumor epitopes by expressing specific exogenous tumor epitope polypeptides when the tumor cells cannot be effectively lysed by the oncolytic virus. This is the theoretical and experimental basis for the combined administration of the Adeasy-A2-Her2 E75 adenovirus and Her2 TCR-6A5-mC T cells to enhance the tumor-killing ability of the present invention.

Example 7: Infecting Tumor Cells with Oncolytic Adenovirus Expressing Her2/Neu Epitope Polypeptide Minigene can Significantly Enhance the Recognition and Killing Sensitivity of Her2 TCR-6A5-mC T Cells to Tumor Cells To further verify whether the oncolytic adenovirus Ad-E75, which expresses the Her2/neu epitope polypeptide minigene alone, increases the number of HLA-A2/Her2 epitope polypeptide complexes that can be recognized by Her2 TCR-6A5-mC T cells after infecting the tumor cells, thereby enhancing the recognition and killing sensitivity of T cells to the tumor cells, firstly, according to the method described in Preparation Example 3, an oncolytic adenovirus (OAd-E75, also known as "Ad-E75") expressing the Her2/neu epitope polypeptide mini-gene (with KDEL at the C terminal) was prepared. The Her2/neu epitope polypeptide minigene driven by the CMV promoter and the adenovirus E1A gene driven by the EF-1α promoter were simultaneously inserted into the E1 region of the replication-defective adenovirus. The sustained expression of E1A protein can make E1B-deficient adenovirus selectively replicate and proliferate in some tumor cells to produce oncolysis. The tumor cell strains MCF-7, SKOV3 and NCI-H446 were respectively infected with Ad-E75 oncolytic adenovirus, and then co-cultured with PBMCs transfected with Her2 TCR-6A5-mC TCR for 24 hours to detect the function of Her2 TCR-6A5-mC T cells in specifically secreting IFN-γ and killing target cells.

Figure 6:
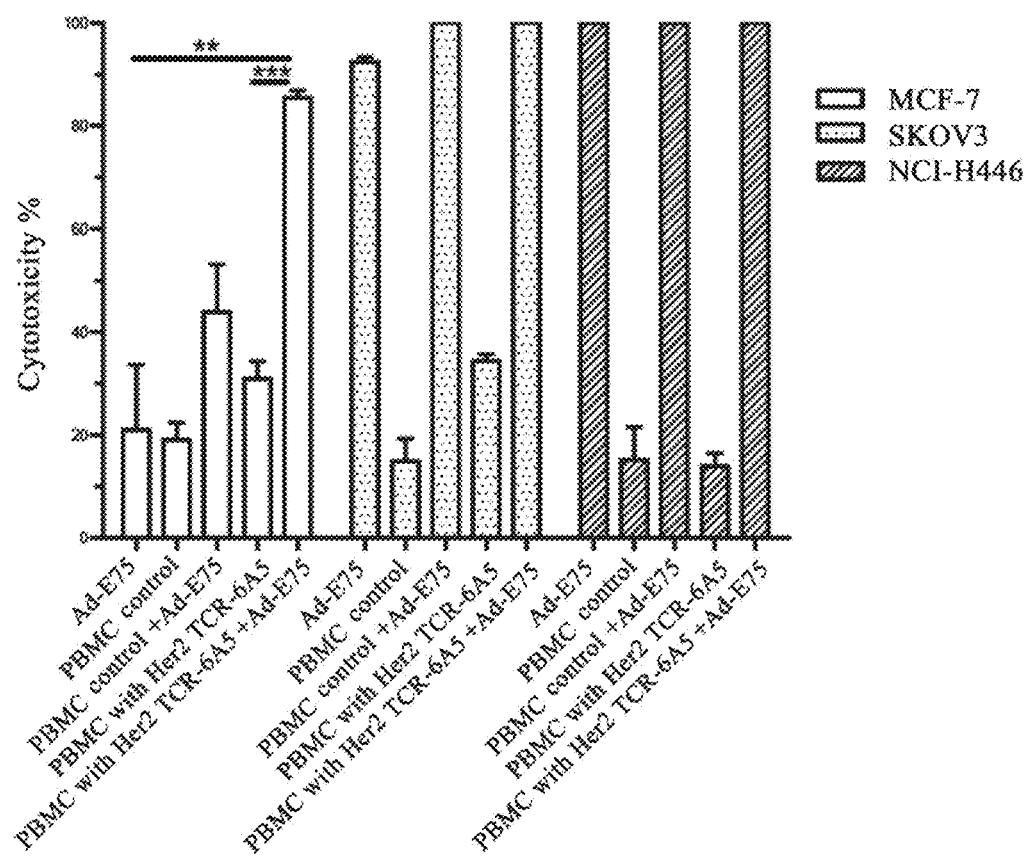
FIG. 6 shows that the oncolytic adenovirus carrying the Her2-E75 minigene can increase the recognition sensitivity of Her2 TCR-6A5-mC TCR to the target cells expressing HLA-A2 after infecting tumor cells.

FIG. 6A shows that HLA-A2-positive tumor cells MCF-7 infected with Ad-E75 oncolytic adenovirus can significantly stimulate Her2 TCR-6A5-mC T cells to specifically secrete IFN-γ, while HLA-A2-negative cells SKOV3 and NCI-H446 infected with Ad-E75 virus cannot increase the sensitivity of Her2 TCR-6A5-mC T cell specific recognition. The MOI of the adenovirus that infects the tumor cells is 10, and the E:T ratio thereof with co-cultured PBMCs transfected with Her2 TCR-6A5-mC TCR is 5:1. The tumor cell strains are HLA-A2$^+$ Her2/neu$^+$ MCF-7 cells, HLA-A2$^-$ Her2/neu$^+$ SKOV3 cells and HLA-A2$^-$ Her2/neu$^-$ NCI-H446 cells. The results showed that after the tumor cells were infected with Ad-E75 adenovirus alone, they hardly secreted interferon γ (the experimental group "Ad-E75"). The PBMCs transfected with Her2 TCR-6A5-mC TCR cannot effectively recognize MCF-7 and secrete IFN-γ ("PBMC with Her2TCR-6A5") at low E:T ratio, either. However, when HLA-A2 positive tumor cells were infected with the Ad-E75 oncolytic adenovirus, the recognition function of Her2 TCR-6A5-mC T cells to the HLA-A2 positive tumor cells can be significantly enhanced (experimental group "PBMC with Her2TCR-6A5+Ad-E75"). The Her2 TCR-6A5-mC T cells recognized tumor cells infected by the Ad-E75 oncolytic adenovirus with significantly higher recognition activity than the target cells without virus infection (p<=0.01). The Ad-E75 oncolytic adenovirus infection of tumor cells cannot increase the recognition activity of control PBMCs that have not been transfected with Her2 TCR-6A5-mC TCR (experimental group "PBMC control" and experimental group "PBMC control+Ad-E75"). This indicates that the increased secretion of IFN-γ after adenovirus infection is produced by enhancing the recognition activity of Her2 TCR-6A5-mC TCR on tumor cells. The results indicate that after the Ad-E75 oncolytic adenovirus infects the tumor cells, it can increase the number of HLA-A2/Her2/neu 369-377 polypeptide complexes, which are recognized by Her2 TCR-6A5-mC T cells on the surface of HLA-A2 positive tumor cells, by expressing the Her2/neu epitope polypeptide mini-gene, thereby enhancing the recognition sensitivity of Her2 TCR-6A5-mC T cells. The infection of HLA-A2 negative cells SKOV3 and NCI-H446 with the Ad-E75 oncolytic adenovirus did not enhance the recognition sensitivity of the cells to Her2 TCR-6A5-mC T cells, indicating that the Her2/neu epitope polypeptide requires the presentation of the endogenous HLA-A2 molecule, which further indicates that the recognition of Her2/neu epitope by Her2 TCR-6A5-mC T cells is a specific recognition restricted by HLA-A2.

In order to further verify whether the oncolytic adenovirus Ad-E75 can increase the killing ability of Her2 TCR-6A5-mC T cells to target cells after the oncolytic adenovirus Ad-E75 infects the tumor cells, the tumor cell strains SKOV3, MCF-7 and NCI-H446 were infected with Ad-E75 oncolytic adenovirus respectively. After 24 hours, they were mixed with PBMCs transfected with Her2 TCR-6A5-mC TCR and co-cultured for additional 24 hours. The number of surviving adherent cells was detected by trypan blue to determine killing ability of T cells on target cells. The MOI of the virus that infects the tumor cells is 10, and the E:T ratio of mixed culture is 5:1.

FIG. 6B shows that after Ad-E75 oncolytic adenovirus infects the tumor cells alone, it can cause the cell death of most SKOV3 and NCI-H446 cells (the experimental groups "Ad-E75" of SKOV3, U87MG and NCI-H446). It shows that Ad-E75 has obvious oncolytic effect on these tumor cells. In case that the target cells in the experiment are MCF-7 cells, the cell killing rate when the Ad-E75 oncolytic adenovirus is administrated alone is about 20.9%, and the cell killing rate when the peripheral blood monocyte cells expressing Her2 TCR-6A5-mC TCR is administrated alone is about 30.9%. Compared with the cell killing rate of a single administration, the cell killing rate of combined administration of the above two is improved, and the cell killing rate is about 85.4%, showing a significant synergistic effect. Since other target cells SKOV3 and NCI-H446 are too sensitive to Ad-E75 oncolytic adenovirus, the shown killing ability is temporarily indistinguishable from oncolytic adenovirus infection alone under this MOI condition when Her2 TCR-6A5-mC T cells were mixed with these target cells infected with Ad-E75, indicating that the killing activity is mainly caused by the oncolytic effect of oncolytic virus.

These results indicate that Her2 TCR-6A5-mC T cells can specifically recognize the Her2/neu epitope expressed by the oncolytic adenovirus and presented by endogenous HLA-A2, thereby killing the tumor cells infected with Ad-E75 oncolytic adenovirus. And these results show that the oncolytic adenovirus carrying the Her2/neu epitope polypeptide minigene can express Her2/neu epitope polypeptide which can be presented by endogenous HLA-A2 molecules after infecting the tumor cells, thereby enhancing the recognition and killing sensitivity of T cells to tumor cells. It also shows that the killing ability of Her2 TCR-6A5-mC T cells on the target cells and the oncolytic effect of oncolytic viruses have a certain synergistic effect.

Example 8: Infecting Tumor Cells with an Oncolytic Adenovirus that Simultaneously Expresses Her2/Neu Epitope Polypeptide Minigene and Exogenous HLA-A2, not Only can Significantly Enhance the Recognition and Killing Sensitivity to Tumor Cells of Her2 TCR-6A5-mC T Cells, but Also can Make the HLA-A2 Negative Tumor Cell Strains to be Identified In order to further verify after the oncolytic adenoviral vector Ad-E75A2, which simultaneously expresses Her2/neu epitope polypeptide minigene and HLA-A2, infects tumor cells, whether it increases the number of HLA-A2/Her2 epitope polypeptide complexes which can be recognized by Her2 TCR-6A5-mC T cells on the surface of cells thereby enhancing the recognition and killing sensitivity of T cells to the tumor cells, firstly, according to the method described in Preparation Example 3, an oncolytic adenovirus (OAd-E75A2, also known as "Ad-E75A2") expressing both the Her2/neu epitope polypeptide minigene (with KDEL at the C terminal) and HLA-A2 was prepared. It has been shown in Example 6 that the target cells infected with replication-deficient adenovirus (Adeasy-A2E75), in which HLA-A2 gene linked by Furin-F2A linker fragment is inserted upstream of the Her2/neu epitope polypeptide minigene, can express HLA-A2 and Her2/neu epitopes, and significantly enhance the recognition activity of Her2 TCR-6A5-mC T cells to target cells. The oncolytic adenovirus constructed in this example is derived from the oncolytic adenovirus described in Example 7, except that the HLA-A2 gene linked by the F2A linker fragment is inserted downstream of the Her2/neu epitope polypeptide minigene, so as to construct oncolytic adenovirus Ad-E75A2. The tumor cell strains HLA-A2-positive Her2-negative U87MG, HLA-A2-negative Her2-positive NCI-H460 and HT-29 cells were infected with Adeasy-A2E75 replication-defective adenovirus and Ad-E75A2 oncolytic adenovirus, respectively. After 24 hours, they were mixed with PBMCs transfected with Her2 TCR-6A5-mC TCR and co-cultured for additional 24 hours to detect the function of Her2 TCR-6A5-mC T cells in specifically secreting IFN-γ and killing target cells.

Figure 7:
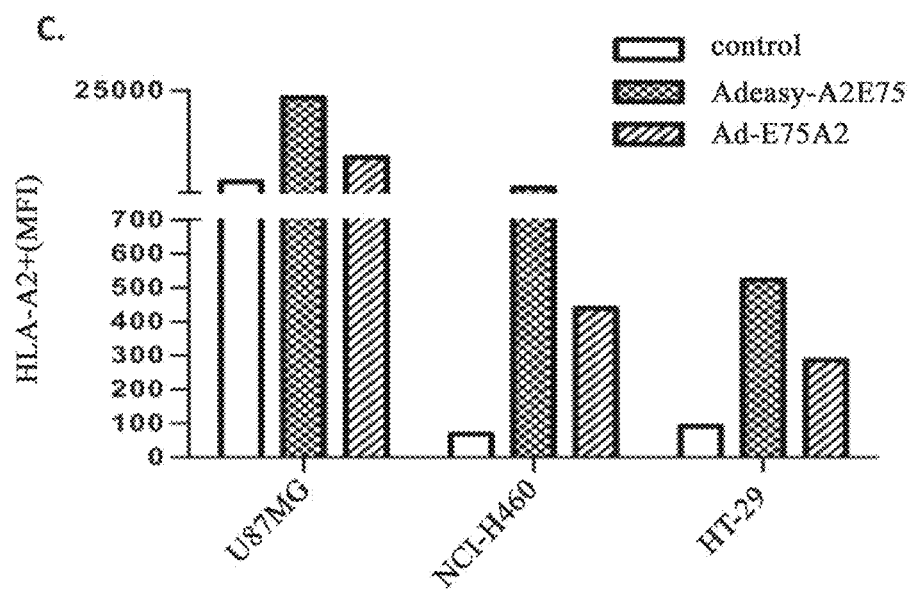
FIG. 7 shows that replication-defective adenoviruses carrying HLA-A2 gene and Her2-E75 minigene can increase the recognition sensitivity of Her2 TCR-6A5-mC TCR to different target cells after infecting tumor cells.

Firstly, whether the adenovirus carrying the HLA-A2 gene expresses foreign HLA-A2 after infecting the tumor cell strains was detected. U87MG, NCI-H460 and HT-29 cells were infected with Adeasy-A2E75 and Ad-E75A2 adenovirus, respectively. Cells not infected with adenovirus were used as control. Cells were collected 24 hours after virus infection and stained with HLA-A2 antibody and analyzed by flow cytometry. FIG. 7C shows that U87MG expresses endogenous HLA-A2, while NCI-H460 and HT-29 do not express HLA-A2. Both replication-defective adenovirus Adeasy-A2E75 and oncolytic adenovirus Ad-E75A2 can increase the expression level of HLA-A2 on the cell surface.

FIG. 7A shows that tumor cells U87MG, NCI-H460 and HT-29 infected with replication-defective adenovirus Adeasy-A2E75 can significantly stimulate Her2 TCR-6A5-mC T cells to specifically secrete IFN-γ, regardless of whether the target cells express endogenous HLA-A2 or Her2 antigen. This is consistent with the recognition activity against other target cells shown in FIG. 5A in Example 6. The MOI of the adenovirus that infects the tumor cells is 10, and the E:T ratio thereof with co-cultured PBMCs transfected with Her2 TCR-6A5-mC TCR is 10:1. The tumor cells are HLA-A2$^+$ Her2/neu$^-$ U87MG cells, HLA-A2$^-$ Her2/neu$^+$NCI-H460 and HT-29 cells. The results showed that after the tumor cells were infected with Adeasy-A2E75 replication-defective adenovirus alone, they hardly secreted IFN-γ (the experimental group "Adeasy-A2E75"). PBMCs transfected with Her2 TCR-6A5-mC TCR could not effectively recognize target cells and secrete IFN-γ (experimental group "PBMC with Her2TCR-6A5"). However, when the tumor cells are infected with Adeasy-A2E75 adenovirus, the recognition function of Her2 TCR-6A5-mC T cells can be significantly enhanced (experimental group "PBMC with Her2TCR-6A5+Adeasy-A2E75"). The activity of Her2 TCR-6A5-mC T cells in recognizing tumor cells infected with Adeasy-A2E75 adenovirus was significantly higher than that of target cells without virus infection (p<=0.01), and it was also significantly higher than the experimental group infected with replication-defective viruses alone.

Figure 8:
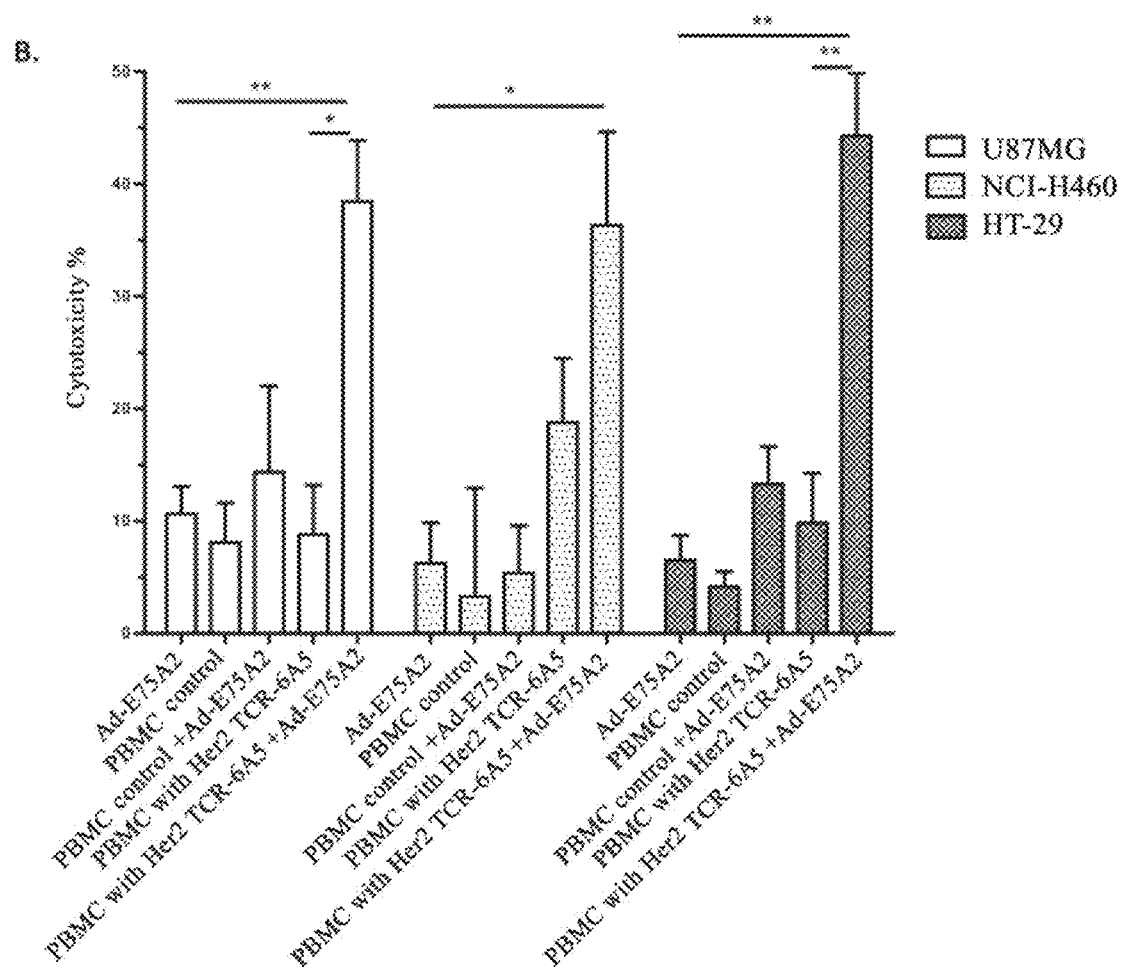
FIG. 8 shows that the oncolytic adenoviruses carrying Her2-E75 minigene and HLA-A2 gene all can increase recognition sensitivity of Her2 TCR-6A5-mC TCR to different target cells after infecting tumor cells.

FIG. 8A shows that after tumor cells U87MG, NCI-H460 and HT-29 cells were infected with oncolytic adenovirus Ad-E75A2, although Her2 TCR-6A5-mC T cells did not significantly increase the secretion of IFN-γ after recognizing NCI-H460, the recognition activities thereof against U87MG and HT-29 were increased significantly compared with infection with replication-defective Adeasy-A2E75 virus (U87MG experimental group "PBMC with Her2 TCR-6A5+Ad-E75A2", p<=0.001; HT-29 experimental group "PBMC with Her2 TCR-6A5+Ad-E75A2", p<=0.0001). It indicates that the oncolytic adenovirus carrying HLA-A2 gene and Her2/neu epitope polypeptide minigene can express exogenous HLA-A2 and Her2/neu epitopes after infecting tumor cells, such that Her2 TCR-6A5-mC T cells could identify HLA-A2 negative or Her2 negative target cells.

In order to further verify after the oncolytic adenovirus vector Ad-E75A2 infects tumor cells, whether it increases the killing ability of Her2 TCR-6A5-mC T cells to target cells, the tumor cell strains U87MG, NCI-H460 and HT-29 cells were infected with replication defective adenovirus Adeasy-A2E75 and oncolytic adenovirus Ad-E75A2, respectively. After 24 hours, they were mixed with PBMCs transfected with Her2 TCR-6A5-mC TCR and co-cultured for additional 24 hours. The number of surviving adherent cells was detected by Trypan blue to determine killing ability of T cells on target cells. The MOI of the virus that infects the tumor cells is 10, and the E:T ratio of mixed culture is 10:1.

FIG. 7B and FIG. 8B show that after infection alone under the used MOI conditions, both the replication-defective adenovirus Adeasy-A2E75 and the oncolytic adenovirus Ad-E75A2 showed a certain oncolytic effect (each experimental group "Adeasy-A2E75" in FIG. 7B and each experimental group "Ad-E75A2" in FIG. 8B). After infection with adenovirus, it can significantly enhance the killing ability of Her2 TCR-6A5-mC T cells to target cells.

Infection with replication-defective adenovirus Adeasy-A2E75 can enhance the killing ability of Her2 TCR-6A5-mC T cells on all target cells, and the killing ability of Her2 TCR-6A5-mC T cell to the target cells infected with replication-defective adenovirus Adeasy-A2E75 is significantly enhanced regardless of comparing with the experimental group infected with adenovirus alone (in FIG. 7B, each experimental group "Adeasy-A2E75"; experimental group U87MG p<=0.01, experimental group NCI-H460 p<=0.05, experimental group HT-29 p<=0.001), or compared with the experimental group using Her2 TCR-6A5-mC T cells alone (in FIG. 7B, each experimental group "PBMC with Her2 TCR-6A5"; experimental group U87MG p<=0.001, experimental group NCI-H460 p<=0.05, experimental group HT-29 p<=0.001). Infection with oncolytic adenovirus Ad-E75A2 can also enhance the killing ability of Her2 TCR-6A5-mC T cells to target cells. Furthermore, in case that the target cells in the experiment shown in FIG. 7B are U87MG cells, the cell killing rate when the replication-deficient adenovirus is administrated alone is about 9.8%, and the cell killing rate when the peripheral blood monocyte cells expressing Her2 TCR-6A5-mC TCR is administrated alone is about 8.8%. Compared with the cell killing rate of a single administration, the cell killing rate of combined administration of the above two is improved, and the cell killing rate is about 83.6%, which shows a significant synergistic effect. In case that the target cells in the experiment shown in FIG. 7B are NCI-H460 cells, the cell killing rate when the replication-deficient adenovirus is administrated alone is about 5.4%, and the cell killing rate when the peripheral blood monocyte cells expressing Her2 TCR-6A5-mC TCR is administrated alone is about 7%. Compared with the cell killing rate of a single administration, the cell killing rate of combined administration of the above two is improved, and the cell killing rate is about 33.4%, which also shows a significant synergistic effect. In case that the target cells in the experiment shown in FIG. 7B are HT-29 cells, the cell killing rate when the replication-deficient adenovirus is administrated alone is about 8.4%, and the cell killing rate when the peripheral blood monocyte cells expressing Her2 TCR-6A5-mC TCR is administrated alone is about 12.9%. Compared with the cell killing rate of a single administration, the cell killing rate of combined administration of the above two is improved, and the cell killing rate is about 74.2%, which also shows a significant synergistic effect.

Compared with the experimental group infected with oncolytic adenovirus alone (in FIG. 8B, each experimental group "Ad-E75A2"; experimental group U87MG p<=0.01, experimental group NCI-H460 p<=0.05, experimental group HT-29 p<=0.01), Her2 TCR-6A5-mC T cells show significant killing activity on all target cells infected with the oncolytic adenovirus. Compared with the experimental group using Her2 TCR-6A5-mC T cells alone (in FIG. 8B, each experimental group "PBMC with Her2 TCR-6A5";

experimental group U87MG p<=0.05, experimental group HT-29 p<=0.01), Her2 TCR-6A5-mC T cells showed significant killing activity on U87MG and HT-29 cells infected with the oncolytic adenovirus. Furthermore, in case of the target cells in the experiment shown in FIG. 8B are U87MG cells, the cell killing rate when the oncolytic adenovirus is administrated alone is about 10.6%, and the cell killing rate when the peripheral blood monocyte cells expressing Her2 TCR-6A5-mC TCR is administrated alone is about 10.6%. Compared with the cell killing rate of a single administration, the cell killing rate of combined administration of the above two is improved, and the cell killing rate is about 38.4%, showing a significant synergistic effect. In case of the target cells in the experiment shown in FIG. 8B are HT-29 cells, the cell killing rate when the oncolytic adenovirus is administrated alone is about 6.5%, and the cell killing rate when the peripheral blood monocyte cells expressing Her2 TCR-6A5-mC TCR is administrated alone is about 9.8%. Compared with the cell killing rate of a single administration, the cell killing rate of combined administration of the above two is improved, and the cell killing rate is about 44.2%, which also shows a significant synergistic effect.

It can be seen that the oncolytic adenovirus vector expressing both Her2/neu epitope polypeptide minigene and HLA-A2 can significantly enhance the killing sensitivity of Her2 TCR-6A5-mC T cells after infecting the tumor target cells, regardless of whether the target cells express endogenous HLA-A2 and Her2 antigens. The combined administration of the oncolytic adenovirus and the TCR-T cell showed a synergistic effect in killing tumor cells.

Figure 11:
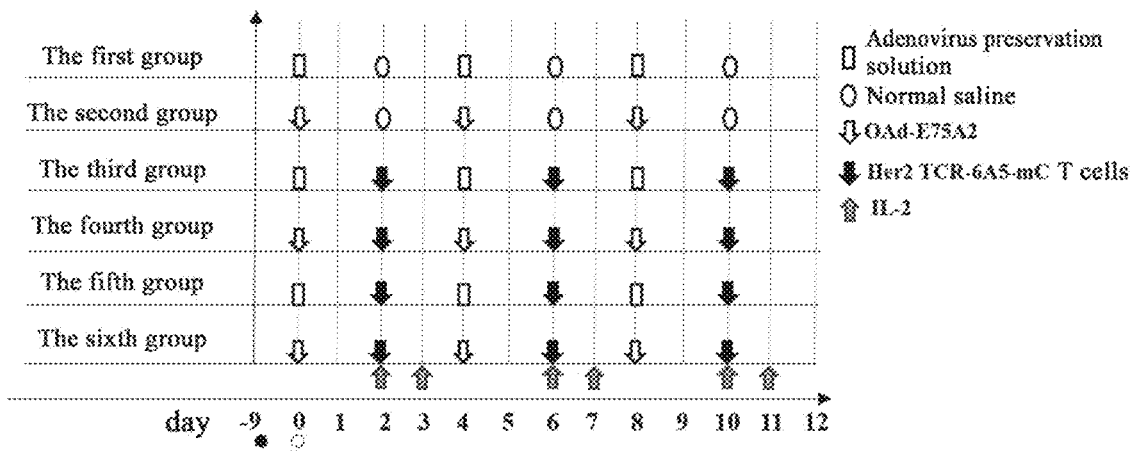
FIG. 11 shows the animal experiment protocol in Example 9, which specifically shows the dosing regimen of this example, wherein the first group is a blank control group; the second group is an OAd-E75A2 group (that is, the oncolytic virus is administered alone); the third group is an Her2 TCR-6A5-mC T(IV) group (i.e., TCR T is administered intravenously alone); the fourth group is an OAd-E75A2$^+$ Her2 TCR-6A5-mC T(IV) group (i.e., the combined administration, in which TCR T is administered intravenously); the fifth group is a Her2 TCR-6A5-mC T(IT) group (that is, TCR T is administered intratumorally alone); the sixth group is an OAd-E75A2$^+$ Her2 TCR-6A5-mC T (IT) group (i.e., the combined administration, in which TCR T is administered intratumorally).
Figure 12:
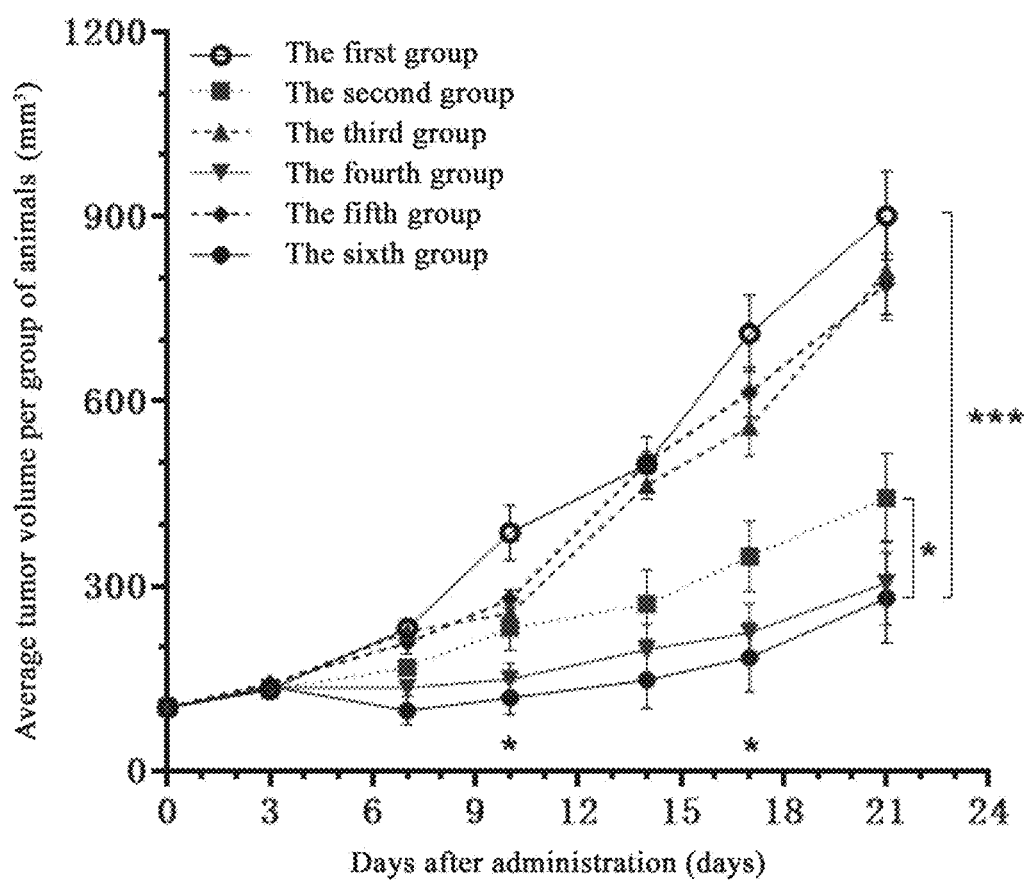
FIG. 12 shows an average tumor volume change profile of each group of animals in Example 9, wherein "*" indicates $p \leq 0.05$, and "***" indicates $p \leq 0.001$.
Figure 13:
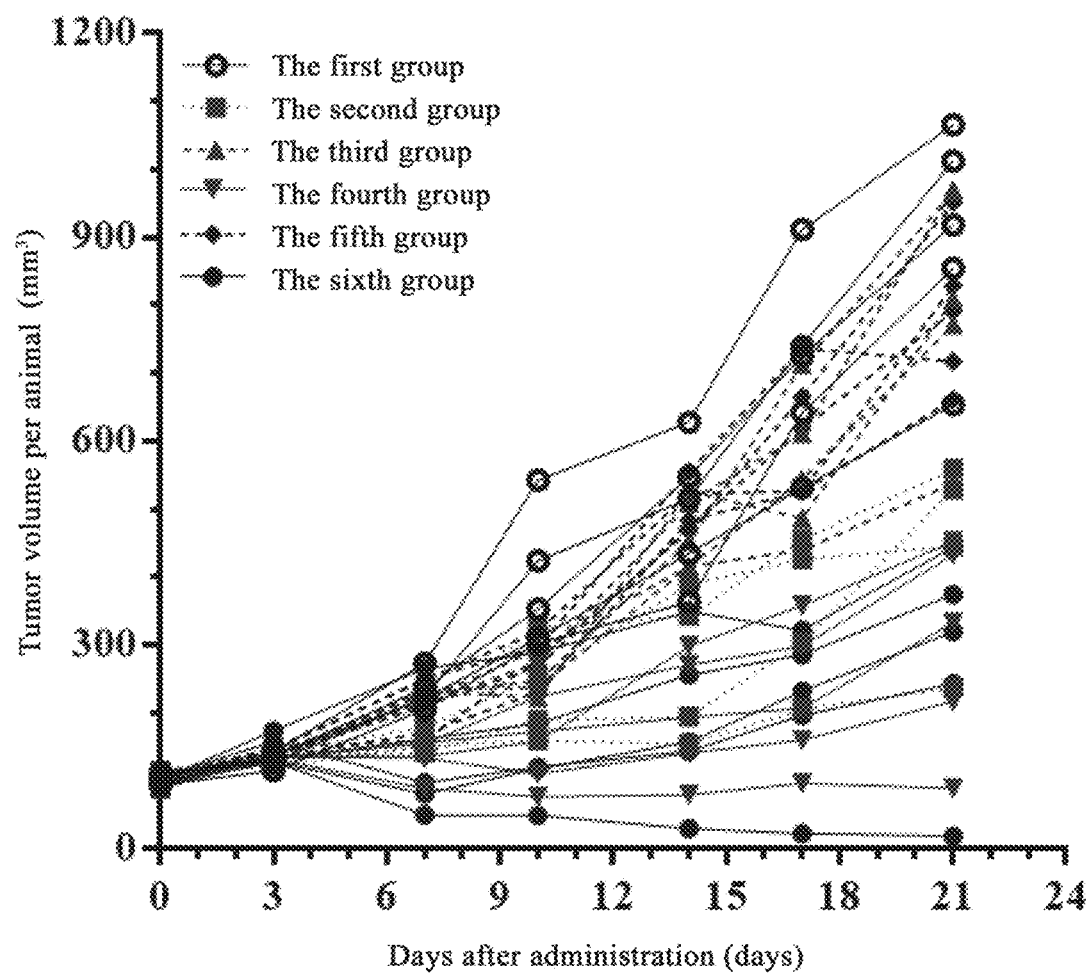
FIG. 13 shows a tumor volume change profile of a single animal in each group of animals in Example 9.
Figure 14:
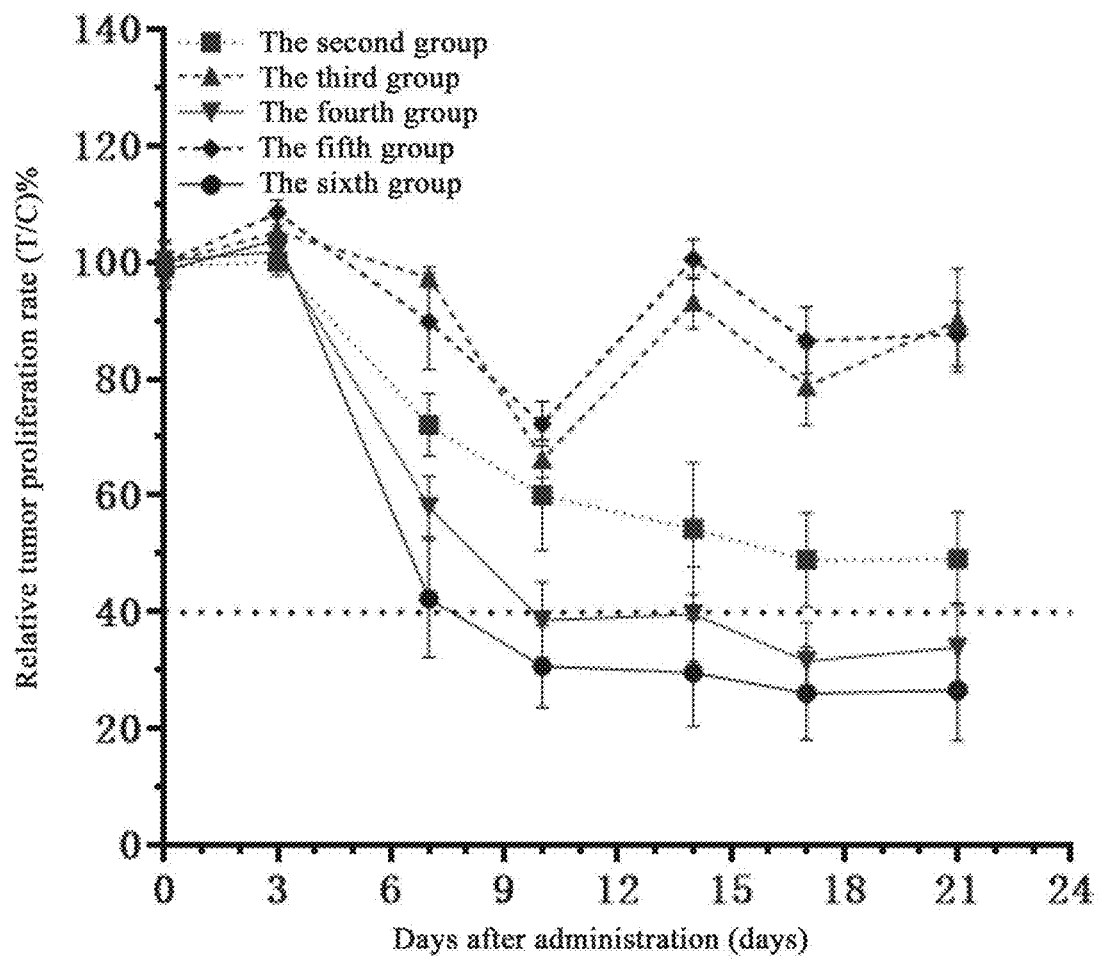
FIG. 14 shows the relative tumor proliferation rate (T/C) % of each group of animals in Example 9 as a function of the number of days after administration. The relative tumor proliferation rate (T/C) % refers to the percentage value of the average subcutaneous tumor volume of all treatment groups in the experiment compared to the average subcutaneous tumor volume of the control group measured on the same day, which is used to indicate the inhibition of tumor growth in the treatment group relative to the control group. Generally, in the drug development process, it is considered to be the basic standard for drug effectiveness that T/C % is less than 40%.
Figure 15:
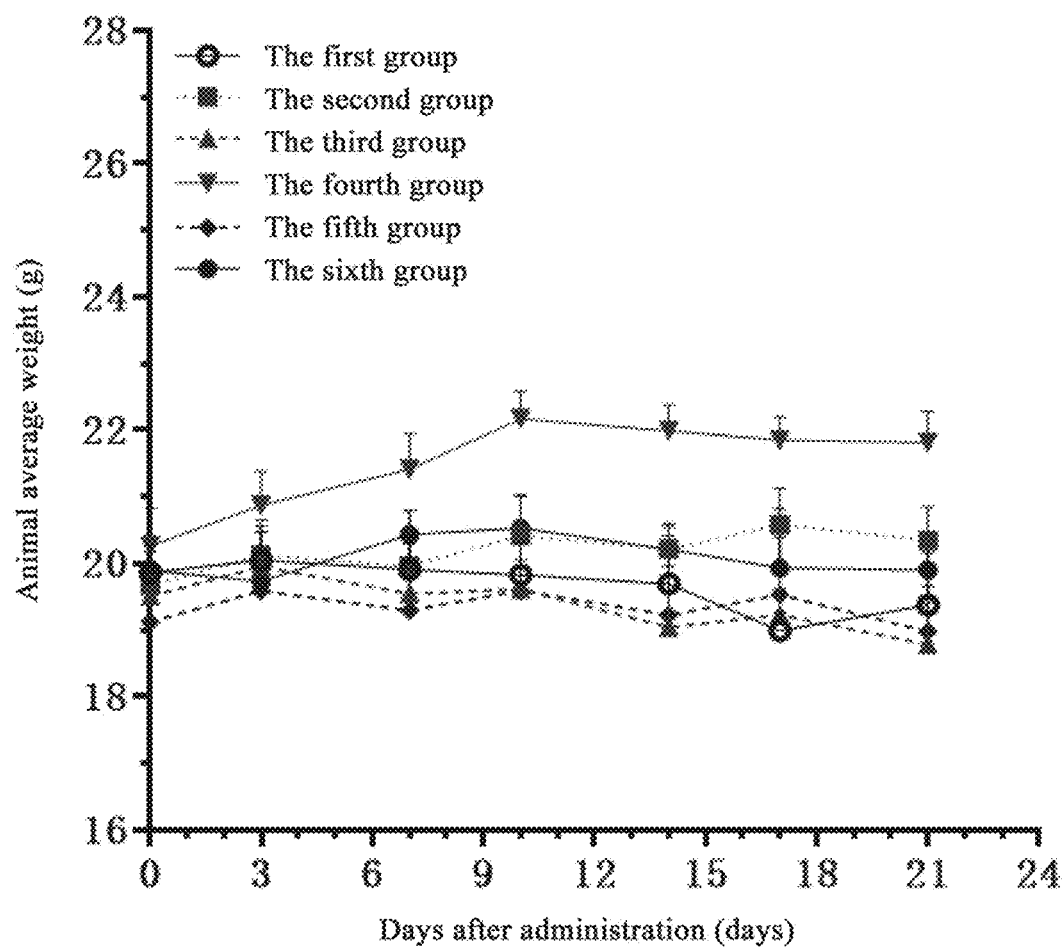
FIG. 15 shows an average body weight change profile of each group of animals in Example 9.
Figure 16:
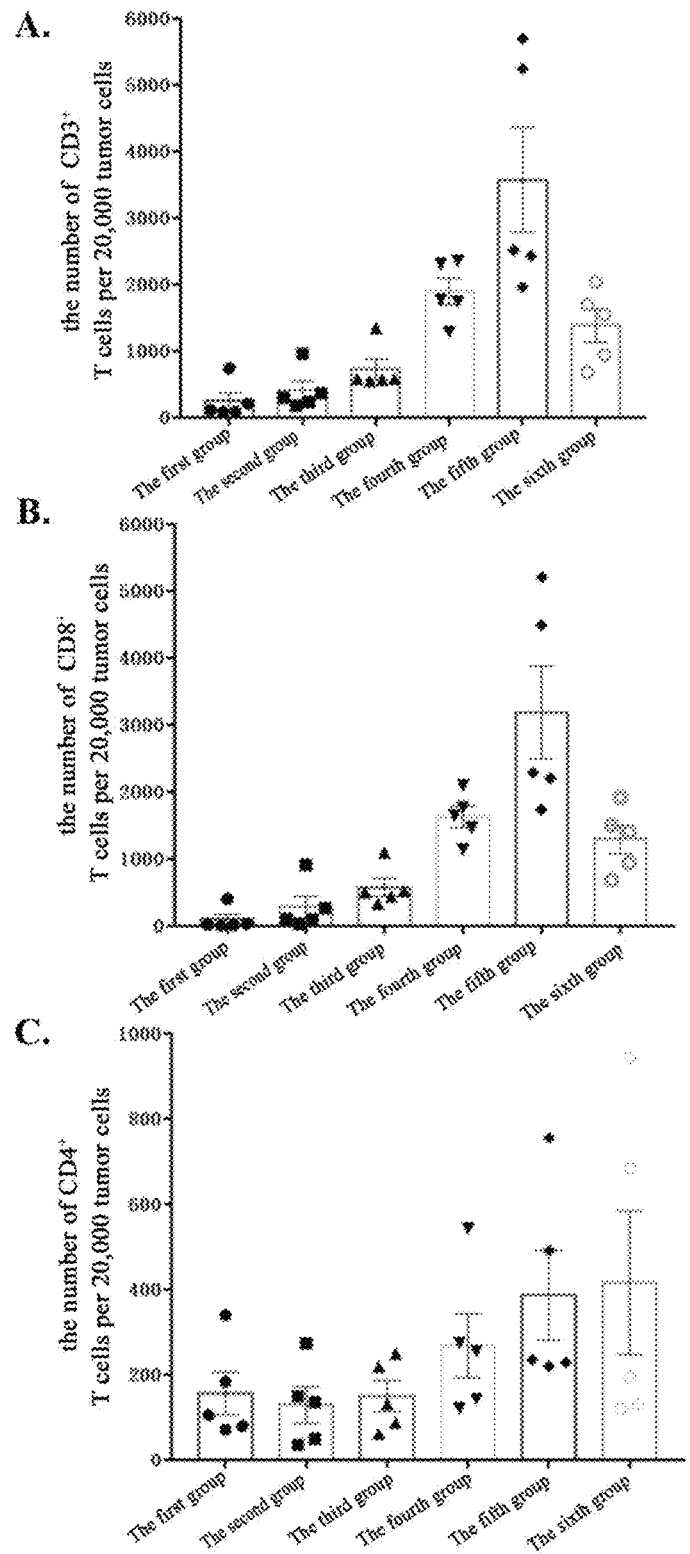
FIG. 16 shows the results of flow cytometry analysis of the number of human T cells in tumor tissues of each group of animals in Example 9 at the end of the experiment. FIG.

Example 9: The Combined Inhibitory Effect of Oncolytic Adenovirus OAd-E75A2 and Human Her2 TCR-6A5-mC T Cells on the Growth of Human Ovarian Cancer Cells SKOV3 Subcutaneously Inoculated in NCG Severe Immunodeficiency Mice In this experiment, human ovarian cancer cells SKOV3 were inoculated into NCG severe immunodeficiency mice (provided by Jiangsu Jicui Company) subcutaneously on the dorsal side of the right forelimb to prepare a tumor-bearing animal model that mimics the human environment and detect combined inhibitory effect of the oncolytic adenovirus OAd-E75A2 prepared according to Preparation Example 3 and human Her2 TCR-6A5-mC T cells obtained according to the method described in the aforementioned "Recombinant TCR lentivirus transfection of human T cells" (the used peripheral blood monocyte cells were obtained from the United States allcells company (Cat. No. PB005F, specification 100 million, frozen)) on the growth of human ovarian cancer cells SKOV3 subcutaneously inoculated in NCG severe immunodeficiency mice. The amount of cell inoculation for each animal is $3\times10^6$ cells. About 9 days after cell inoculation, 30 tumor-bearing mice with subcutaneous tumor volume meeting the requirements (tumor volume 90-120 mm$^3$) were selected and divided into 6 groups according to the randomized block grouping. Each group has 5 mice, and the day of grouping is set to day 0. The first group is a blank control group. Each mouse in the group was injected intratumorally (abbreviated as I.T.) with 100 μl of adenovirus preservation solution (containing 10 mM Tris (pH7.4) 1 mM MgCl$_2$, 10% glycerol, filtered and sterilized and stored at 4° C.) on the Day 0, Day 4 and Day 8, respectively, and for each mouse, 100 μl of normal saline was injected intravenously (abbreviated as I.V.) via tail on the Day 2, Day 6 and Day 10. The second group is OAd-E75A2 group (i.e., administration of oncolytic virus alone), each mouse in the group was injected intratumorally with 100 μl of oncolytic adenovirus OAd-E75A2 on the Day 0, Day 4 and Day 8, the virus injection amount for each animal was $5\times10^8$ PFU, and for each mouse, 100 μl of normal saline was injected intravenously via tail on the Day 2, Day 6 and Day 10. The third group was the Her2 TCR-6A5-mC T(IV) group (i.e., intravenous administration of TCR T alone), each mouse in the group was injected intratumorally with 100 μl of adenovirus preservation solution on the Day 0, Day 4 and Day 8, and for each mouse, 100 μl of Her2 TCR-6A5-mC T cells was injected intravenously via tail on the Day 2, Day 6 and Day 10, the number of cells was $2\times10^7$. The fourth group was OAd-E75A2+Her2 TCR-6A5-mC T(I.V.) group (i.e., combined administration, in which TCR T was administrated intravenously), each mouse in the group was injected intratumorally with 100 μl of oncolytic adenovirus OAd-E75A2 on the Day 0, Day 4 and Day 8, respectively, and the virus injection amount for each animal was $5\times10^8$ PFU, and for each mouse, 100 μl of Her2 TCR-6A5-mC T cells was injected intravenously via tail on the Day 2, Day 6 and Day 10, the number of cells was $2\times10^7$. The fifth group was Her2 TCR-6A5-mC T(IT) group (i.e., intratumoral administration of TCR T alone), each mouse in the group was injected intratumorally with 100 μl of adenovirus preservation solution on the Day 0, Day 4 and Day 8, respectively, and for each mouse, 100 μl of Her2 TCR-6A5-mC T cells was injected intratumorally on the Day 2, Day 6 and Day 10, the number of cells was $2\times10^7$. The sixth group was the OAd-E75A2+Her2 TCR-6A5-mC T(IT) group (i.e., the combined administration, in which TCR T was intratumorally administrated), each mouse in the group was injected intratumorally with 100 μl of oncolytic adenovirus OAd-E75A2 on the Day 0, Day 4 and Day 8, respectively, and the virus injection amount for each animal was $5\times10^8$ PFU, and for each mouse, 100 μl of Her2 TCR-6A5-mC T cells was injected intratumorally on the Day 2, Day 6 and Day 10. In the third to sixth groups, when 100 μl of Her2 TCR-6A5-mC T cells were administered to each mouse, all the cells were freshly prepared in accordance with the preparation method in the aforementioned "Recombinant TCR Lentivirus Transfection of Human T Cells" section described above, in which the cultivation time was calculated from the time when the Her2 TCR-6A5-mC recombinant lentivirus transfected PBMCs, and based on the expected different administration time, the cultivation was performed for about 8 days in advance. The positive rate of the Her2 TCR-6A5-mC TCR is about 35-38%. In addition, each group of animals was injected subcutaneously (abbreviated as S.C.) via the neck with 100,000 IU IL2 (purchased from Beijing Si Huan Pharmaceutical Factory, the product batch number is 81766010002383594693) on the Day 2, Day 3, Day 6, Day 7, Day 10 and Day 11, which was used to stimulate the proliferation and activation of T cells, so that human T cells can survive longer in NCG mice. The animal experiment protocol is shown in FIG. 11. From the day of grouping (Day 0), the subcutaneous tumor volume of each mouse was measured and the mouse weight was weighed. The measurement and recording were performed twice a week. In the experimental results, the average tumor volume change of each group of animals is shown in FIG. 12. The tumor volume change of a single animal in each group is shown in FIG. 13, and the relative tumor proliferation rate (T/C %) between animal groups is shown in FIG. 14. The average weight change of each group of animals is shown in FIG. 15, and the flow cytometric analysis results of the number of human T cells in the tumors of each group of animals at the end of the experiment are shown in FIG. 16.

The above results show that when human Her2 TCR-6A5-mC T cells are administered alone (the third and fifth groups), there is no obvious inhibitory effect on the growth of human ovarian cancer cells SKOV3 subcutaneously inoculated in NCG severe immunodeficiency mice (see FIGS. 12-14). This is because the human ovarian cancer cells SKOV3 used in this experiment are HLA-A2 negative and Her2/neu positive. However, it can be seen from the above results that in the fourth group (OAd-E75A2+Her2 TCR-6A5-mC T(IV) group) and the sixth group (OAd-E75A2+Her2 TCR-6A5-mC T (IT) group) according to the combined administration of the present invention, the growth of subcutaneous tumor of animals was well inhibited (see FIG. 12), there is a highly significant difference when compared with the average volume of subcutaneous tumor of animals in the blank control group (P<=0.001), and there is also a significant difference when compared with the average volume of subcutaneous tumors of animals in the second group (OAd-E75A2 group), (P<=0.05). It can be seen from FIG. 13 that the volume change curve of the subcutaneous tumor growth of each group of animals is relatively concentrated, and no significant abnormal values appear. It can be seen from FIG. 14 that the relative proliferation rate (T/C %) of subcutaneous tumors of the animals in the fourth group (OAd-E75A2+Her2 TCR-6A5-mC T(IV) group) and the sixth group (OAd-E75A2+Her2 TCR-6A5-mC T(IT) group) reached 40% (or below) inhibition rate on the Day 10, reaching an effective standard of clinical drugs; it can be seen from FIG. 15 that, except for the fourth group (OAd-E75A2+Her2 TCR-6A5-mC T(IV) group), the other animals did not exhibit a large change in the average body weight and did not show obvious toxicity, while the average weight of the fourth group of animals has increased significantly. This key indicator shows that the administration mode of intratumoral injection of the oncolytic adenovirus and tail intravenous infusion of human TCR T cells is more conducive to tumor treatment than other modes of administration, with a small impact on the overall condition of the animal's body; it can be seen from FIG. 16 that, when the experiment was terminated, in the two groups of animals that had been injected with Her2 TCR-6A5-mC T cells via tail vein, the fourth group of animals still had more alive human T cells ($CD3^+$, $CD8^+$ and $CD4^+$) in the tumor compared with the third group. This may be because the intratumoral injection of the oncolytic adenovirus OAd-E75A2 caused more human Her2 TCR-6A5-mC T homing within the tumor; therefore, the fourth group also showed a significant inhibitory effect on tumor growth. In the subcutaneous tumors of the fifth and sixth groups of animals injected with Her2 TCR-6A5-mC T intratumorally, a large number of human T cells ($CD3^+$, $CD8^+$ and $CD4^+$) were still alive when the experiment was terminated, and the number of $CD8^+$ T cells in the tumors of the sixth group (combined administration group) was significantly less than the number of $CD8^+$ T cells in the tumors of the fifth group of animals injected with Her2 TCR-6A5-mC T alone, similarly with the number of human T cells in the fourth group of animal tumors. More importantly, the growth inhibitory effect of subcutaneous tumors in the sixth group of animals was more significant than that of the fourth group. This may be because after intratumoral injection of OAd-E75A2, intratumoral infusion of human Her2 TCR-6A5-mC T can make Her2 TCR-6A5-mC T more convenient to act on the tumor cells, thus showing a better anti-tumor effect than the fourth group.

In summary, the two combined administration groups (groups 4 and 6) show a very significant anti-tumor effect, in which human Her2 TCR-6A5-mC T cells (intravenous injection and intratumoral injection) were further administered after intratumoral injection of the oncolytic adenovirus OAd-E75A2, which fully demonstrates that after the oncolytic virus OAd-E75A2 infects the tumor cells and express HLAA2 and E75 epitope peptides, the subsequent Her2 TCR-6A5-mC T can recognize the complex composed of HLAA2 and E75 on the surface of tumor cells infected with OAd-E75A2, which then activated Her2 TCR-6A5-mC T, and finally exerted the dual antitumor effect of oncolytic adenovirus and TCR T cells; and in the other two Her2 TCR-6A5-mC T single administration groups (intravenous injection and intratumor injection), the subcutaneous tumors of animals cannot effectively present the E75 epitope peptide of HER2 since they do not express HLAA2, and cannot be recognized by Her2 TCR-6A5-mC T. Thus, it cannot activate Her2 TCR-6A5-mC T, so that it fails to show obvious anti-tumor effect. Animals in the oncolytic adenovirus single administration group (the second group) show a weak antitumor effect. The above results show that the combination administration of the present invention can greatly improve the therapeutic effect on tumors.

DISCUSSION

Adoptive transfer of T cells modified by tumor-specific TCR genes is the most promising immune cell therapy (TCR-T therapy) for the treatment of malignant solid tumors. If the tumor antigen targeted by TCR-T is a tumor-associated antigen derived from self-protein, the specific TCR affinity of TCR-T may not be sufficient to recognize the trace HLA/epitope polypeptide complex presented by tumor cells and then effectively kill tumor cells. In addition, not only the tumor microenvironment can cause the immunosuppressive state in tumor tissues, but also reduce or lack the expression of HLA class I molecules in tumor cells. The class I antigen presentation mechanism in tumor cells may also be defective, thereby causing tumor antigen expression not to be effectively presented by MHC class I molecules, which also limits the function of TCR-T in recognizing and killing tumor cells. Oncolytic virus not only can selectively replicate in tumor cells and lyse the tumor cells, but also can alleviate the local immunosuppressive state of tumors through its own immunogenicity. Oncolytic viruses can also be used as gene carriers to selectively express foreign genes in tumor cells. If the oncolytic adenovirus selectively expresses HLA class I molecules and tumor epitope polypeptides in tumor cells, the number of HLA class I molecules and epitope polypeptide complexes on the surface of tumor cells can be increased, thereby enhancing the sensitivity of TCR-T to recognize and kill tumor cells. In addition, the combined administration of TCR-T and the oncolytic viruses expressing HLA class I molecules and epitope polypeptides not only shows the synergistic effect of the above two in the process of specifically killing tumor cells, but also expands the applicable scope of TCR-T. For example, when TCR-T expressing the Her2 TCR of the present invention is administrated alone, it can only be used for patients with HLA-A2-positive Her2/neu-positive tumors due to the HLA-A2 restriction. If combing with the oncolytic adenovirus of the present invention, by selectively infecting tumor cells and expressing exogenous HLA-A2 molecules and Her2/neu epitope polypeptides, the HLA-A2-negative tumors and the tumor cells with low or even no expression of Her2/neu antigens can all become target cells of TCR-T based on Her2 TCR, which can avoid the limitations of HLA restriction of the adoptive TCR-T cell therapy, thereby greatly increasing the applicable scope of TCR-T.

In conclusion, the technology and method of the present invention provide a new approach for the treatment of tumors by the combined application of adoptively transferred T cells modified by specific TCR and oncolytic viruses expressing HLA class I molecules and tumor antigen epitope polypeptides.

What is claimed is:

1. A therapeutic agent for treatment of tumors and/or cancers, comprising:
   (a) a first composition, wherein the first composition comprises a first active ingredient in a first pharmaceutically acceptable carrier, and the first active ingredient includes or contains a nucleic acid having a labeling polypeptide coding sequence for being introduced into a tumor cell and/or a cancer cell; wherein the labeling polypeptide comprises amino acid sequences of 4-8 identical epitope polypeptides of Her2/neu 369-377 as shown in SEQ ID NO:3; and
   (b) a second composition, wherein the second composition comprises a second active ingredient in a second pharmaceutically acceptable carrier, and the second active ingredient comprises T cell receptor modified immune cells; the TCR-modified immune cells can specifically recognize and bind to the epitope polypeptides presented by MHC class I molecules;
   wherein the first active ingredient is a replication-selective recombinant oncolytic virus.

2. The therapeutic agent of claim 1, wherein the labeling polypeptide comprises the following amino acid sequences that are operatively linked in a 5' to 3' tandem fashion: an amino acid sequence of a N-terminal signal peptide, the amino acid sequences of the 4-8 identical epitope polypeptides, an amino acid sequence of an optional C-terminal endoplasmic reticulum retention signal peptide; wherein, the amino acid sequences of every two adjacent epitope polypeptides of the 4-8 identical epitope polypeptides are linked by an amino acid sequence of cleavable linker polypeptide.

3. The therapeutic agent of claim 1, wherein the nucleic acid further has an HLA protein coding sequence, wherein the HLA protein coding sequence and the labeling polypeptide coding sequence are under control of their respective promoter, or the HLA protein coding sequence and the labeling polypeptide coding sequence are under control of the same promoter and the HLA protein coding sequence is operatively linked to the labeling polypeptide coding sequence through a cleavable linker polypeptide coding sequence; wherein the HLA protein includes an HLA-A2 protein that comprises an amino acid sequence of SEQ ID NO: 29.

4. The therapeutic agent of claim 1, wherein the nucleic acid includes DNA or RNA.

5. The therapeutic agent of claim 1, wherein a genome of the replication-selective recombinant oncolytic virus has the labeling polypeptide coding sequence and an optional HLA protein coding sequence.

6. The therapeutic agent of claim 5, wherein the replication-selective recombinant oncolytic virus is derived from a genetically mutated virus with oncolytic effect or a wild-type virus with oncolytic effect; wherein, the replication-selective recombinant oncolytic virus includes those derived from adenovirus, vaccinia virus, herpes simplex virus, measles virus, Semliki forest virus, vesicular stomatitis virus, polio virus, retrovirus, reovirus, Seneca valley virus, Echo-type enterovirus, Coxsackie virus, Newcastle disease virus and Malaba virus with oncolytic effect.

7. The therapeutic agent of claim 5, wherein the replication-selective recombinant oncolytic virus is a recombinant oncolytic adenovirus obtained by genetically modifying an adenovirus type 5, and E1B-55K gene and/or E1B-19K gene are deleted from the genome of the recombinant oncolytic adenovirus, and E1A gene coding sequence is comprised in the genome of the recombinant oncolytic adenovirus; wherein the E1A gene coding sequence is under control of an exogenous promoter; wherein, E3 gene of the recombinant oncolytic adenovirus is completely or partially deleted.

8. The therapeutic agent of claim 5, wherein the recombinant oncolytic virus is a recombinant oncolytic adenovirus obtained by genetically modifying an adenovirus type 5, and E1A gene of the recombinant oncolytic adenovirus is modified so that the expressed E1A protein cannot bind to pRb protein; wherein the E1A gene coding sequence is under control of an exogenous promoter; wherein E3 gene of the recombinant oncolytic adenovirus is completely or partially deleted.

9. The therapeutic agent of claim 5, wherein the first composition comprises a therapeutically effective amount of the replication-selective recombinant oncolytic virus, wherein the replication-selective recombinant oncolytic virus is formulated to be administered by intratumoral injection, intraperitonealy, intra-subarachnoidly or intravenously.

10. The therapeutic agent of claim 1, wherein the immune cells include primitive T cells or their precursor cells, NKT cells, or T cell strains.

11. The therapeutic agent of claim 1, wherein the second composition comprises a therapeutically effective amount of the T cell receptor-modified immune cells, wherein the immune cells are formulated to be administered intraarterially, intravenously, hypodermically, intracutaneous, intratumorally, intralympthatically, intralymphnode, intra-subarachnoidly, intramedullarily, intramuscularly, or intraperitoneally.

12. The therapeutic agent of claim 1, wherein the nucleic acid has a coding sequence of the amino acid sequence of at least 98% identity with the amino acid sequence as shown in SEQ ID NO: 24, SEQ ID NO: 31, SEQ ID NO: 32, SEQ ID NO: 36, or SEQ ID NO: 60.

13. A method for treating a tumor and/or cancer, comprising:
   administering the first composition of the therapeutic agent of claim 1 to a patient suffering from a tumor and/or a cancer; and
   administering the second composition of the therapeutic agent of claim 1 to the patient suffering from the tumor and/or the cancer.

14. The method of claim 13, comprising the following steps in a sequential manner:
   1) administering the first composition to the patient suffering from the tumor and/or the cancer; and
   2) administering the second composition of the therapeutic agent to the patient suffering from the tumor and/or the cancer after the administration of the first composition.

15. The method of claim 13, wherein the tumor and/or cancer include: breast cancer, head and neck tumor, synovial cancer, kidney cancer, connective tissue cancer, melanoma, lung cancer, esophageal cancer, colon cancer, rectal cancer, brain cancer, liver cancer, bone cancer, choriocarcinoma, gastrinoma, pheochromocytoma, prolactinoma, von Hippel-Lindau disease, Zollinger-Ellison syndrome, anal cancer, cholangiocarcinoma, bladder cancer, ureteral carcinoma, glioma, neuroblastoma, meningioma, spinal cord tumor, osteochondroma, chondrosarcoma, Ewing's sarcoma, cancer of unknown primary site, carcinoid, fibrosarcoma, Paget's disease, cervix carcinoma, gallbladder cancer, eye cancer, Kaposi's sarcoma, prostate cancer, testicular cancer, cutaneous squamous cell carcinoma, mesothelioma, multiple myeloma, ovarian cancer, pancreatic endocrine tumor, glucagon tumor, pancreatic cancer, penile cancer, pituitary cancer, soft tissue sarcoma, retinoblastoma, small bowel cancer, gastric cancer, thymic cancer, trophoblastic carcinoma, hydatidiform mole, endometrial cancer, vaginal cancer, vulvar cancer, mycosis fungoides, insulinoma, heart cancer, meningeal cancer, blood cancer, peritoneal cancer or pleural cancer.

* * * * *

SEQUENCE LISTING

<160> NUMBER OF SEQ ID NOS: 61

<210> SEQ ID NO 1
<211> LENGTH: 132
<212> TYPE: PRT
<213> ORGANISM: Homo sapiens

<400> SEQUENCE: 1

Met Leu Leu Leu Leu Ile Pro Val Leu Gly Met Ile Phe Ala Leu Arg
1               5                   10                  15

Asp Ala Arg Ala Gln Ser Val Ser Gln His Asn His His Val Ile Leu
            20                  25                  30

Ser Glu Ala Ala Ser Leu Glu Leu Gly Cys Asn Tyr Ser Tyr Gly Gly
        35                  40                  45

Thr Val Asn Leu Phe Trp Tyr Val Gln Tyr Pro Gly Gln His Leu Gln
    50                  55                  60

Leu Leu Leu Lys Tyr Phe Ser Gly Asp Pro Leu Val Lys Gly Ile Lys
65                  70                  75                  80

Gly Phe Glu Ala Glu Phe Ile Lys Ser Lys Phe Ser Phe Asn Leu Arg
                85                  90                  95

Lys Pro Ser Val Gln Trp Ser Asp Thr Ala Glu Tyr Phe Cys Ala Val
            100                 105                 110

Asn Asp Asn Asp Tyr Lys Leu Ser Phe Gly Ala Gly Thr Thr Val Thr
        115                 120                 125

Val Arg Ala Asn
    130

<210> SEQ ID NO 2
<211> LENGTH: 133
<212> TYPE: PRT
<213> ORGANISM: Homo sapiens

<400> SEQUENCE: 2

Met Gly Cys Arg Leu Leu Cys Cys Ala Val Leu Cys Leu Leu Gly Ala
1               5                   10                  15

Val Pro Met Glu Thr Gly Val Thr Gln Thr Pro Arg His Leu Val Met
            20                  25                  30

Gly Met Thr Asn Lys Lys Ser Leu Lys Cys Glu Gln His Leu Gly His
        35                  40                  45

Asn Ala Met Tyr Trp Tyr Lys Gln Ser Ala Lys Lys Pro Leu Glu Leu
    50                  55                  60

Met Phe Val Tyr Ser Leu Glu Glu Arg Val Glu Asn Asn Ser Val Pro
65                  70                  75                  80

Ser Arg Phe Ser Pro Glu Cys Pro Asn Ser Ser His Leu Phe Leu His
                85                  90                  95

Leu His Thr Leu Gln Pro Glu Asp Ser Ala Leu Tyr Leu Cys Ala Ser
            100                 105                 110

Ser Gln Glu Ala Gly Ser Tyr Asn Glu Gln Phe Phe Gly Pro Gly Thr
        115                 120                 125

Arg Leu Thr Val Leu
    130

<210> SEQ ID NO 3
<211> LENGTH: 9
<212> TYPE: PRT
<213> ORGANISM: Homo sapiens

<400> SEQUENCE: 3

```
Lys Ile Phe Gly Ser Leu Ala Phe Leu
1               5
```

<210> SEQ ID NO 4
<211> LENGTH: 272
<212> TYPE: PRT
<213> ORGANISM: Homo sapiens

<400> SEQUENCE: 4

```
Met Leu Leu Leu Leu Ile Pro Val Leu Gly Met Ile Phe Ala Leu Arg
1               5                   10                  15

Asp Ala Arg Ala Gln Ser Val Ser Gln His Asn His His Val Ile Leu
            20                  25                  30

Ser Glu Ala Ala Ser Leu Glu Leu Gly Cys Asn Tyr Ser Tyr Gly Gly
        35                  40                  45

Thr Val Asn Leu Phe Trp Tyr Val Gln Tyr Pro Gly Gln His Leu Gln
    50                  55                  60

Leu Leu Leu Lys Tyr Phe Ser Gly Asp Pro Leu Val Lys Gly Ile Lys
65                  70                  75                  80

Gly Phe Glu Ala Glu Phe Ile Lys Ser Lys Phe Ser Phe Asn Leu Arg
                85                  90                  95

Lys Pro Ser Val Gln Trp Ser Asp Thr Ala Glu Tyr Phe Cys Ala Val
            100                 105                 110

Asn Asp Asn Asp Tyr Lys Leu Ser Phe Gly Ala Gly Thr Thr Val Thr
        115                 120                 125

Val Arg Ala Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270
```

<210> SEQ ID NO 5
<211> LENGTH: 272
<212> TYPE: PRT
<213> ORGANISM: Artificial sequence
<220> FEATURE:
<223> OTHER INFORMATION: Homo sapiens

<400> SEQUENCE: 5

```
Met Leu Leu Leu Leu Ile Pro Val Leu Gly Met Ile Phe Ala Leu Arg
1               5                   10                  15

Asp Ala Arg Ala Gln Ser Val Ser Gln His Asn His His Val Ile Leu
            20                  25                  30
```

Ser Glu Ala Ala Ser Leu Glu Leu Gly Cys Asn Tyr Ser Tyr Gly Gly
            35                  40                  45

Thr Val Asn Leu Phe Trp Tyr Val Gln Tyr Pro Gly Gln His Leu Gln
 50                  55                  60

Leu Leu Leu Lys Tyr Phe Ser Gly Asp Pro Leu Val Lys Gly Ile Lys
 65                  70                  75                  80

Gly Phe Glu Ala Glu Phe Ile Lys Ser Lys Phe Ser Phe Asn Leu Arg
                85                  90                  95

Lys Pro Ser Val Gln Trp Ser Asp Thr Ala Glu Tyr Phe Cys Ala Val
            100                 105                 110

Asn Asp Asn Asp Tyr Lys Leu Ser Phe Gly Ala Gly Thr Thr Val Thr
            115                 120                 125

Val Arg Ala Asn Ile Gln Asn Pro Asp Pro Ala Val Tyr Gln Leu Arg
130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Cys Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
            195                 200                 205

Asn Asn Ser Ile Ile Pro Glu Asp Thr Phe Phe Pro Ser Pro Glu Ser
            210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 6
<211> LENGTH: 268
<212> TYPE: PRT
<213> ORGANISM: Artificial sequence
<220> FEATURE:
<223> OTHER INFORMATION: Homo sapiens, Mus Musculus

<400> SEQUENCE: 6

Met Leu Leu Leu Ile Pro Val Leu Gly Met Ile Phe Ala Leu Arg
 1               5                  10                  15

Asp Ala Arg Ala Gln Ser Val Ser Gln His Asn His His Val Ile Leu
                20                  25                  30

Ser Glu Ala Ala Ser Leu Glu Leu Gly Cys Asn Tyr Ser Tyr Gly Gly
            35                  40                  45

Thr Val Asn Leu Phe Trp Tyr Val Gln Tyr Pro Gly Gln His Leu Gln
 50                  55                  60

Leu Leu Leu Lys Tyr Phe Ser Gly Asp Pro Leu Val Lys Gly Ile Lys
 65                  70                  75                  80

Gly Phe Glu Ala Glu Phe Ile Lys Ser Lys Phe Ser Phe Asn Leu Arg
                85                  90                  95

Lys Pro Ser Val Gln Trp Ser Asp Thr Ala Glu Tyr Phe Cys Ala Val
            100                 105                 110

Asn Asp Asn Asp Tyr Lys Leu Ser Phe Gly Ala Gly Thr Thr Val Thr
            115                 120                 125

Val Arg Ala Asn Ile Gln Asn Pro Glu Pro Ala Val Tyr Gln Leu Lys
130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
                180                 185                 190

Ala Ile Ala Trp Ser Asn Gln Thr Ser Phe Thr Cys Gln Asp Ile Phe
            195                 200                 205

Lys Glu Thr Asn Ala Thr Tyr Pro Ser Ser Asp Val Pro Cys Asp Ala
210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                245                 250                 255

Phe Asn Leu Leu Met Thr Leu Arg Leu Trp Ser Ser
            260                 265

<210> SEQ ID NO 7
<211> LENGTH: 312
<212> TYPE: PRT
<213> ORGANISM: Homo sapiens

<400> SEQUENCE: 7

Met Gly Cys Arg Leu Leu Cys Cys Ala Val Leu Cys Leu Leu Gly Ala
1               5                   10                  15

Val Pro Met Glu Thr Gly Val Thr Gln Thr Pro Arg His Leu Val Met
                20                  25                  30

Gly Met Thr Asn Lys Lys Ser Leu Lys Cys Glu Gln His Leu Gly His
            35                  40                  45

Asn Ala Met Tyr Trp Tyr Lys Gln Ser Ala Lys Lys Pro Leu Glu Leu
        50                  55                  60

Met Phe Val Tyr Ser Leu Glu Glu Arg Val Glu Asn Asn Ser Val Pro
65                  70                  75                  80

Ser Arg Phe Ser Pro Glu Cys Pro Asn Ser Ser His Leu Phe Leu His
                85                  90                  95

Leu His Thr Leu Gln Pro Glu Asp Ser Ala Leu Tyr Leu Cys Ala Ser
                100                 105                 110

Ser Gln Glu Ala Gly Ser Tyr Asn Glu Gln Phe Phe Gly Pro Gly Thr
            115                 120                 125

Arg Leu Thr Val Leu Glu Asp Leu Lys Asn Val Phe Pro Pro Glu Val
130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
                180                 185                 190

Pro Gln Pro Leu Lys Glu Gln Pro Ala Leu Asn Asp Ser Arg Tyr Cys
            195                 200                 205

Leu Ser Ser Arg Leu Arg Val Ser Ala Thr Phe Trp Gln Asn Pro Arg
210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly
305                 310

<210> SEQ ID NO 8
<211> LENGTH: 312
<212> TYPE: PRT
<213> ORGANISM: Artificial sequence
<220> FEATURE:
<223> OTHER INFORMATION: Homo sapiens

<400> SEQUENCE: 8

Met Gly Cys Arg Leu Leu Cys Cys Ala Val Leu Cys Leu Leu Gly Ala
1               5                   10                  15

Val Pro Met Glu Thr Gly Val Thr Gln Thr Pro Arg His Leu Val Met
            20                  25                  30

Gly Met Thr Asn Lys Lys Ser Leu Lys Cys Glu Gln His Leu Gly His
        35                  40                  45

Asn Ala Met Tyr Trp Tyr Lys Gln Ser Ala Lys Lys Pro Leu Glu Leu
    50                  55                  60

Met Phe Val Tyr Ser Leu Glu Glu Arg Val Glu Asn Asn Ser Val Pro
65                  70                  75                  80

Ser Arg Phe Ser Pro Glu Cys Pro Asn Ser Ser His Leu Phe Leu His
                85                  90                  95

Leu His Thr Leu Gln Pro Glu Asp Ser Ala Leu Tyr Leu Cys Ala Ser
            100                 105                 110

Ser Gln Glu Ala Gly Ser Tyr Asn Glu Gln Phe Phe Gly Pro Gly Thr
        115                 120                 125

Arg Leu Thr Val Leu Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Cys Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
        290                 295                 300

Val Lys Arg Lys Asp Ser Arg Gly
305                 310

<210> SEQ ID NO 9
<211> LENGTH: 306
<212> TYPE: PRT
<213> ORGANISM: Artificial sequence
<220> FEATURE:
<223> OTHER INFORMATION: Homo sapiens, Mus Musculus

<400> SEQUENCE: 9

Met Gly Cys Arg Leu Leu Cys Cys Ala Val Leu Cys Leu Leu Gly Ala
1               5                   10                  15

Val Pro Met Glu Thr Gly Val Thr Gln Thr Pro Arg His Leu Val Met
            20                  25                  30

Gly Met Thr Asn Lys Lys Ser Leu Lys Cys Glu Gln His Leu Gly His
                35                  40                  45

Asn Ala Met Tyr Trp Tyr Lys Gln Ser Ala Lys Lys Pro Leu Glu Leu
    50                  55                  60

Met Phe Val Tyr Ser Leu Glu Glu Arg Val Glu Asn Asn Ser Val Pro
65                  70                  75                  80

Ser Arg Phe Ser Pro Glu Cys Pro Asn Ser Ser His Leu Phe Leu His
                85                  90                  95

Leu His Thr Leu Gln Pro Glu Asp Ser Ala Leu Tyr Leu Cys Ala Ser
            100                 105                 110

Ser Gln Glu Ala Gly Ser Tyr Asn Glu Gln Phe Phe Gly Pro Gly Thr
        115                 120                 125

Arg Leu Thr Val Leu Glu Asp Leu Arg Asn Val Thr Pro Pro Lys Val
    130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr Gln Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Thr Leu Val Val Met Ala Met Val Lys Arg Lys
    290                 295                 300

Asn Ser
305

<210> SEQ ID NO 10

```
<211> LENGTH: 396
<212> TYPE: DNA
<213> ORGANISM: Homo sapiens

<400> SEQUENCE: 10
atgctcctgt tgctcatacc agtgctgggg atgattttg ccctgagaga tgccagagcc      60
cagtctgtga gccagcataa ccaccacgta attctctctg aagcagcctc actggagttg     120
ggatgcaact attcctatgg tggaactgtt aatctcttct ggtatgtcca gtaccctggt    180
caacaccttc agcttctcct caagtacttt tcaggggatc cactggttaa aggcatcaag    240
ggctttgagg ctgaatttat aaagagtaaa ttctcccttta atctgaggaa accctctgtg   300
cagtggagtg acacagctga gtacttctgt gccgtgaatg ataacgacta caagctcagc    360
tttggagccg aaccacagt aactgtaaga gcaaac                                396

<210> SEQ ID NO 11
<211> LENGTH: 399
<212> TYPE: DNA
<213> ORGANISM: Homo sapiens

<400> SEQUENCE: 11
atgggctgca ggctgctctg ctgtgcggtt ctctgtctcc tgggagcggt ccccatggaa     60
acgggagtta cgcagacacc aagacacctg gtcatgggaa tgacaaataa gaagtctttg   120
aaatgtgaac aacatctggg tcataacgct atgtattggt acaagcaaag tgctaagaag  180
ccactggagc tcatgtttgt ctacagtctt gaagaacggg ttgaaaacaa cagtgtgcca 240
agtcgcttct cacctgaatg ccccaacagc tctcacttat ccttcacct acacaccctg   300
cagccagaag actcggccct gtatctctgc gccagcagcc aagaagccgg ttcctacaat  360
gagcagttct cgggccagg gacacggctc accgtgcta                            399

<210> SEQ ID NO 12
<211> LENGTH: 819
<212> TYPE: DNA
<213> ORGANISM: Homo sapiens

<400> SEQUENCE: 12
atgctcctgt tgctcatacc agtgctgggg atgattttg ccctgagaga tgccagagcc      60
cagtctgtga gccagcataa ccaccacgta attctctctg aagcagcctc actggagttg    120
ggatgcaact attcctatgg tggaactgtt aatctcttct ggtatgtcca gtaccctggt   180
caacaccttc agcttctcct caagtacttt tcaggggatc cactggttaa aggcatcaag   240
ggctttgagg ctgaatttat aaagagtaaa ttctccttta atctgaggaa accctctgtg   300
cagtggagtg acacagctga gtacttctgt gccgtgaatg ataacgacta caagctcagc    360
tttggagccg aaccacagt aactgtaaga gcaaatatcc agaaccctga ccctgccgtg   420
taccagctga gagactctaa atccagtgac aagtctgtct gcctattcac cgattttgat  480
tctcaaacaa atgtgtcaca agtaaggat tctgatgtgt atatcacaga caaaccgtg    540
ctagacatga ggtctatgga cttcaagagc aacagtgctg tggcctggag caacaaatct   600
gactttgcat gtgcaaacgc cttcaacaac agcattattc cagaagacac cttcttcccc  660
agcccagaaa gttcctgtga tgtcaagctg gtcgagaaaa gctttgaaac agatacgaac   720
ctaaactttc aaaacctgtc agtgattggg ttccgaatcc tcctcctgaa agtggccggg   780
tttaatctgc tcatgacgct gcggctgtgg tccagctga                          819
```

<210> SEQ ID NO 13
<211> LENGTH: 819
<212> TYPE: DNA
<213> ORGANISM: Artificial sequence
<220> FEATURE:
<223> OTHER INFORMATION: Homo sapiens

<400> SEQUENCE: 13

```
atgctcctgt tgctcatacc agtgctgggg atgattttg ccctgagaga tgccagagcc      60
cagtctgtga gccagcataa ccaccacgta attctctctg aagcagcctc actggagttg     120
ggatgcaact attcctatgg tggaactgtt aatctcttct ggtatgtcca gtaccctggt     180
caacaccttc agcttctcct caagtacttt tcagggatc cactggttaa aggcatcaag      240
ggctttgagg ctgaatttat aaagagtaaa ttctcctta atctgaggaa accctctgtg      300
cagtggagtg acacagctga gtacttctgt gccgtgaatg ataacgacta caagctcagc     360
tttggagccg gaaccacagt aactgtaaga gcaaatatcc agaaccctga ccctgccgtg     420
taccagctga gagactctaa atccagtgac aagtctgtct gcctattcac cgattttgat     480
tctcaaacaa atgtgtcaca agtaaggat tctgatgtgt atatcacaga caaatgcgtg      540
ctagacatga ggtctatgga cttcaagagc aacagtgctg tggcctggag caacaaatct     600
gactttgcat gtgcaaacgc cttcaacaac agcattattc cagaagacac cttcttcccc     660
agcccagaaa gttcctgtga tgtcaagctg gtcgagaaaa gctttgaaac agatacgaac     720
ctaaactttc aaaacctgtc agtgattggg ttccgaatcc tcctcctgaa agtggccggg     780
tttaatctgc tcatgacgct gcggctgtgg tccagctga                            819
```

<210> SEQ ID NO 14
<211> LENGTH: 807
<212> TYPE: DNA
<213> ORGANISM: Artificial sequence
<220> FEATURE:
<223> OTHER INFORMATION: Homo sapiens, Mus Musculus

<400> SEQUENCE: 14

```
atgctcctgt tgctcatacc agtgctgggg atgattttg ccctgagaga tgccagagcc      60
cagtctgtga gccagcataa ccaccacgta attctctctg aagcagcctc actggagttg     120
ggatgcaact attcctatgg tggaactgtt aatctcttct ggtatgtcca gtaccctggt     180
caacaccttc agcttctcct caagtacttt tcagggatc cactggttaa aggcatcaag      240
ggctttgagg ctgaatttat aaagagtaaa ttctcctta atctgaggaa accctctgtg      300
cagtggagtg acacagctga gtacttctgt gccgtgaatg ataacgacta caagctcagc     360
tttggagccg gaaccacagt aactgtaaga gcaaacatcc agaacccaga acctgctgtg     420
taccagttaa aagatcctcg gtctcaggac agcaccctct gcctgttcac cgactttgac     480
tcccaaatca atgtgccgaa aaccatggaa tctggaacgt tcatcactga caaaactgtg     540
ctggacatga agctatgga ttccaagagc aatgggccca ttgcctggag caaccagaca     600
agcttcacct gccaagatat cttcaaagag accaacgcca cctacccag ttcagacgtt      660 ccctgtgatg ccacgttgac cgagaaaagc tttgaaacag atatgaacct aaactttcaa    720
aacctgtcag ttatgggact ccgaatcctc ctgctgaaag tagcgggatt taacctgctc    780
atgacgctga ggctgtggtc cagttga                                         807
```

<210> SEQ ID NO 15
<211> LENGTH: 939
<212> TYPE: DNA

<213> ORGANISM: Homo sapiens

<400> SEQUENCE: 15

| | | | | | |
|---|---|---|---|---|---|
| atgggctgca | ggctgctctg | ctgtgcggtt | ctctgtctcc | tgggagcggt | ccccatggaa | 60
| acgggagtta | cgcagacacc | aagacacctg | gtcatgggaa | tgacaaataa | gaagtctttg | 120
| aaatgtgaac | aacatctggg | tcataacgct | atgtattggt | acaagcaaag | tgctaagaag | 180
| ccactggagc | tcatgtttgt | ctacagtctt | gaagaacggg | ttgaaaacaa | cagtgtgcca | 240
| agtcgcttct | cacctgaatg | ccccaacagc | tctcacttat | tccttcacct | acacaccctg | 300
| cagccagaag | actcggccct | gtatctctgc | gccagcagcc | aagaagccgg | ttcctacaat | 360
| gagcagttct | cgggccagg | acacggctc | accgtgctag | aggacctgaa | aaacgtgttc | 420
| ccacccgagg | tcgctgtgtt | tgagccatca | gaagcagaga | tctcccacac | ccaaaaggcc | 480
| acactggtat | gcctggccac | aggcttctac | cccgaccacg | tggagctgag | ctggtgggtg | 540
| aatgggaagg | aggtgcacag | tggggtcagc | acagacccgc | agcccctcaa | ggagcagccc | 600
| gccctcaatg | actccagata | ctgcctgagc | agccgcctga | gggtctcggc | caccttctgg | 660
| cagaaccccc | gcaaccactt | ccgctgtcaa | gtccagttct | acgggctctc | ggagaatgac | 720
| gagtggaccc | aggatagggc | caaacccgtc | acccagatcg | tcagcgccga | ggcctggggt | 780
| agagcagact | gtggcttcac | ctccgagtct | taccagcaag | gggtcctgtc | tgccaccatc | 840
| ctctatgaga | tcttgctagg | gaaggccacc | ttgtatgccg | tgctggtcag | tgccctcgtg | 900
| ctgatggcca | tggtcaagag | aaaggattcc | agaggctaa | | | 939

<210> SEQ ID NO 16
<211> LENGTH: 939
<212> TYPE: DNA
<213> ORGANISM: Homo sapiens

<400> SEQUENCE: 16

| | | | | | |
|---|---|---|---|---|---|
| atgggctgca | ggctgctctg | ctgtgcggtt | ctctgtctcc | tgggagcggt | ccccatggaa | 60
| acgggagtta | cgcagacacc | aagacacctg | gtcatgggaa | tgacaaataa | gaagtctttg | 120
| aaatgtgaac | aacatctggg | tcataacgct | atgtattggt | acaagcaaag | tgctaagaag | 180
| ccactggagc | tcatgtttgt | ctacagtctt | gaagaacggg | ttgaaaacaa | cagtgtgcca | 240
| agtcgcttct | cacctgaatg | ccccaacagc | tctcacttat | tccttcacct | acacaccctg | 300
| cagccagaag | actcggccct | gtatctctgc | gccagcagcc | aagaagccgg | ttcctacaat | 360
| gagcagttct | cgggccagg | acacggctc | accgtgctag | aggacctgaa | aaacgtgttc | 420
| ccacccgagg | tcgctgtgtt | tgagccatca | gaagcagaga | tctcccacac | ccaaaaggcc | 480
| acactggtat | gcctggccac | aggcttctac | cccgaccacg | tggagctgag | ctggtgggtg | 540
| aatgggaagg | aggtgcacag | tggggtctgc | acagacccgc | agcccctcaa | ggagcagccc | 600
| gccctcaatg | actccagata | ctgcctgagc | agccgcctga | gggtctcggc | caccttctgg | 660
| cagaaccccc | gcaaccactt | ccgctgtcaa | gtccagttct | acgggctctc | ggagaatgac | 720
| gagtggaccc | aggatagggc | caaacccgtc | acccagatcg | tcagcgccga | ggcctggggt | 780
| agagcagact | gtggcttcac | ctccgagtct | taccagcaag | gggtcctgtc | tgccaccatc | 840
| ctctatgaga | tcttgctagg | gaaggccacc | ttgtatgccg | tgctggtcag | tgccctcgtg | 900
| ctgatggcca | tggtcaagag | aaaggattcc | agaggctaa | | | 939

<210> SEQ ID NO 17
<211> LENGTH: 921

```
<212> TYPE: DNA
<213> ORGANISM: Homo sapiens

<400> SEQUENCE: 17
atgggctgca ggctgctctg ctgtgcggtt ctctgtctcc tgggagcggt ccccatggaa      60 acggagtta cgcagacacc aagacacctg gtcatgggaa tgacaaataa gaagtctttg     120
aaatgtgaac aacatctggg tcataacgct atgtattggt acaagcaaag tgctaagaag     180
ccactggagc tcatgtttgt ctacagtctt gaagaacggg ttgaaaacaa cagtgtgcca     240
agtcgcttct cacctgaatg ccccaacagc tctcacttat ccttcacct acacaccctg      300 cagccagaag actcggccct gtatctctgc gccagcagcc aagaagccgg ttcctacaat     360
gagcagttct tcgggccagg gacacggctc accgtgctag aggatctgag aaatgtgact     420
ccacccaagg tctccttgtt tgagccatca aaagcagaga ttgcaaacaa acaaaaggct     480
accctcgtgt gcttggccag ggcttcttc cctgaccacg tggagctgag ctggtgggtg      540
aatggcaagg aggtccacag tggggtcagc acggaccctc aggcctacaa ggagagcaat     600
tatagctact gcctgagcag ccgcctgagg gtctctgcta ccttctggca caatcctcgc     660
aaccacttcc gctgccaagt gcagttccat gggctttcag aggaggacaa gtggccagag     720
ggctcaccca aacctgtcac acagaacatc agtgcagagg cctggggccg agcagactgt     780
gggattacct cagcatccta tcaacaaggg gtcttgtctg ccaccatcct ctatgagatc     840
ctgctaggga agccacccct gtatgctgtg cttgtcagta cactggtggt gatggctatg     900
gtcaaaagaa agaattcata a                                                921

<210> SEQ ID NO 18
<211> LENGTH: 1851
<212> TYPE: DNA
<213> ORGANISM: Artificial sequence
<220> FEATURE:
<223> OTHER INFORMATION: The sequence is synthesized

<400> SEQUENCE: 18
atgggctgca ggctgctctg ctgtgcggtt ctctgtctcc tgggagcggt ccccatggaa      60 acggagtta cgcagacacc aagacacctg gtcatgggaa tgacaaataa gaagtctttg     120
aaatgtgaac aacatctggg tcataacgct atgtattggt acaagcaaag tgctaagaag     180
ccactggagc tcatgtttgt ctacagtctt gaagaacggg ttgaaaacaa cagtgtgcca     240
agtcgcttct cacctgaatg ccccaacagc tctcacttat ccttcacct acacaccctg      300 cagccagaag actcggccct gtatctctgc gccagcagcc aagaagccgg ttcctacaat     360
gagcagttct tcgggccagg gacacggctc accgtgctag aggacctgaa aacgtgttc      420 ccacccgagg tcgctgtgtt tgagccatca gaagcagaga tctcccacac ccaaaaggcc     480
acactggtat gcctggccac aggcttctac cccgaccacg tggagctgag ctggtgggtg     540
aatgggaagg aggtgcacag tggggtcagc acagaccgc agcccctcaa ggagcagccc     600
gccctcaatg actccagata ctgcctgagc agccgcctga gggtctcggc caccttctgg     660
cagaaccccc gcaaccactt ccgctgtcaa gtccagttct acgggctctc ggagaatgac     720
gagtggaccc aggataggc caaacccgtc acccagatct cagcgccga ggcctggggt      780 agagcagact gtggcttcac ctccgagtct taccagcaag gggtcctgtc tgccaccatc     840
ctctatgaga tcttgctagg gaaggccacc ttgtatgccg tgctggtcag tgccctcgtg     900
ctgatggcca tggtcaagag aaaggattcc agaggccgtg ccaagcgatc cggaagcgga    960
```

| | |
|---|---|
| gcccctgtaa agcagacttt gaattttgac cttctcaagt tggcgggaga cgtcgagtcc | 1020 |
| aaccctgggc ccatgctcct gttgctcata ccagtgctgg ggatgatttt tgccctgaga | 1080 |
| gatgccagag cccagtctgt gagccagcat aaccaccacg taattctctc tgaagcagcc | 1140 |
| tcactggagt tgggatgcaa ctattcctat ggtggaactg ttaatctctt ctggtatgtc | 1200 |
| cagtaccctg gtcaacacct tcagcttctc ctcaagtact tttcagggga tccactggtt | 1260 |
| aaaggcatca agggctttga ggctgaattt ataaagagta aattctcctt taatctgagg | 1320 |
| aaaccctctg tgcagtggag tgacacagct gagtacttct gtgccgtgaa tgataacgac | 1380 |
| tacaagctca gctttggagc cggaaccaca gtaactgtaa gagcaaatat ccagaaccct | 1440 |
| gaccctgccg tgtaccagct gagagactct aaatccagtg acaagtctgt ctgcctattc | 1500 |
| accgattttg attctcaaac aaatgtgtca caaagtaagg attctgatgt gtatatcaca | 1560 |
| gacaaaaccg tgctagacat gaggtctatg gacttcaaga gcaacagtgc tgtggcctgg | 1620 |
| agcaacaaat ctgactttgc atgtgcaaac gccttcaaca acagcattat tccagaagac | 1680 |
| accttcttcc ccagcccaga aagttcctgt gatgtcaagc tggtcgagaa aagctttgaa | 1740 |
| acagatacga acctaaactt tcaaaacctg tcagtgattg ggttccgaat cctcctcctg | 1800 |
| aaagtggccg ggtttaatct gctcatgacg ctgcggctgt ggtccagctg a | 1851 |

<210> SEQ ID NO 19
<211> LENGTH: 1851
<212> TYPE: DNA
<213> ORGANISM: Artificial sequence
<220> FEATURE:
<223> OTHER INFORMATION: The sequence is synthesized

<400> SEQUENCE: 19

| | |
|---|---|
| atgggctgca ggctgctctg ctgtgcggtt ctctgtctcc tgggagcggt ccccatggaa | 60 |
| acgggagtta cgcagacacc aagacacctg gtcatgggaa tgacaaataa gaagtctttg | 120 |
| aaatgtgaac aacatctggg tcataacgct atgtattggt acaagcaaag tgctaagaag | 180 |
| ccactggagc tcatgtttgt ctacagtctt gaagaacggg ttgaaaacaa cagtgtgcca | 240 |
| agtcgcttct cacctgaatg ccccaacagc tctcacttat tccttcacct acacaccctg | 300 |
| cagccagaag actcggccct gtatctctgc gccagcagcc aagaagccgg ttcctacaat | 360 |
| gagcagttct cgggccagg acacggctc accgtgctag aggacctgaa aaacgtgttc | 420 |
| ccacccgagg tcgctgtgtt tgagccatca gaagcagaga tctcccacac ccaaaaggcc | 480 |
| acactggtat gcctggccac aggcttctac cccgaccacg tggagctgag ctggtgggtg | 540 |
| aatgggaagg aggtgcacag tggggtctgc acagacccgc agcccctcaa ggagcagccc | 600 |
| gccctcaatg actccagata ctgcctgagc agccgcctga gggtctcggc caccttctgg | 660 |
| cagaaccccc gcaaccactt ccgctgtcaa gtccagttct acgggctctc ggagaatgac | 720 |
| gagtggaccc aggatagggc caaacccgtc acccagatcg tcagcgccga ggcctggggt | 780 |
| agagcagact gtggcttcac ctccgagtct taccagcaag gggtcctgtc tgccaccatc | 840 |
| ctctatgaga tcttgctagg aaaggccacc ttgtatgccg tgctggtcag tgccctcgtg | 900 |
| ctgatggcca tggtcaagag aaaggatcc agaggccgtg ccaagcgatc cggaagcgga | 960 |
| gcccctgtaa agcagacttt gaattttgac cttctcaagt tggcgggaga cgtcgagtcc | 1020 |
| aaccctgggc ccatgctcct gttgctcata ccagtgctgg ggatgatttt tgccctgaga | 1080 |
| gatgccagag cccagtctgt gagccagcat aaccaccacg taattctctc tgaagcagcc | 1140 |
| tcactggagt tgggatgcaa ctattcctat ggtggaactg ttaatctctt ctggtatgtc | 1200 |

```
cagtaccctg gtcaacacct tcagcttctc ctcaagtact tttcagggga tccactggtt    1260
aaaggcatca agggctttga ggctgaattt ataaagagta aattctcctt taatctgagg    1320
aaaccctctg tgcagtggag tgacacagct gagtacttct gtgccgtgaa tgataacgac    1380
tacaagctca gctttggagc cggaaccaca gtaactgtaa gagcaaatat ccagaaccct    1440
gaccctgccg tgtaccagct gagagactct aaatccagtg acaagtctgt ctgcctattc    1500
accgattttg attctcaaac aaatgtgtca caaagtaagg attctgatgt gtatatcaca    1560
gacaaatgcg tgctagacat gaggtctatg gacttcaaga gcaacagtgc tgtggcctgg    1620
agcaacaaat ctgactttgc atgtgcaaac gccttcaaca acagcattat tccagaagac    1680
accttcttcc ccagcccaga aagttcctgt gatgtcaagc tggtcgagaa aagctttgaa    1740
acagatacga acctaaactt tcaaaacctg tcagtgattg ggttccgaat cctcctcctg    1800
aaagtggccg ggtttaatct gctcatgacg ctgcggctgt ggtccagctg a             1851
```

<210> SEQ ID NO 20
<211> LENGTH: 1821
<212> TYPE: DNA
<213> ORGANISM: Artificial sequence
<220> FEATURE:
<223> OTHER INFORMATION: The sequence is synthesized

<400> SEQUENCE: 20

```
atgggctgca ggctgctctg ctgtgcggtt ctctgtctcc tgggagcggt ccccatggaa      60
acgggagtta cgcagacacc aagacacctg gtcatgggaa tgacaaataa gaagtctttg     120
aaatgtgaac aacatctggg tcataacgct atgtattggt acaagcaaag tgctaagaag     180
ccactggagc tcatgtttgt ctacagtctt gaagaacggg ttgaaaacaa cagtgtgcca     240
agtcgcttct cacctgaatg ccccaacagc tctcacttat tccttcacct acacaccctg     300
cagccagaag actcggccct gtatctctgc gccagcagcc aagaagccgg ttcctacaat     360
gagcagttct tcgggccagg gacacggctc accgtgctag aggatctgag aaatgtgact     420
ccacccaagg tctccttgtt tgagccatca aaagcagaga ttgcaaacaa caaaaggct     480 accctcgtgt gcttggccag gggcttcttc cctgaccacg tggagctgag ctggtgggtg     540
aatggcaagg aggtccacag tggggtcagc acgaccctc aggcctacaa ggagagcaat     600
tatagctact gcctgagcag ccgcctgagg gtctctgcta ccttctggca caatcctcgc     660
aaccacttcc gctgccaagt gcagttccat gggctttcag aggaggacaa gtggccagag     720
ggctcaccca aacctgtcac acagaacatc agtgcagagg cctggggccg agcagactgt     780
gggattacct cagcatccta tcaacaaggg gtcttgtctg ccaccatcct ctatgagatc     840
ctgctaggga agccaccct gtatgctgtg cttgtcagta cactggtggt gatggctatg     900
gtcaaaagaa agaattcacg tgccaagcga tccggaagcg agcccctgt aaagcagact     960 ttgaattttg accttctcaa gttggcggga acgtcgagt ccaaccctgg gcccatgctc    1020
ctgttgctca taccagtgct ggggatgatt tttgccctga gatgccag gcccagtct     1080 gtgagccagc ataaccacca cgtaattctc tctgaagcag cctcactgga gttgggatgc    1140
aactattcct atggtggaac tgttaatctc ttctggtatg tccagtaccc tggtcaacac    1200
cttcagcttc tcctcaagta cttttcaggg gatccactgg ttaaaggcat caagggcttt    1260
gaggctgaat ttataaagag taaattctcc tttaatctga ggaaaccctc tgtgcagtgg    1320
agtgacacag ctgagtactt ctgtgccgtg aatgataacg actacaagct cagctttgga    1380
```

```
gccggaacca cagtaactgt aagagcaaac atccagaacc cagaacctgc tgtgtaccag    1440
ttaaaagatc ctcggtctca ggacagcacc ctctgcctgt tcaccgactt tgactcccaa    1500
atcaatgtgc cgaaaaccat ggaatctgga acgttcatca ctgacaaaac tgtgctggac    1560
atgaaagcta tggattccaa gagcaatggg gccattgcct ggagcaacca gacaagcttc    1620
acctgccaag atatcttcaa agagaccaac gccacctacc ccagttcaga cgttccctgt    1680
gatgccacgt tgaccgagaa aagctttgaa acagatatga acctaaactt tcaaaacctg    1740
tcagttatgg gactccgaat cctcctgctg aaagtagcgg gatttaacct gctcatgacg    1800
ctgaggctgt ggtccagttg a                                              1821
```

<210> SEQ ID NO 21
<211> LENGTH: 1255
<212> TYPE: PRT
<213> ORGANISM: Homo sapiens

<400> SEQUENCE: 21

```
Met Glu Leu Ala Ala Leu Cys Arg Trp Gly Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
```

```
            290                 295                 300
Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
                340                 345                 350

Val Arg Ala Val Thr Ser Ala Asn Ile Gln Glu Phe Ala Gly Cys Lys
                355                 360                 365

Lys Ile Phe Gly Ser Leu Ala Phe Leu Pro Glu Ser Phe Asp Gly Asp
            370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
                420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
            450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
                500                 505                 510

Gln Leu Cys Ala Arg Gly His Cys Trp Gly Pro Gly Pro Thr Gln Cys
            515                 520                 525

Val Asn Cys Ser Gln Phe Leu Arg Gly Gln Glu Cys Val Glu Glu Cys
            530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Ala Cys Gln
            610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Leu Gly Val Val Phe Gly
                660                 665                 670

Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
            690                 695                 700

Ala Met Pro Asn Gln Ala Gln Met Arg Ile Leu Lys Glu Thr Glu Leu
705                 710                 715                 720
```

-continued

```
Arg Lys Val Lys Val Leu Gly Ser Gly Ala Phe Gly Thr Val Tyr Lys
            725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
            755                 760                 765

Asp Glu Ala Tyr Val Met Ala Gly Val Gly Ser Pro Tyr Val Ser Arg
            770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
            805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
            835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
            885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
            915                 920                 925

Arg Glu Ile Pro Asp Leu Leu Glu Lys Gly Glu Arg Leu Pro Gln Pro
            930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
            965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
            995                 1000                1005

Leu Glu Asp Asp Asp Met Gly Asp Leu Val Asp Ala Glu Glu Tyr
       1010                1015                1020

Leu Val Pro Gln Gln Gly Phe Phe Cys Pro Asp Pro Ala Pro Gly
       1025                1030                1035

Ala Gly Gly Met Val His His Arg His Arg Ser Ser Ser Thr Arg
       1040                1045                1050

Ser Gly Gly Gly Asp Leu Thr Leu Gly Leu Glu Pro Ser Glu Glu
       1055                1060                1065

Glu Ala Pro Arg Ser Pro Leu Ala Pro Ser Glu Gly Ala Gly Ser
       1070                1075                1080

Asp Val Phe Asp Gly Asp Leu Gly Met Gly Ala Ala Lys Gly Leu
       1085                1090                1095

Gln Ser Leu Pro Thr His Asp Pro Ser Pro Leu Gln Arg Tyr Ser
       1100                1105                1110

Glu Asp Pro Thr Val Pro Leu Pro Ser Glu Thr Asp Gly Tyr Val
       1115                1120                1125
```

```
Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 22
<211> LENGTH: 10
<212> TYPE: PRT
<213> ORGANISM: Homo sapiens

<400> SEQUENCE: 22

Ser Leu Ala Phe Leu Pro Glu Ser Phe Asp
1               5                   10

<210> SEQ ID NO 23
<211> LENGTH: 606
<212> TYPE: PRT
<213> ORGANISM: Artificial sequence
<220> FEATURE:
<223> OTHER INFORMATION: The sequence is synthesized

<400> SEQUENCE: 23

Met Gly Cys Arg Leu Leu Cys Cys Ala Val Leu Cys Leu Gly Ala
1               5                   10                  15

Val Pro Met Glu Thr Gly Val Thr Gln Thr Pro Arg His Leu Val Met
                20                  25                  30

Gly Met Thr Asn Lys Lys Ser Leu Lys Cys Glu Gln His Leu Gly His
                35                  40                  45

Asn Ala Met Tyr Trp Tyr Lys Gln Ser Ala Lys Lys Pro Leu Glu Leu
50                  55                  60

Met Phe Val Tyr Ser Leu Glu Glu Arg Val Glu Asn Asn Ser Val Pro
65                  70                  75                  80

Ser Arg Phe Ser Pro Glu Cys Pro Asn Ser Ser His Leu Phe Leu His
                85                  90                  95

Leu His Thr Leu Gln Pro Glu Asp Ser Ala Leu Tyr Leu Cys Ala Ser
                100                 105                 110

Ser Gln Glu Ala Gly Ser Tyr Asn Glu Gln Phe Phe Gly Pro Gly Thr
                115                 120                 125

Arg Leu Thr Val Leu Glu Asp Leu Arg Asn Val Thr Pro Pro Lys Val
                130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
```

```
            165                 170                 175
Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg
            195                 200                 205

Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr Gln Gln Gly Val Leu
            260                 265                 270

Ser Ala Thr Ile Leu Tyr Glu Ile Leu Leu Gly Lys Ala Thr Leu Tyr
            275                 280                 285

Ala Val Leu Val Ser Thr Leu Val Met Ala Met Val Lys Arg Lys
            290                 295                 300

Asn Ser Arg Ala Lys Arg Ser Gly Ser Gly Ala Pro Val Lys Gln Thr
305                 310                 315                 320

Leu Asn Phe Asp Leu Leu Lys Leu Ala Gly Asp Val Glu Ser Asn Pro
                325                 330                 335

Gly Pro Met Leu Leu Leu Leu Ile Pro Val Leu Gly Met Ile Phe Ala
            340                 345                 350

Leu Arg Asp Ala Arg Ala Gln Ser Val Ser Gln His Asn His His Val
            355                 360                 365

Ile Leu Ser Glu Ala Ala Ser Leu Glu Leu Gly Cys Asn Tyr Ser Tyr
    370                 375                 380

Gly Gly Thr Val Asn Leu Phe Trp Tyr Val Gln Tyr Pro Gly Gln His
385                 390                 395                 400

Leu Gln Leu Leu Leu Lys Tyr Phe Ser Gly Asp Pro Leu Val Lys Gly
                405                 410                 415

Ile Lys Gly Phe Glu Ala Glu Phe Ile Lys Ser Lys Phe Ser Phe Asn
            420                 425                 430

Leu Arg Lys Pro Ser Val Gln Trp Ser Asp Thr Ala Glu Tyr Phe Cys
            435                 440                 445

Ala Val Asn Asp Asn Asp Tyr Lys Leu Ser Phe Gly Ala Gly Thr Thr
            450                 455                 460

Val Thr Val Arg Ala Asn Ile Gln Asn Pro Glu Pro Ala Val Tyr Gln
465                 470                 475                 480

Leu Lys Asp Pro Arg Ser Gln Asp Ser Thr Leu Cys Leu Phe Thr Asp
                485                 490                 495

Phe Asp Ser Gln Ile Asn Val Pro Lys Thr Met Glu Ser Gly Thr Phe
            500                 505                 510

Ile Thr Asp Lys Thr Val Leu Asp Met Lys Ala Met Asp Ser Lys Ser
            515                 520                 525

Asn Gly Ala Ile Ala Trp Ser Asn Gln Thr Ser Phe Thr Cys Gln Asp
            530                 535                 540

Ile Phe Lys Glu Thr Asn Ala Thr Tyr Pro Ser Ser Asp Val Pro Cys
545                 550                 555                 560

Asp Ala Thr Leu Thr Glu Lys Ser Phe Glu Thr Asp Met Asn Leu Asn
                565                 570                 575

Phe Gln Asn Leu Ser Val Met Gly Leu Arg Ile Leu Leu Leu Lys Val
            580                 585                 590
```

Ala Gly Phe Asn Leu Leu Met Thr Leu Arg Leu Trp Ser Ser
            595                 600                 605

<210> SEQ ID NO 24
<211> LENGTH: 126
<212> TYPE: PRT
<213> ORGANISM: Artificial sequence
<220> FEATURE:
<223> OTHER INFORMATION: The sequence is synthesized

<400> SEQUENCE: 24

Met Lys Gly Ser Ile Phe Thr Leu Phe Leu Phe Ser Val Leu Phe Ala
1               5                   10                  15

Ile Ser Glu Val Arg Ser Lys Ile Phe Gly Ser Leu Ala Phe Leu Arg
            20                  25                  30

Arg Lys Arg Lys Ile Phe Gly Ser Leu Ala Phe Leu Arg Arg Lys Arg
        35                  40                  45

Lys Ile Phe Gly Ser Leu Ala Phe Leu Arg Arg Lys Arg Lys Ile Phe
    50                  55                  60

Gly Ser Leu Ala Phe Leu Arg Arg Lys Arg Lys Ile Phe Gly Ser Leu
65                  70                  75                  80

Ala Phe Leu Arg Arg Lys Arg Lys Ile Phe Gly Ser Leu Ala Phe Leu
                85                  90                  95

Arg Arg Lys Arg Lys Ile Phe Gly Ser Leu Ala Phe Leu Arg Arg Lys
            100                 105                 110

Arg Lys Ile Phe Gly Ser Leu Ala Phe Leu Lys Asp Glu Leu
        115                 120                 125

<210> SEQ ID NO 25
<211> LENGTH: 378
<212> TYPE: DNA
<213> ORGANISM: Artificial sequence
<220> FEATURE:
<223> OTHER INFORMATION: The sequence is synthesized

<400> SEQUENCE: 25
atgaaaggtt ccatcttcac attgtttttg ttctccgtat tgttcgcaat cagcgaagtc      60
cgatcaaaaa tatttgggtc tctcgcattc ctccgcagaa agaggaaaat cttcggtagt     120
ttggccttcc ttaggcgaaa gagaaagata tttggaagcc tggccttcct gcgacgcaaa     180
cggaaaatct tcggctcact ggcattcttg aggagaaagc gcaaaatatt cgggtctttg     240
gcctttctgc gccggaagcg caagatcttc ggtccttgg cttcttgag acgaaaacgc       300 aaaatatttg gtctcttgc cttcctcagg cgaaagcgga agattttcgg ttcccttgcc     360
ttccttaaag acgagctt                                                   378

<210> SEQ ID NO 26
<211> LENGTH: 1569
<212> TYPE: DNA
<213> ORGANISM: Artificial sequence
<220> FEATURE:
<223> OTHER INFORMATION: The sequence is synthesized

<400> SEQUENCE: 26
atggccgtca tggcgccccg aaccctcgtc ctgctactct cgggggctct ggccctgacc      60
cagacctggg cgggctctca ctccatgagg tatttcttca catccgtgtc ccggcccggc     120
cgcggggagc cccgcttcat cgcagtgggc tacgtggacg acacgcagtt cgtgcggttc     180
gacagcgacg ccgcgagcca gaggatggag ccgcgggcgc cgtggataga gcaggagggt     240

```
ccggagtatt gggacgggga gacacggaaa gtgaaggccc actcacagac tcaccgagtg    300
gacctgggga ccctgcgcgg ctactacaac cagagcgagg ccggttctca caccgtccag    360
aggatgtatg gctgcgacgt ggggtcggac tggcgcttcc tccgcgggta ccaccagtac    420
gcctacgacg gcaaggatta catcgccctg aaagaggacc tgcgctcttg gaccgcggcg    480
gacatggcag ctcagaccac caagcacaag tgggaggcgg cccatgtggc ggagcagttg    540
agagcctacc tggagggcac gtgcgtggag tggctccgca gatacctgga gaacgggaag    600
gagacgctgc agcgcacgga cgcccccaaa acgcatatga ctcaccacgc tgtctctgac    660
catgaagcca ccctgaggtg ctgggccctg agcttctacc ctgcggagat cacactgacc    720
tggcagcggg atggggagga ccagacccag gacacggagc tcgtggagac caggcctgca    780
ggggatggaa ccttccagaa gtgggcggct gtggtggtgc cttctggaca ggagcagaga    840
tacacctgcc atgtgcagca tgagggtttg cccaagcccc tcaccctgag atgggagccg    900
tcttcccagc ccaccatccc catcgtgggc atcattgctg gcctggttct ctttggagct    960
gtgatcactg gagctgtggt cgctgctgtg atgtggagga ggaagagctc agatagaaaa   1020
ggagggagct actctcaggc tgcaagcagt gacagtgccc agggctctga tgtgtctctc   1080
acagcttgta aagtgcgtgc caagcgatcc ggaagcggag cccctgtaaa gcagactttg   1140
aattttgacc ttctcaagtt ggcgggagac gtcgagtcca accctgggcc catgaaaggt   1200
tccatcttca cattgttttt gttctccgta ttgttcgcaa tcagcgaagt ccgatcaaaa   1260
atatttgggt ctctcgcatt cctccgcaga aagaggaaaa tcttcggtag tttggccttc   1320
cttaggcgaa agagaaagat atttggaagc ctggccttcc tgcgacgcaa acggaaaatc   1380
ttcggctcac tggcattctt gaggagaaag cgcaaaatat tcgggtcttt ggcctttctg   1440
cgccggaagc gcaagatctt cgggtccttg gctttcttga cgaaaacg caaaatattt   1500 gggtctcttg ccttcctcag gcgaaagcgg aagattttcg gttcccttgc cttccttaaa   1560
gacgagctt                                                         1569
```

<210> SEQ ID NO 27
<211> LENGTH: 1572
<212> TYPE: DNA
<213> ORGANISM: Artificial sequence
<220> FEATURE:
<223> OTHER INFORMATION: The sequence is synthesized

<400> SEQUENCE: 27

```
atgaaaggtt ccatcttcac attgttttg ttctccgtat tgttcgcaat cagcgaagtc     60
cgatcaaaaa tatttgggtc tctcgcattc ctccgcagaa agaggaaaat cttcggtagt    120
ttggccttcc ttaggcgaaa gagaaagata tttggaagcc tggccttcct gcgacgcaaa    180
cggaaaatct tcggctcact ggcattcttg aggagaaagc gcaaaatatt cgggtctttg    240
gcctttctgc gccggaagcg caagatcttc gggtccttgg ctttcttgag acgaaaacgc    300
aaaatatttg gtctcttgc cttcctcagg cgaaagcgga gattttcgg ttcccttgcc    360 ttccttaaag acgagcttcg tgccaagcga tccggaagcg agcccctgt aaagcagact    420 ttgaattttg accttctcaa gttggcggga gacgtcgagt ccaaccctgg gcccatggcc    480
gtcatggcgc cccgaaccct cgtcctgcta ctctcggggg ctctggccct gacccagacc    540
tgggcgggct ctcactccat gaggtatttc ttcacatccg tgtcccggcc cggccgcggg    600
gagccccgct tcatcgcagt gggctacgtg gacgacacgc agttcgtgcg gttcgacagc    660
```

```
gacgccgcga gccagaggat ggagccgcgg gcgccgtgga tagagcagga gggtccggag      720
tattgggacg gggagacacg gaaagtgaag gcccactcac agactcaccg agtggacctg      780
gggaccctgc gcggctacta caaccagagc gaggccggtt ctcacaccgt ccagaggatg      840
tatggctgcg acgtggggtc ggactggcgc ttcctccgcg gtaccacca gtacgcctac       900 gacggcaagg attacatcgc cctgaaagag gacctgcgct cttggaccgc ggcggacatg      960
gcagctcaga ccaccaagca caagtgggag cggcccatg tggcggagca gttgagagcc      1020
tacctggagg gcacgtgcgt ggagtggctc cgcagatacc tggagaacgg gaaggagacg     1080
ctgcagcgca cggacgcccc caaaacgcat atgactcacc acgctgtctc tgaccatgaa     1140
gccaccctga ggtgctgggc cctgagcttc taccctgcgg agatcacact gacctggcag     1200
cgggatgggg aggaccagac ccaggacacg gagctcgtgg agaccaggcc tgcaggggat     1260
ggaaccttcc agaagtgggc ggctgtggtg gtgccttctg gacaggagca gagatacacc     1320
tgccatgtgc agcatgaggg tttgcccaag cccctcaccc tgagatggga gccgtcttcc     1380
cagcccacca tccccatcgt gggcatcatt gctggcctgg ttctctttgg agctgtgatc     1440
actggagctg tggtcgctgc tgtgatgtgg aggaggaaga gctcagatag aaaaggaggg     1500
agctactctc aggctgcaag cagtgacagt gcccagggct ctgatgtgtc tctcacagct     1560
tgtaaagtgt ga                                                         1572
```

<210> SEQ ID NO 28
<211> LENGTH: 22
<212> TYPE: PRT
<213> ORGANISM: Homo sapiens

<400> SEQUENCE: 28

Met Lys Gly Ser Ile Phe Thr Leu Phe Leu Phe Ser Val Leu Phe Ala
1               5                   10                  15

Ile Ser Glu Val Arg Ser
            20

<210> SEQ ID NO 29
<211> LENGTH: 365
<212> TYPE: PRT
<213> ORGANISM: Homo sapiens

<400> SEQUENCE: 29

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Gly Glu Thr Arg Lys Val Lys Ala His Ser Gln
                85                  90                  95

Thr His Arg Val Asp Leu Gly Thr Leu Arg Gly Tyr Tyr Asn Gln Ser
            100                 105                 110

Glu Ala Gly Ser His Thr Val Gln Arg Met Tyr Gly Cys Asp Val Gly
        115                 120                 125

Ser Asp Trp Arg Phe Leu Arg Gly Tyr His Gln Tyr Ala Tyr Asp Gly

```
                130               135                140
Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
        195                 200                 205

Pro Lys Thr His Met Thr His His Ala Val Ser Asp His Glu Ala Thr
210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
                260                 265                 270

Val Pro Ser Gly Gln Glu Gln Arg Tyr Thr Cys His Val Gln His Glu
            275                 280                 285

Gly Leu Pro Lys Pro Leu Thr Leu Arg Trp Glu Pro Ser Ser Gln Pro
        290                 295                 300

Thr Ile Pro Ile Val Gly Ile Ile Ala Gly Leu Val Leu Phe Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Ser Gln Ala Ala Ser Ser Asp Ser
                340                 345                 350

Ala Gln Gly Ser Asp Val Ser Leu Thr Ala Cys Lys Val
            355                 360                 365

<210> SEQ ID NO 30
<211> LENGTH: 264
<212> TYPE: DNA
<213> ORGANISM: Homo sapiens

<400> SEQUENCE: 30
catccggaca aagcctgcgc gcgccccgcc ccgccattgg ccgtaccgcc ccgcgccgcc      60
gccccatctc gccccctcgcc gccgggtccg gcgcgttaaa gccaatagga accgccgccg    120
ttgttcccgt cacggccggg gcagccaatt gtggcggcgc tcggcggctc gtggctcttt    180
cgcggcaaaa aggatttggc gcgtaaaagt ggccgggact ttgcaggcag cggcggccgg    240
gggcggagcg ggatcgagcc ctcg                                           264

<210> SEQ ID NO 31
<211> LENGTH: 523
<212> TYPE: PRT
<213> ORGANISM: Artificial sequence
<220> FEATURE:
<223> OTHER INFORMATION: The sequence is synthesized

<400> SEQUENCE: 31

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
```

```
            35                  40                  45
Val Gly Tyr Val Asp Asp Thr Gln Phe Val Arg Phe Asp Ser Asp Ala
             50                  55                  60

Ala Ser Gln Arg Met Glu Pro Arg Ala Pro Trp Ile Glu Gln Glu Gly
 65                  70                  75                  80

Pro Glu Tyr Trp Asp Gly Glu Thr Arg Lys Val Lys Ala His Ser Gln
                 85                  90                  95

Thr His Arg Val Asp Leu Gly Thr Leu Arg Gly Tyr Tyr Asn Gln Ser
            100                 105                 110

Glu Ala Gly Ser His Thr Val Gln Arg Met Tyr Gly Cys Asp Val Gly
            115                 120                 125

Ser Asp Trp Arg Phe Leu Arg Gly Tyr His Gln Tyr Ala Tyr Asp Gly
            130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
            195                 200                 205

Pro Lys Thr His Met Thr His His Ala Val Ser Asp His Glu Ala Thr
            210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Val Gln His Glu
            275                 280                 285

Gly Leu Pro Lys Pro Leu Thr Leu Arg Trp Glu Pro Ser Ser Gln Pro
            290                 295                 300

Thr Ile Pro Ile Val Gly Ile Ile Ala Gly Leu Val Leu Phe Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Ser Gln Ala Ala Ser Ser Asp Ser
            340                 345                 350

Ala Gln Gly Ser Asp Val Ser Leu Thr Ala Cys Lys Val Arg Ala Lys
            355                 360                 365

Arg Ser Gly Ser Gly Ala Pro Val Lys Gln Thr Leu Asn Phe Asp Leu
            370                 375                 380

Leu Lys Leu Ala Gly Asp Val Glu Ser Asn Pro Gly Pro Met Lys Gly
385                 390                 395                 400

Ser Ile Phe Thr Leu Phe Leu Phe Ser Val Leu Phe Ala Ile Ser Glu
                405                 410                 415

Val Arg Ser Lys Ile Phe Gly Ser Leu Ala Phe Leu Arg Arg Lys Arg
            420                 425                 430

Lys Ile Phe Gly Ser Leu Ala Phe Leu Arg Arg Lys Arg Lys Ile Phe
            435                 440                 445

Gly Ser Leu Ala Phe Leu Arg Arg Lys Arg Lys Ile Phe Gly Ser Leu
            450                 455                 460
```

```
Ala Phe Leu Arg Arg Lys Arg Lys Ile Phe Gly Ser Leu Ala Phe Leu
465                 470                 475                 480

Arg Arg Lys Arg Lys Ile Phe Gly Ser Leu Ala Phe Leu Arg Arg Lys
                485                 490                 495

Arg Lys Ile Phe Gly Ser Leu Ala Phe Leu Arg Arg Lys Arg Lys Ile
            500                 505                 510

Phe Gly Ser Leu Ala Phe Leu Lys Asp Glu Leu
        515                 520

<210> SEQ ID NO 32
<211> LENGTH: 523
<212> TYPE: PRT
<213> ORGANISM: Artificial sequence
<220> FEATURE:
<223> OTHER INFORMATION: The sequence is synthesized

<400> SEQUENCE: 32

Met Lys Gly Ser Ile Phe Thr Leu Phe Leu Phe Ser Val Leu Phe Ala
1               5                   10                  15

Ile Ser Glu Val Arg Ser Lys Ile Phe Gly Ser Leu Ala Phe Leu Arg
            20                  25                  30

Arg Lys Arg Lys Ile Phe Gly Ser Leu Ala Phe Leu Arg Arg Lys Arg
        35                  40                  45

Lys Ile Phe Gly Ser Leu Ala Phe Leu Arg Arg Lys Arg Lys Ile Phe
    50                  55                  60

Gly Ser Leu Ala Phe Leu Arg Arg Lys Arg Lys Ile Phe Gly Ser Leu
65                  70                  75                  80

Ala Phe Leu Arg Arg Lys Arg Lys Ile Phe Gly Ser Leu Ala Phe Leu
                85                  90                  95

Arg Arg Lys Arg Lys Ile Phe Gly Ser Leu Ala Phe Leu Arg Arg Lys
            100                 105                 110

Arg Lys Ile Phe Gly Ser Leu Ala Phe Leu Lys Asp Glu Leu Arg Ala
        115                 120                 125

Lys Arg Ser Gly Ser Gly Ala Pro Val Lys Gln Thr Leu Asn Phe Asp
    130                 135                 140

Leu Leu Lys Leu Ala Gly Asp Val Glu Ser Asn Pro Gly Pro Met Ala
145                 150                 155                 160

Val Met Ala Pro Arg Thr Leu Val Leu Leu Ser Gly Ala Leu Ala
                165                 170                 175

Leu Thr Gln Thr Trp Ala Gly Ser His Ser Met Arg Tyr Phe Phe Thr
            180                 185                 190

Ser Val Ser Arg Pro Gly Arg Gly Glu Pro Arg Phe Ile Ala Val Gly
        195                 200                 205

Tyr Val Asp Asp Thr Gln Phe Val Arg Phe Asp Ser Asp Ala Ala Ser
    210                 215                 220

Gln Arg Met Glu Pro Arg Ala Pro Trp Ile Glu Gln Glu Gly Pro Glu
225                 230                 235                 240

Tyr Trp Asp Gly Glu Thr Arg Lys Val Lys Ala His Ser Gln Thr His
                245                 250                 255

Arg Val Asp Leu Gly Thr Leu Arg Gly Tyr Tyr Asn Gln Ser Glu Ala
            260                 265                 270

Gly Ser His Thr Val Gln Arg Met Tyr Gly Cys Asp Val Gly Ser Asp
        275                 280                 285

Trp Arg Phe Leu Arg Gly Tyr His Gln Tyr Ala Tyr Asp Gly Lys Asp
    290                 295                 300
```

Tyr Ile Ala Leu Lys Glu Asp Leu Arg Ser Trp Thr Ala Asp Met
305                 310                 315                 320

Ala Ala Gln Thr Thr Lys His Lys Trp Glu Ala His Val Ala Glu
            325                 330                 335

Gln Leu Arg Ala Tyr Leu Glu Gly Thr Cys Val Glu Trp Leu Arg Arg
        340                 345                 350

Tyr Leu Glu Asn Gly Lys Glu Thr Leu Gln Arg Thr Asp Ala Pro Lys
            355                 360                 365

Thr His Met Thr His His Ala Val Ser Asp His Glu Ala Thr Leu Arg
        370                 375                 380

Cys Trp Ala Leu Ser Phe Tyr Pro Ala Glu Ile Thr Leu Thr Trp Gln
385                 390                 395                 400

Arg Asp Gly Glu Asp Gln Thr Gln Asp Thr Glu Leu Val Glu Thr Arg
                405                 410                 415

Pro Ala Gly Asp Gly Thr Phe Gln Lys Trp Ala Ala Val Val Val Pro
            420                 425                 430

Ser Gly Gln Glu Gln Arg Tyr Thr Cys His Val Gln His Glu Gly Leu
        435                 440                 445

Pro Lys Pro Leu Thr Leu Arg Trp Glu Pro Ser Ser Gln Pro Thr Ile
    450                 455                 460

Pro Ile Val Gly Ile Ile Ala Gly Leu Val Leu Phe Gly Ala Val Ile
465                 470                 475                 480

Thr Gly Ala Val Val Ala Ala Val Met Trp Arg Arg Lys Ser Ser Asp
                485                 490                 495

Arg Lys Gly Gly Ser Tyr Ser Gln Ala Ala Ser Ser Asp Ser Ala Gln
            500                 505                 510

Gly Ser Asp Val Ser Leu Thr Ala Cys Lys Val
        515                 520

<210> SEQ ID NO 33
<211> LENGTH: 22
<212> TYPE: DNA
<213> ORGANISM: Artificial sequence
<220> FEATURE:
<223> OTHER INFORMATION: The sequence is synthesized

<400> SEQUENCE: 33
gcctctggaa tcctttctct tg                                              22

<210> SEQ ID NO 34
<211> LENGTH: 21
<212> TYPE: DNA
<213> ORGANISM: Artificial sequence
<220> FEATURE:
<223> OTHER INFORMATION: The sequence is synthesized

<400> SEQUENCE: 34
tcagctggac cacagccgca g                                               21

<210> SEQ ID NO 35
<211> LENGTH: 1098
<212> TYPE: DNA
<213> ORGANISM: Homo sapiens

<400> SEQUENCE: 35
atggccgtca tggcgcccg aaccctcgtc ctgctactct cgggggctct ggccctgacc      60
cagacctggg cgggctctca ctccatgagg tatttcttca catccgtgtc ccggcccggc     120

| | | | | |
|---|---|---|---|---|
| cgcggggagc | cccgcttcat | cgcagtgggc | tacgtggacg | acacgcagtt cgtgcggttc | 180 |
| gacagcgacg | ccgcgagcca | gaggatggag | ccgcgggcgc | cgtggataga gcaggagggt | 240 |
| ccggagtatt | gggacgggga | gacacggaaa | gtgaaggccc | actcacagac tcaccgagtg | 300 |
| gacctgggga | ccctgcgcgg | ctactacaac | cagagcgagg | ccggttctca caccgtccag | 360 |
| aggatgtatg | gctgcgacgt | ggggtcggac | tggcgcttcc | tccgcgggta ccaccagtac | 420 |
| gcctacgacg | gcaaggatta | catcgccctg | aaagaggacc | tgcgctcttg gaccgcggcg | 480 |
| gacatggcag | ctcagaccac | caagcacaag | tgggaggcgg | cccatgtggc ggagcagttg | 540 |
| agagcctacc | tggagggcac | gtgcgtggag | tggctccgca | gatacctgga gaacgggaag | 600 |
| gagacgctgc | agcgcacgga | cgcccccaaa | acgcatatga | ctcaccacgc tgtctctgac | 660 |
| catgaagcca | ccctgaggtg | ctgggccctg | agcttctacc | ctgcggagat cacactgacc | 720 |
| tggcagcggg | atggggagga | ccagacccag | gacacggagc | tcgtggagac caggcctgca | 780 |
| ggggatggaa | ccttccagaa | gtgggcggct | gtggtggtgc | cttctggaca ggagcagaga | 840 |
| tacacctgcc | atgtgcagca | tgagggtttg | cccaagcccc | tcaccctgag atgggagccg | 900 |
| tcttcccagc | ccaccatccc | catcgtgggc | atcattgctg | gcctggttct ctttggagct | 960 |
| gtgatcactg | gagctgtggt | cgctgctgtg | atgtggagga | ggaagagctc agatagaaaa | 1020 |
| ggagggagct | actctcaggc | tgcaagcagt | gacagtgccc | agggctctga tgtgtctctc | 1080 |
| acagcttgta | aagtgtga | | | | 1098 |

<210> SEQ ID NO 36
<211> LENGTH: 70
<212> TYPE: PRT
<213> ORGANISM: Artificial sequence
<220> FEATURE:
<223> OTHER INFORMATION: The sequence is synthesized

<400> SEQUENCE: 36

Met Lys Gly Ser Ile Phe Thr Leu Phe Leu Phe Ser Val Leu Phe Ala
1               5                   10                  15

Ile Ser Glu Val Arg Ser Lys Ile Phe Gly Ser Leu Ala Phe Leu Arg
                20                  25                  30

Arg Lys Arg Lys Ile Phe Gly Ser Leu Ala Phe Leu Arg Arg Lys Arg
            35                  40                  45

Lys Ile Phe Gly Ser Leu Ala Phe Leu Arg Arg Lys Arg Lys Ile Phe
        50                  55                  60

Gly Ser Leu Ala Phe Leu
65                  70

<210> SEQ ID NO 37
<211> LENGTH: 30
<212> TYPE: DNA
<213> ORGANISM: Artificial sequence
<220> FEATURE:
<223> OTHER INFORMATION: The sequence is synthesized

<400> SEQUENCE: 37
agagctagcg aattcaacat ggccgtcatg                                    30

<210> SEQ ID NO 38
<211> LENGTH: 37
<212> TYPE: DNA
<213> ORGANISM: Artificial sequence
<220> FEATURE:
<223> OTHER INFORMATION: The sequence is synthesized

```
<400> SEQUENCE: 38
tgattgtcga cgcccttaaa gctcgtcttt aaggaag                              37

<210> SEQ ID NO 39
<211> LENGTH: 31
<212> TYPE: DNA
<213> ORGANISM: Artificial sequence
<220> FEATURE:
<223> OTHER INFORMATION: The sequence is synthesized

<400> SEQUENCE: 39
tagagatctg gtaccaacat ggccgtcatg g                                    31

<210> SEQ ID NO 40
<211> LENGTH: 37
<212> TYPE: DNA
<213> ORGANISM: Artificial sequence
<220> FEATURE:
<223> OTHER INFORMATION: The sequence is synthesized

<400> SEQUENCE: 40
ggctcgagcg gccgcttaaa gctcgtcttt aaggaag                              37

<210> SEQ ID NO 41
<211> LENGTH: 23
<212> TYPE: DNA
<213> ORGANISM: Artificial sequence
<220> FEATURE:
<223> OTHER INFORMATION: The sequence is synthesized

<400> SEQUENCE: 41
ggaagatctg gactgaaaat gag                                             23

<210> SEQ ID NO 42
<211> LENGTH: 24
<212> TYPE: DNA
<213> ORGANISM: Artificial sequence
<220> FEATURE:
<223> OTHER INFORMATION: The sequence is synthesized

<400> SEQUENCE: 42
tgaggtcaga tgtaaccaag atta                                            24

<210> SEQ ID NO 43
<211> LENGTH: 33
<212> TYPE: DNA
<213> ORGANISM: Artificial sequence
<220> FEATURE:
<223> OTHER INFORMATION: The sequence is synthesized

<400> SEQUENCE: 43
cgcgtcgact actgtaatag taatcaatta cgg                                  33

<210> SEQ ID NO 44
<211> LENGTH: 33
<212> TYPE: DNA
<213> ORGANISM: Artificial sequence
<220> FEATURE:
<223> OTHER INFORMATION: The sequence is synthesized

<400> SEQUENCE: 44
gacgtcgact aagatacatt gatgagtttg gac                                  33

<210> SEQ ID NO 45
<211> LENGTH: 33
```

```
<212> TYPE: DNA
<213> ORGANISM: Artificial sequence
<220> FEATURE:
<223> OTHER INFORMATION: The sequence is synthesized

<400> SEQUENCE: 45
ccgctcgaga tgaaaggttc catcttcaca ttg                              33

<210> SEQ ID NO 46
<211> LENGTH: 33
<212> TYPE: DNA
<213> ORGANISM: Artificial sequence
<220> FEATURE:
<223> OTHER INFORMATION: The sequence is synthesized

<400> SEQUENCE: 46
ccgctcgagt taaagctcgt ctttaaggaa ggc                              33

<210> SEQ ID NO 47
<211> LENGTH: 39
<212> TYPE: DNA
<213> ORGANISM: Artificial sequence
<220> FEATURE:
<223> OTHER INFORMATION: The sequence is synthesized

<400> SEQUENCE: 47
ttccggatcg cttggcacga agctcgtctt taaggaagg                        39

<210> SEQ ID NO 48
<211> LENGTH: 39
<212> TYPE: DNA
<213> ORGANISM: Artificial sequence
<220> FEATURE:
<223> OTHER INFORMATION: The sequence is synthesized

<400> SEQUENCE: 48
ccttccttaa agacgagctt cgtgccaagc gatccggaa                        39

<210> SEQ ID NO 49
<211> LENGTH: 38
<212> TYPE: DNA
<213> ORGANISM: Artificial sequence
<220> FEATURE:
<223> OTHER INFORMATION: The sequence is synthesized

<400> SEQUENCE: 49
cggggcgcca tgacggccat gggcccaggg ttggactc                         38

<210> SEQ ID NO 50
<211> LENGTH: 38
<212> TYPE: DNA
<213> ORGANISM: Artificial sequence
<220> FEATURE:
<223> OTHER INFORMATION: The sequence is synthesized

<400> SEQUENCE: 50
gagtccaacc ctgggcccat ggccgtcatg gcgccccg                         38

<210> SEQ ID NO 51
<211> LENGTH: 32
<212> TYPE: DNA
<213> ORGANISM: Artificial sequence
<220> FEATURE:
<223> OTHER INFORMATION: The sequence is synthesized

<400> SEQUENCE: 51
```
cttctcgagt cacactttac aagctgtgag ag					32

<210> SEQ ID NO 52
<211> LENGTH: 36
<212> TYPE: DNA
<213> ORGANISM: Artificial sequence
<220> FEATURE:
<223> OTHER INFORMATION: The sequence is synthesized

<400> SEQUENCE: 52
agagctagcg aattcaacat gggctgcagg ctgctc					36

<210> SEQ ID NO 53
<211> LENGTH: 42
<212> TYPE: DNA
<213> ORGANISM: Artificial sequence
<220> FEATURE:
<223> OTHER INFORMATION: The sequence is synthesized

<400> SEQUENCE: 53
ggatcgcttg gcacgtgaat tctttctttt gaccatagcc at					42

<210> SEQ ID NO 54
<211> LENGTH: 39
<212> TYPE: DNA
<213> ORGANISM: Artificial sequence
<220> FEATURE:
<223> OTHER INFORMATION: The sequence is synthesized

<400> SEQUENCE: 54
tccaaccctg ggcccatgct cctgttgctc ataccagtg					39

<210> SEQ ID NO 55
<211> LENGTH: 35
<212> TYPE: DNA
<213> ORGANISM: Artificial sequence
<220> FEATURE:
<223> OTHER INFORMATION: The sequence is synthesized

<400> SEQUENCE: 55
gttgattgtc gacgccctca actggaccac agcct					35

<210> SEQ ID NO 56
<211> LENGTH: 31
<212> TYPE: PRT
<213> ORGANISM: Artificial sequence
<220> FEATURE:
<223> OTHER INFORMATION: The sequence is synthesized

<400> SEQUENCE: 56

Met Lys Gly Ser Ile Phe Thr Leu Phe Leu Phe Ser Val Leu Phe Ala
1               5                   10                  15

Ile Ser Glu Val Arg Ser Lys Ile Phe Gly Ser Leu Ala Phe Leu
            20                  25                  30

<210> SEQ ID NO 57
<211> LENGTH: 93
<212> TYPE: DNA
<213> ORGANISM: Artificial sequence
<220> FEATURE:
<223> OTHER INFORMATION: The sequence is synthesized

<400> SEQUENCE: 57
atgaaaggtt ccatcttcac attgtttttg ttctccgtat tgttcgcaat cagcgaagtc					60 cgatcaaaaa tatttgggtc tctcgcattc ctc					93

<210> SEQ ID NO 58
<211> LENGTH: 210
<212> TYPE: DNA
<213> ORGANISM: Artificial sequence
<220> FEATURE:
<223> OTHER INFORMATION: The sequence is synthesized

<400> SEQUENCE: 58

```
atgaaaggtt ccatcttcac attgttttg ttctccgtat tgttcgcaat cagcgaagtc      60
cgatcaaaaa tatttgggtc tctcgcattc ctccgcagaa agaggaaaat cttcggtagt     120
ttggccttcc ttaggcgaaa gagaaagata tttggaagcc tggccttcct gcgacgcaaa    180
cggaaaatct tcggctcact ggcattcttg                                     210
```

<210> SEQ ID NO 59
<211> LENGTH: 378
<212> TYPE: DNA
<213> ORGANISM: Artificial sequence
<220> FEATURE:
<223> OTHER INFORMATION: The sequence is synthesized

<400> SEQUENCE: 59

```
atgaaaggtt ccatcttcac attgttttg ttctccgtat tgttcgcaat cagcgaagtc      60
cgatcaaaaa tatttgggtc tctcgcattc ctccgcagaa agaggaaaat cttcggtagt     120
ttggccttcc ttaggcgaaa gagaaagata tttggaagcc tggccttcct gcgacgcaaa    180
cggaaaatct tcggctcact ggcattcttg aggagaaagc gcaaaatatt cgggtctttg    240
gcctttctgc gccggaagcg caagatcttc gggtccttgg cttcttgag acgaaaacgc     300 aaaatatttg gtctcttgc cttcctcagg cgaaagcgga agattttcgg ttcccttgcc     360
ttccttaaag acgagctt                                                  378
```

<210> SEQ ID NO 60
<211> LENGTH: 122
<212> TYPE: PRT
<213> ORGANISM: Artificial sequence
<220> FEATURE:
<223> OTHER INFORMATION: The sequence is synthesized

<400> SEQUENCE: 60

```
Met Lys Gly Ser Ile Phe Thr Leu Phe Leu Phe Ser Val Leu Phe Ala
1               5                   10                  15

Ile Ser Glu Val Arg Ser Lys Ile Phe Gly Ser Leu Ala Phe Leu Arg
            20                  25                  30

Arg Lys Arg Lys Ile Phe Gly Ser Leu Ala Phe Leu Arg Arg Lys Arg
        35                  40                  45

Lys Ile Phe Gly Ser Leu Ala Phe Leu Arg Arg Lys Arg Lys Ile Phe
    50                  55                  60

Gly Ser Leu Ala Phe Leu Arg Arg Lys Arg Lys Ile Phe Gly Ser Leu
65                  70                  75                  80

Ala Phe Leu Arg Arg Lys Arg Lys Ile Phe Gly Ser Leu Ala Phe Leu
                85                  90                  95

Arg Arg Lys Arg Lys Ile Phe Gly Ser Leu Ala Phe Leu Arg Arg Lys
            100                 105                 110

Arg Lys Ile Phe Gly Ser Leu Ala Phe Leu
        115                 120
```

<210> SEQ ID NO 61

```
<211> LENGTH: 366
<212> TYPE: DNA
<213> ORGANISM: Artificial sequence
<220> FEATURE:
<223> OTHER INFORMATION: The sequence is synthesized

<400> SEQUENCE: 61
atgaaaggtt ccatcttcac attgttttg ttctccgtat tgttcgcaat cagcgaagtc      60
cgatcaaaaa tatttgggtc tctcgcattc ctccgcagaa agaggaaaat cttcggtagt    120
ttggccttcc ttaggcgaaa gagaaagata tttggaagcc tggccttcct gcgacgcaaa    180
cggaaaatct tcggctcact ggcattcttg aggagaaagc gcaaaatatt cgggtctttg    240
gcctttctgc gccggaagcg caagatcttc gggtccttgg cttcttgag acgaaaacgc     300 aaaatatttg ggtctcttgc cttcctcagg cgaaagcgga agattttcgg ttcccttgcc    360
ttcctt                                                                366
```